(12) United States Patent
Singh et al.

(10) Patent No.: US 7,538,195 B2
(45) Date of Patent: May 26, 2009

(54) ANTI-IGF-I RECEPTOR ANTIBODY

(75) Inventors: Rajeeva Singh, Cambridge, MA (US); Daniel J. Tavares, Natick, MA (US); Nancy E. Dagdigian, Acton, MA (US)

(73) Assignee: Immunogen Inc., Waltham, MA (US)

( * ) Notice: Subject to any disclaimer, the term of this patent is extended or adjusted under 35 U.S.C. 154(b) by 125 days.

(21) Appl. No.: 10/170,390

(22) Filed: Jun. 14, 2002

(65) Prior Publication Data
US 2003/0235582 A1 Dec. 25, 2003

(51) Int. Cl.
- C12P 21/08 (2006.01)
- C07K 16/00 (2006.01)
- A61K 39/395 (2006.01)
- A61K 49/00 (2006.01)
- C07H 21/04 (2006.01)
- G01N 33/574 (2006.01)

(52) U.S. Cl. .................. 530/387.3; 424/9.1; 424/133.1; 424/141.1; 424/143.1; 424/155.1; 424/178.1; 424/181.1; 424/183.1; 435/69.6; 435/70.21; 530/388.1; 530/388.22; 530/388.8; 530/391.7

(58) Field of Classification Search .............. 530/387.1, 530/387.3, 388.1, 388.22, 391.3, 391.7; 435/69.1, 435/69.6; 424/130.1, 133.1, 141.1, 143.1, 424/155.1, 181.1, 183.1
See application file for complete search history.

(56) References Cited

U.S. PATENT DOCUMENTS

| 5,530,101 | A * | 6/1996 | Queen et al. |
| 2003/0099655 | A1* | 5/2003 | Watkins et al. |
| 2003/0165502 | A1 | 9/2003 | Fujita-Yamaguchi |
| 2003/0195147 | A1 | 10/2003 | Pillutla et al. |
| 2003/0236190 | A1 | 12/2003 | Pillutla et al. |
| 2004/0023887 | A1 | 2/2004 | Pillutla et al. |
| 2004/0086503 | A1 | 5/2004 | Cohen et al. |

FOREIGN PATENT DOCUMENTS

| WO | WO 00/34780 | 6/2000 |
| WO | WO 02/053596 | 7/2002 |
| WO | WO 03/059951 | 7/2003 |
| WO | WO 03/100008 | 12/2003 |
| WO | WO 03/106621 | 12/2003 |
| WO | WO 2004/071529 | 8/2004 |
| WO | WO 2004/083248 | 9/2004 |

OTHER PUBLICATIONS

Fundamental Immunology, William E. Paul, M.D. ed., 3d ed., p. 242, 1993.*
Rudikoff et al. Proc. Natl. Acad. Sci. USA, 79:1979-1983, 1982.*
Zia et al. Journal of Cellular Biochemistry Supplement, 24:269-275, 1996.*
Roguska et al. Proc. .Natl. Acad. Sci. USA, 91:969-973, 1994.*
William E. Paul. Fundamental Immunology, 3rd Edition, pp. 292-295, 1993.*
Coleman P. M. Research in Immunology, 145:33-36, 1994.*
Soos et al. The Journal of Biological Chemistry, 267:12955-12963, 1992.*
Cullen et al. Cancer Research, 50:48-53, 1990.*
Maloney et al, *Cancer Research*, 63(16):5073-5083 (2003).
Li et al, *Cancer Immunol. Immunother.*, 49:243-252 (2000).
Steele-Perkins and Roth, *Biochem. Biophys. Res. Comm.* 171(3):1244-1251 (1990).
Harlow and Lane, eds. Using Antibodies, A Laboratory Manual, pp. 81-97, 126-127, 166-169, Cold Spring Harbor Press 1999.
Kato et al. , *J. Biol. Chem.* 268:2655-2661 (1993).
Grant et al., *J. Clinical Endocrinology and Metabolism* 83:3252-3257 (1998).
Supplemental European Search Report dated Jun. 27, 2005.

* cited by examiner

*Primary Examiner*—David J. Blanchard
(74) *Attorney, Agent, or Firm*—Sughrue Mion, PLLC

(57) ABSTRACT

Antibodies, humanized antibodies, resurfaced antibodies, antibody fragments, derivatized antibodies, and conjugates of these molecules with cytotoxic agents, which specifically bind to and inhibit insulin-like growth factor-I receptor, antagonize the effects of IGF-I and are substantially devoid of agonist activity toward the insulin-like growth factor-I receptor. These molecules can be conjugated to cytotoxic agents for use in the treatment of tumors that express elevated levels of IGF-I receptor, such as breast cancer, colon cancer, lung cancer, ovarian carcinoma, synovial sarcoma and pancreatic cancer. These molecules can also be labeled for in vitro and in vivo diagnostic uses, such as in the diagnosis and imaging of tumors that express elevated levels of IGF-I receptor.

29 Claims, 25 Drawing Sheets

FIGURE 1
Y1251F IGF-I Receptor Cells
Insulin Receptor Cells
Goatαmouse-IgG-FITC only
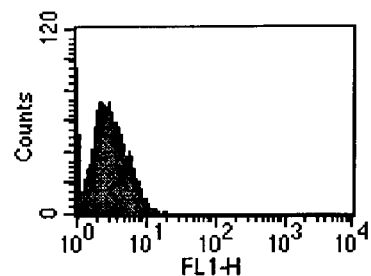
Goatαmouse-IgG-FITC only
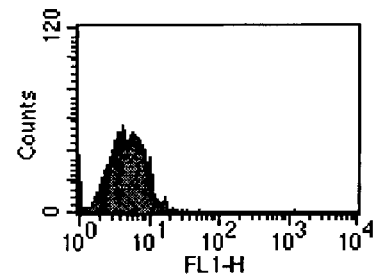
100 nM αEM164
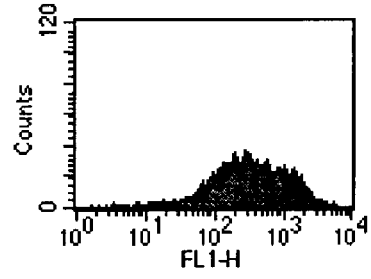
100 nM αEM164
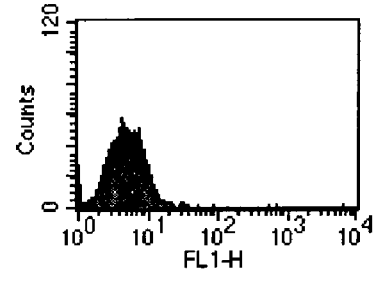
100 nM α1H7
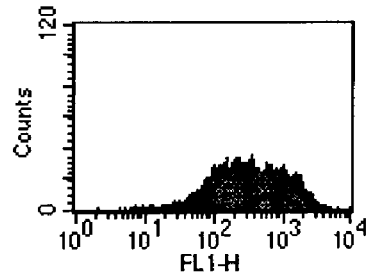
100 nM αIR
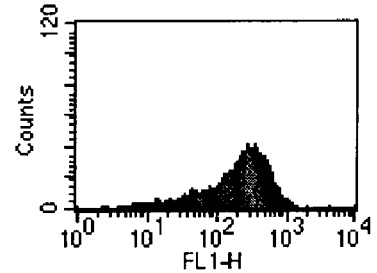

Titration curve for binding of EM164 antibody to biotinylated IGF-I Receptor

Inhibition of IGF-I-Stimulated Autophosphorylation of
IGF-I Receptor in MCF-7 Cells by EM164 Antibody Inhibition of IGF-I-Stimulated IRS-1-Phosphorylation in MCF-7 Cells by EM 164 antibody

Inhibition of IGF-I-Stimulated Signal Transduction in SaOS-2 Cells by EM164 Antibody Competition of binding of humanized EM164 antibody
(version 1.0) to immobilized biotinylated IGF-I receptor
by murine EM164 antibody (1.06 to 10.6-fold molar concentration
range)

FIGURE 12

→
Murine EM164 Light Chain

```
  1 atgaagttgcctgttaggctgttggtgctgatgttctggattcct
  1  M  K  L  P  V  R  L  L  V  L  M  F  W  I  P 46 gcttccagtagtgatgttttgatgacccaaactccactctccctg
 16  A  S  S  S  D  V  L  M  T  Q  P  L  S  L
                ↑VK 91 cctgtcagtcttggagatcaagcctccatctcttgcagatctagt
 31  P  V  S  L  G  D  Q  A  S  I  S  C  R  S  S
                                          ‾‾‾‾‾‾‾
                                            CDR1

136 cagagcattgtacatagtaatgtaaacacctatttagaatggtac
 46  Q  S  I  V  H  S  N  V  N  T  Y  L  E  W  Y
    ‾‾‾‾‾‾‾‾‾‾‾‾‾‾‾‾‾‾‾‾‾‾‾‾‾‾‾‾‾‾‾‾‾‾‾‾‾
                    CDR1

181 ctgcagaaaccaggccagtctccaaagctcctgatctacaaagtt
 61  L  Q  K  P  G  Q  S  P  K  L  L  I  Y  K  V
                                             ‾‾‾‾
                                             CDR2

226 tccaaccgattttctggggtcccagacaggttcagtggcagtgga
 76  S  N  R  F  S  G  V  P  D  R  F  S  G  S  G
    ‾‾‾‾‾‾‾‾‾‾‾‾‾‾
         CDR2

271 tcaggacagatttcacactcaggatcagcagagtggaggctgag
 91  S  G  T  D  F  T  L  R  I  S  R  V  E  A  E 316 gatctgggaatttattactgctttcaaggttcacatgttcctccg
106  D  L  G  I  Y  Y  C  F  Q  G  S  H  V  P  P
                         ‾‾‾‾‾‾‾‾‾‾‾‾‾‾‾‾‾‾‾‾‾‾‾
                                           CDR3

361 acgttcggtggaggcaccaagctggaaatcaaacgg
121  T  F  G  G  G  T  K  L  E  I  K  R
     ‾
```

FIGURE 13

Murine EM164 Heavy Chain

```
  1 atgggatggagctatatcatcctcttttggtagcaacagctaca
  1  M  G  W  S  Y  I  I  L  F  L  V  A  T  A  T 46 gaagtccactcccaggtccaactgcagcagtctggggctgaactg
 16  E  V  H  S  Q  V  Q  L  Q  Q  S  G  A  E  L
               ⊥VH 91 gtgaagcctggggcttcagtgaagctgtcctgtaaggcttctggc
 31  V  K  P  G  A  S  V  K  L  S  C  K  A  S  G 136 tacaccttcaccagctactggatgcactgggtgaagcagaggcct
 46  Y  T  F  T  S  Y  W  M  H  W  V  K  Q  R  P
                  ‾‾‾‾‾‾‾‾‾‾‾
                     CDR1

181 ggacaaggccttgagtggattggagagattaatcctagcaacggt
 61  G  Q  G  L  E  W  I  G  E  I  N  P  S  N  G
                              ‾‾‾‾‾‾‾‾‾‾‾‾‾‾
                                  CDR2

226 cgtactaactacaatgagaagttcaagaggaaggccacactgact
 76  R  T  N  Y  N  E  K  F  K  R  K  A  T  L  T
     ‾‾‾‾‾‾‾‾‾‾‾‾‾‾‾‾‾‾‾‾‾‾‾‾‾‾‾‾
                CDR2

271 gtagacaaatcctccagcacagcctacatgcaactcagcagcctg
 91  V  D  K  S  S  S  T  A  Y  M  Q  L  S  S  L 316 acatctgaggactctgcggtctattactttgcaagaggaagacca
106  T  S  E  D  S  A  V  Y  Y  F  A  R  G  R  P
                                       ‾‾‾‾‾‾‾‾
                                         CDR3

361 gattactacggtagtagcaagtggtacttcgatgtctggggcgca
121  D  Y  Y  G  S  S  K  W  Y  F  D  V  W  G  A
     ‾‾‾‾‾‾‾‾‾‾‾‾‾‾‾‾‾‾‾‾‾‾‾‾‾‾‾‾‾‾‾
                 CDR3

406 gggaccacggtcaccgtctcctca
136  G  T  T  V  T  V  S  S
```

FIGURE 14

Murine EM164 CDRs

Light Chain

CDR1: R S S Q S I V H S N V N T Y L E

CDR2: K V S N R F S

CDR3: F Q G S H V P P T

Heavy Chain

CDR1: S Y W M H

CDR2: E I N P S N G R T N Y N E K F K R

CDR3: G R P D Y Y G S S K W Y F D V

AbM Heavy Chain

CDR1: G Y T F T S Y W M H

CDR2: E I N P S N G R T N

CDR3: G R P D Y Y G S S K W Y F D V

FIGURE 15

Germline sequence comparisons

| Light Chain | | 50 |
|---|---|---|
| Cr1 | - DVLMTQTPLSLPVSLGDQASISCRSSQSIVHSNGNTYLEWYLQKPGQSPK | |
| muEM164 | - ------------------------------V----------------- | |
| | | 100 |
| Cr1 | - LLIYKVSNRFSGVPDRFSGSGSGTDFTLKISRVEAEDLGVYYCFQGSHVP | |
| muEM164 | - ---------------------------R----------I---------- | |

| Heavy Chain | | 50 |
|---|---|---|
| J558.c | - QVQLQQPGAELVKPGASVKLSCKASGYTFTSYWMHWVKQRPGQGLEWIGE | |
| muEM164 | - ------S------------------------------------------ | |
| | | 98 |
| J558.c | - INPSNGRTNYNEKFKSKATLTVDKSSSTAYMQLSSPTSEDSAVYYCAR | |
| muEM164 | - ---------------R-------------------L---------F-- | |

Cloning and Mammalian Expression Plasmid Maps

FIGURE 18

10 Most Homologous Heavy Chain Sequence Alignment

```
                 1.........10........20........30........40........50
    em164 HC     QVQLQQSGAE  LVKPGSSVKL  SCKRSGYTFT  SYWMHWVKQR  PGQGLEWIGE
    1nqb         QVQLQQSGAE  LVKPGASVKL  CKASGYTFT   SYWMHWVKQR  PGRGLEWIGR
    1ngp         QVQLQQPGAE  LVKPGASVKL  CKASGYTFT   SYWMHWVKQR  PGRGLEWIGR
    1fbi         QVQLQQPGAE  LVKPGASVKL  CKASGYTFT   SYWMHWVQG   PGQGLEWIGE
    1afv         QVQLQQPSV   LVRPGASVKL  CKASGYTFT   SSWIHWAKQR  PGQGLEWIGE
    1yuh         QVQFQQSGAE  LVKPGASVKL  CKASGYTFT   SYLMHWIKQR  PGRGLEWIGR
    1plg         QIQLQQSGPE  LVRPGASVKI  CKASGYTFT   DYYIHWVKQR  PGEGLERIGW
    1d5b         QVQLQQSGAE  LMKPGASVKI  CKATGYTFS   SFWIEWVKQR  PGHGLEWIGE
    1ae6         QIQLQQSGPE  LVKPGASVKI  CKASGYTFT   DYYINWMKQK  PGQGLEWIGW
    1axs         QVQLLESGAE  LMKPGASVKI  CKATGYTFS   SFWIEWVKQR  PGHGLEWIGE
    3hfl         -VQLQQSGAE  LMKPGASVKI  CKASGVTFS   DYWIEWVKQR  PGHGLEWIGE Consensus    qvQlqqsGae  LvkPGASVKx  SCKAsGYTFt  sywxhWvKQr  PGxGLEWIGx ..........60........70........80........90........100
    em164 HC     INPSNGRTNY  NEKFRKATL   VDKSSSTAY   MQLSSLTSED  SAVYFARGR
    1nqb         IDPNSGGTKY  NEKFKSATL   VDKPSSTAY   MQLSSLTSED  SAVYCAR--
    1ngp         IDPNSGGTKI  NEKFKSATL   VDKPSSTAY   MQLSSLTSED  SAVYCAR--
    1fbi         IDPSDSYPNY  NEKFKGATL   VDKSSSTAY   MQLSSLTSED  SAVYCAS--
    1afv         IHPNSGNTNY  NEKFKGATL   VDTSSSTAY   VDLSSLTSED  SAVYCAR--
    1yuh         IDPNNVVTKF  NEKFKSATL   VDKPSSTAY   MELSSLTSED  SAVYCAR--
    1plg         IYPCSGNTKY  NEKFKGRATL  VDTSSSTAV   MQLSSLTSED  SAVYFCAR--
    1d5b         ILPGSGGTHY  NEKFKGKATF  AKSSNATAY   MQLSSESED   SAVYCAKGH
    1ae6         IDPGSGNTKY  NEKFKGRATL  VDTSSSTAY   MQLSSLTSED  TAVYFCAR--
    1axs         ILPGSGGTHY  NEKFKGKATF  AKSSNATAY   MQLSSESED   SAVYCARGH
    3hfl         ILPGSGSTNY  HEKFKGRATF  ATSSSTAV    MQNSLASED   SGVYCLHGN Consensus    IxPxsgxtxy  nEkFKgKATl  TvDksSsTAY  mqLsSLTSED  saVYycar--

..........110.......120.......130.......140.......150
    em164 HC     PDYYGSSKWY  FVGATV      VS
    1nqb         YDYYGSS--Y  FYGQTV      VS
    1ngp         YDYYGSS--Y  FYGQTL      S
    1fbi         LYYYGTSYGV  LYGQSV      VS
    1afv         -WRYGSP-YY  FYGQTL      VS
    1yuh         YAYCRP----  MYGQTV      VS
    1plg         --GGK---FA  MYGQSV      VS
    1d5b         S-YYF---YD  GYGQSV      VS
    1ae6         --EKTTYYYA  MYGQSV      VA
    1axs         S-YYF---YD  GYGQSV      S
    3hfl         --------YD  FGGQTL      VS Consensus    xxyyxxx-xx  xDyWGqGTxv  TVSs
```

FIGURE 19
A.
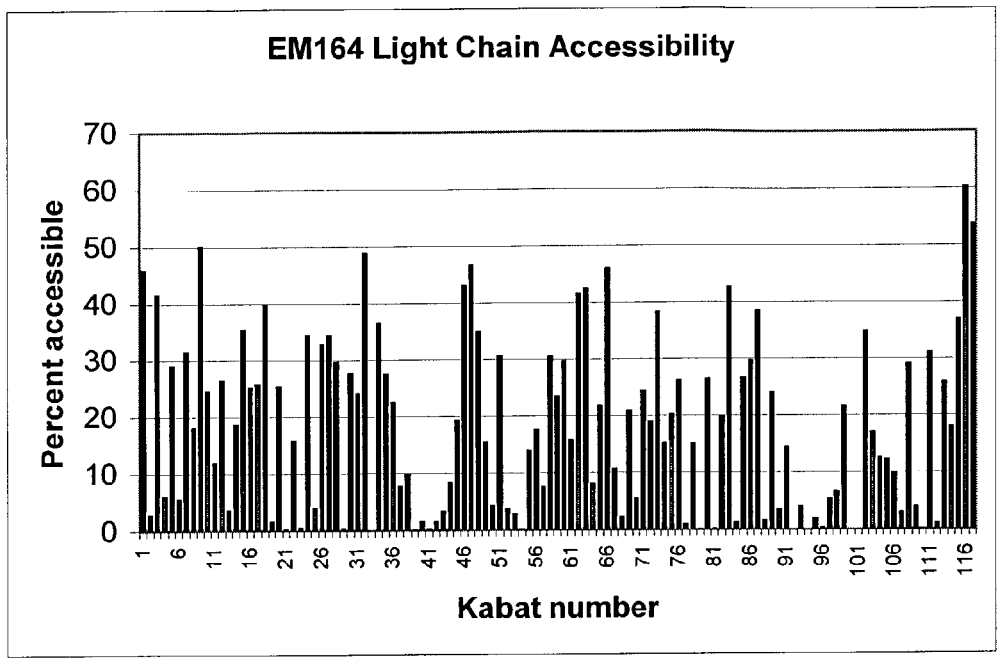
B.
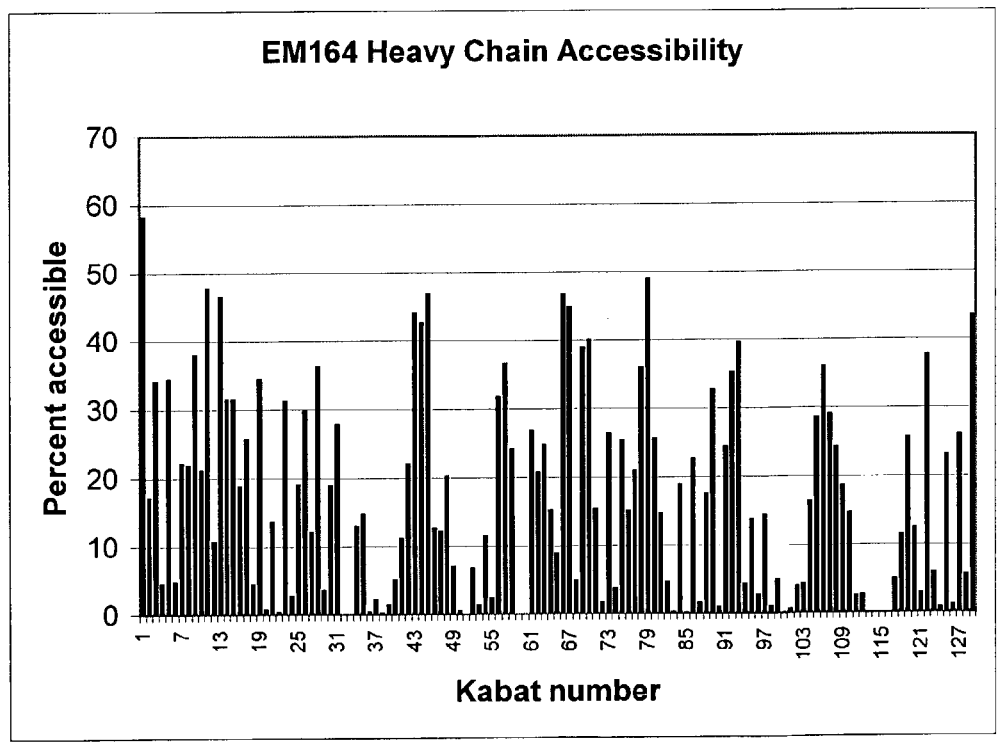

FIGURE 20
Light Chain Variable Region Amino Acid Sequences for Murine and Humanized EM164 Antibodies

```
Kabat #           1          10         20         27c        35         45
muEM164           DVLMTQTPLS LPVSLGDQAS ISCRSSQSIV HSNVNTYLEW YLQKPGQSPK
huEM164 v1.0      DVVMTQTPLS LPVSLGDPAS ISCRSSQSIV HSNVNTYLEW YLQKPGQSPR
huEM164 v1.1      DVLMTQTPLS LPVSLGDPAS ISCRSSQSIV HSNVNTYLEW YLQKPGQSPK
huEM164 v1.2      DVLMTQTPLS LPVSLGDPAS ISCRSSQSIV HSNVNTYLEW YLQKPGQSPR
huEM164 v1.3      DVVMTQTPLS LPVSLGDPAS ISCRSSQSTV HSNVNTYLEW YLQKPGQSPK
changes           *                *                                    *

Kabat #           46         55         65         75         85         95f
muEM164           LLIYKVSNRF SGVPDRFSGS GSGTDFTLRI SRVEAEDLGI YYCFQGSHVP
huEM164 v1.0      LLIYKVSNRF SGVPDRFSGS GAGTDFTLRI SRVEAEDLGI YYCFQGSHVP
huEM164 v1.1      LLIYKVSNRF SGVPDRFSGS GAGTDFTLRI SRVEAEDLGI YYCFQGSHVP
huEM164 v1.2      LLIYKVSNRF SGVPDRFSGS GAGTDFTLRI SRVEAEDLGI YYCFQGSHVP
huEM164 v1.3      LLIYKVSNRF SGVPDRFSGS GAGTDFTLRI SRVEAEDLGI YYCFQGSHVP
changes                                 *

Kabat #           96       105 108
muEM164           PTFGGGTKLE IKR
huEM164 v1.0      PTFGGGTKLE IKR
huEM164 v1.1      PTFGGGTKLE IKR
huEM164 v1.2      PTFGGGTKLE IKR
huEM164 v1.3      PTFGGGTKLE IKR
changes
```

FIGURE 21

Heavy Chain Variable Region Amino Acid Sequences for Murine and Humanized EM164 Antibodies

```
Kabat #   1          10         20         30         40         50
muEM164   QVQLQQSGAE LVKPGASVKL SCKASGYTFT SYWMHWVKQR PGQGLEWIGE
huEM164   QVQLVQSGAE VVKPGASVKL SCKASGYTFT SYWMHWVKQR PGQGLEWIGE
changes        *         *

Kabat #   51         59         69         79         86         96
muEM164   INPSNGRTNY NEKFKRKATL TVDKSSSTAY MQLSSLTSED SAVYYFARGR
huEM164   INPSNGRTNY NQKFQGKATL TVDKSSSTAY MQLSSLTSED SAVYYFARGR
changes                *  **

Kabat #   97         100f       109  113
muEM164   PDYYGSSKWY FDVWGAGTTV TVSS
huEM164   PDYYGSSKWY FDVWGQGTTV TVSS
changes                  *
```

FIGURE 22 huEM164 v1.0 Variable Region DNA and Amino Acid Sequences
Light Chain

```
  1 gatgttgtgatgacccaaactccactctccctgcctgtcagtctt
  1  D  V  V  M  T  Q  P  L  S  L  P  V  S  L 46 ggagatccagcctccatctcttgcagatctagtcagagcatagta
 16  G  D  P  A  S  I  S  C  R  S  S  Q  S  I  V 91 catagtaatgtaaacacctatttagaatggtacctgcagaaacca
 31  H  S  N  V  N  T  Y  L  E  W  Y  L  Q  K  P 136 ggccagtctccaaggctcctgatctacaaagtttccaaccgattt
 46  G  Q  S  P  R  L  L  I  Y  K  V  S  N  R  F 181 tctggggtcccagacaggttcagtggcagtggagcagggacagat
 61  S  G  V  P  D  R  F  S  G  S  G  A  G  T  D 226 ttcacactcaggatcagcagagtggaggctgaggatctgggaatt
 76  F  T  L  R  I  S  R  V  E  A  E  D  L  G  I 271 tattactgctttcaaggttcacatgttcctccgacgttcggtgga
 91  Y  Y  C  F  Q  G  S  H  V  P  P  T  F  G  G 316 ggcaccaaactggaaatcaaacgt
106  G  T  K  L  E  I  K  R
```

Heavy Chain

```
  1 caggtccaactggtgcagtctggggctgaagtggtgaagcctggg
  1  Q  V  Q  L  V  Q  S  G  A  E  V  V  K  P  G 46 gcttcagtgaagctgtcctgtaaggcttctggctacaccttcacc
 16  A  S  V  K  L  S  C  K  A  S  G  Y  T  F  T 91 agctactggatgcactgggtgaagcagaggcctggacaaggcctt
 31  S  Y  W  M  H  W  V  K  Q  R  P  G  Q  G  L 136 gagtggattggagagattaatcctagcaacggtcgtactaactac
 46  E  W  I  G  E  I  N  P  S  N  G  R  T  N  Y 181 aatcagaagttccaggggaaggccacactgactgtagacaaatcc
 61  N  Q  K  F  Q  G  K  A  T  L  T  V  D  K  S 226 tccagcacagcctacatgcaactcagcagcctgacatctgaggac
 76  S  S  T  A  Y  M  Q  L  S  S  L  T  S  E  D 271 tctgcggtctattactttgcaagaggaagaccagattactacggt
 91  S  A  V  Y  Y  F  A  R  G  R  P  D  Y  Y  G 316 agtagcaagtggtacttcgatgtctggggccaagggaccacggtc
106  S  S  K  W  Y  F  D  V  W  G  Q  G  T  T  V 361 accgtctcctca
121  T  V  S  S
```

FIGURE 23 huEM164 v1.1, 1.2, 1.3 Light Chain Variable Region DNA and Amino Acid Sequences v1.1

```
  1  gatgttttgatgacccaaactccactctccctgcctgtcagtctt
  1   D  V  L  M  T  Q  P  L  S  L  P  V  S  L 46  ggagatccagcctccatctcttgcagatctagtcagagcatagta
 16   G  D  P  A  S  I  S  C  R  S  S  Q  S  I  V 91  catagtaatgtaaacacctatttagaatggtacctgcagaaacca
 31   H  S  N  V  N  T  Y  L  E  W  Y  L  Q  K  P 136  ggccagtctccaaagctcctgatctacaaagtttccaaccgattt
 46   G  Q  S  P  K  L  L  I  Y  K  V  S  N  R  F 181  tctggggtcccagacaggttcagtggcagtggagcagggacagat
 61   S  G  V  P  D  R  F  S  G  S  G  A  G  T  D 226  ttcacactcaggatcagcagagtggaggctgaggatctgggaatt
 76   F  T  L  R  I  S  R  V  E  A  E  D  L  G  I 271  tattactgctttcaaggttcacatgttcctccgacgttcggtgga
 91   Y  Y  C  F  Q  G  S  H  V  P  P  T  F  G  G 316  ggcaccaaactggaaatcaaacgt
106   G  T  K  L  E  I  K  R
``` v1.2

```
  1  gatgttttgatgacccaaactccactctccctgcctgtcagtctt
  1   D  V  L  M  T  Q  P  L  S  L  P  V  S  L 46  ggagatccagcctccatctcttgcagatctagtcagagcatagta
 16   G  D  P  A  S  I  S  C  R  S  S  Q  S  I  V 91  catagtaatgtaaacacctatttagaatggtacctgcagaaacca
 31   H  S  N  V  N  T  Y  L  E  W  Y  L  Q  K  P 136  ggccagtctccaaggctcctgatctacaaagtttccaaccgattt
 46   G  Q  S  P  R  L  L  I  Y  K  V  S  N  R  F 181  tctggggtcccagacaggttcagtggcagtggagcagggacagat
 61   S  G  V  P  D  R  F  S  G  S  G  A  G  T  D 226  ttcacactcaggatcagcagagtggaggctgaggatctgggaatt
 76   F  T  L  R  I  S  R  V  E  A  E  D  L  G  I 271  tattactgctttcaaggttcacatgttcctccgacgttcggtgga
 91   Y  Y  C  F  Q  G  S  H  V  P  P  T  F  G  G 316  ggcaccaaactggaaatcaaacgt
106   G  T  K  L  E  I  K  R
```

```
  1 gatgttgtgatgacccaaactccactctccctgcctgtcagtctt
  1  D  V  V  M  T  Q  T  P  L  S  L  P  V  S  L 46 ggagatccagcctccatctcttgcagatctagtcagagcatagta
 16  G  D  P  A  S  I  S  C  R  S  S  Q  S  I  V 91 catagtaatgtaaacacctatttagaatggtacctgcagaaacca
 31  H  S  N  V  N  T  Y  L  E  W  Y  L  Q  K  P 136 ggccagtctccaaagctcctgatctacaaagtttccaaccgattt
 46  G  Q  S  P  K  L  L  I  Y  K  V  S  N  R  F 181 tctggggtcccagacaggttcagtggcagtggagcagggacagat
 61  S  G  V  P  D  R  F  S  G  S  G  A  G  T  D 226 ttcacactcaggatcagcagagtggaggctgaggatctgggaatt
 76  F  T  L  R  I  S  R  V  E  A  E  D  L  G  I 271 tattactgctttcaaggttcacatgttcctccgacgttcggtgga
 91  Y  Y  C  F  Q  G  S  H  V  P  P  T  F  G  G 316 ggcaccaaactggaaatcaaacgt
106  G  T  K  L  E  I  K  R
```

Comparison of inhibition of IGF-I-stimulated growth and survival of MCF-7 cells by humanized EM164 v1.0 antibody (6-25 µg/mL) vs murine EM164 antibody (5-10 µg/mL)

ANTI-IGF-I RECEPTOR ANTIBODY

FIELD OF THE INVENTION

The present invention relates to antibodies that bind to human insulin-like growth factor-I receptor (IGF-I receptor). More particularly, the invention relates to anti-IGF-I receptor antibodies that inhibit the cellular functions of the IGF-I receptor. Still more particularly, the invention relates to anti-IGF-I receptor antibodies that antagonize the effects of IGF-I, IGF-II and serum on the growth and survival of tumor cells and which are substantially devoid of agonist activity. The invention also relates to fragments of said antibodies, humanized and resurfaced versions of said antibodies, conjugates of said antibodies, antibody derivatives, and the uses of same in diagnostic, research and therapeutic applications. The invention further relates to improved antibodies or fragments thereof that are made from the above-described antibodies and fragments thereof. In another aspect, the invention relates to a polynucleotide encoding the antibodies or fragments thereof, and to vectors comprising the polynucleotides.

BACKGROUND OF THE INVENTION

Insulin-like growth factor-I receptor (IGF-I receptor) is a transmembrane heterotetrameric protein, which has two extracellular alpha chains and two membrane-spanning beta chains in a disulfide-linked $\beta$-$\alpha$-$\alpha$-$\beta$ configuration. The binding of the ligands, which are insulin-like growth-factor-I (IGF-I) and insulin-like growth factor-II (IGF-II), by the extracellular domain of IGF-I receptor activates its intracellular tyrosine kinase domain resulting in autophosphorylation of the receptor and substrate phosphorylation. The IGF-I receptor is homologous to insulin receptor, having a high sequence similarity of 84% in the beta chain tyrosine kinase domain and a low sequence similarity of 48% in the alpha chain extracellular cysteine rich domain (Ulrich, A. et al., 1986, EMBO, 5, 2503-2512; Fujita-Yamaguchi, Y. et al., 1986, J. Biol. Chem., 261, 16727-16731; LeRoith, D. et al., 1995, Endocrine Reviews, 16, 143-163). The IGF-I receptor and its ligands (IGF-I and IGF-II) play important roles in numerous physiological processes including growth and development during embryogenesis, metabolism, cellular proliferation and cell differentiation in adults (LeRoith, D., 2000, Endocrinology, 141, 1287-1288; LeRoith, D., 1997, New England J. Med., 336, 633-640).

IGF-I and IGF-II function both as endocrine hormones in the blood, where they are predominantly present in complexes with IGF-binding proteins, and as paracrine and autocrine growth factors that are produced locally (Humbel, R. E., 1990, Eur. J. Biochem., 190, 445-462; Cohick, W. S. and Clemmons, D. R., 1993, Annu. Rev. Physiol. 55, 131-153).

The IGF-I receptor has been implicated in promoting growth, transformation and survival of tumor cells (Baserga, R. et al., 1997, Biochem. Biophys. Acta, 1332, F105-F126; Blakesley, V. A. et al., 1997, Journal of Endocrinology, 152, 339-344; Kaleko, M., Rutter, W. J., and Miller, A. D. 1990, Mol. Cell. Biol., 10, 464-473). Thus, several types of tumors are known to express higher than normal levels of IGF-I receptor, including breast cancer, colon cancer, ovarian carcinoma, synovial sarcoma and pancreatic cancer (Khandwala, H. M. et al., 2000, Endocrine Reviews, 21, 215-244; Werner, H. and LeRoith, D., 1996, Adv. Cancer Res., 68,183-223; Happerfield, L. C. et al., 1997, J. Pathol., 183, 412-417; Frier, S. et al., 1999, Gut, 44, 704-708; van Dam, P. A. et al., 1994, J. Clin. Pathol., 47, 914-919; Xie, Y. et al., 1999, Cancer Res., 59, 3588-3591; Bergmann, U. et al., 1995, Cancer Res., 55, 2007-2011). In vitro, IGF-I and IGF-II have been shown to be potent mitogens for several human tumor cell lines such as lung cancer, breast cancer, colon cancer, osteosarcoma and cervical cancer (Ankrapp, D. P. and Bevan, D. R., 1993, Cancer Res., 53, 3399-3404; Cullen, K. J., 1990, Cancer Res., 50, 48-53; Hermanto, U. et al., 2000, Cell Growth & Differentiation, 11, 655-664; Guo, Y. S. et al., 1995, J. Am. Coll. Surg., 181, 145-154; Kappel, C. C. et al., 1994, Cancer Res., 54, 2803-2807; Steller, M. A. et al., 1996, Cancer Res., 56, 1761-1765). Several of these tumors and tumor cell lines also express high levels of IGF-I or IGF-II, which may stimulate their growth in an autocrine or paracrine manner (Quinn, K. A. et al., 1996, J. Biol. Chem., 271, 11477-11483).

Epidemiological studies have shown a correlation of elevated plasma level of IGF-I (and lower level of IGF-binding protein-3) with increased risk for prostate cancer, colon cancer, lung cancer and breast cancer (Chan, J. M. et al., 1998, Science, 279, 563-566; Wolk, A. et al., 1998, J. Natl. Cancer Inst., 90, 911-915; Ma, J. et al., 1999, J. Natl. Cancer Inst., 91, 620-625; Yu, H. et al., 1999, J. Natl. Cancer Inst., 91, 151-156; Hankinson, S. E. et al., 1998, Lancet, 351, 1393-1396). Strategies to lower the IGF-I level in plasma or to inhibit the function of IGF-I receptor have been suggested for cancer prevention (Wu, Y. et al., 2002, Cancer Res., 62, 1030-1035; Grimberg, A and Cohen P., 2000, J. Cell. Physiol., 183, 1-9).

The IGF-I receptor protects tumor cells from apoptosis caused by growth factor deprivation, anchorage independence or cytotoxic drug treatment (Navarro, M. and Baserga, R., 2001, Endocrinology, 142, 1073-1081; Baserga, R. et al., 1997, Biochem. Biophys. Acta, 1332, F105-F126). The domains of IGF-I receptor that are critical for its mitogenic, transforming and anti-apoptotic activities have been identified by mutational analysis.

For example, the tyrosine 1251 residue of IGF-I receptor has been identified as critical for anti-apoptotic and transformation activities but not for its mitogenic activity (O'Connor, R. et al., 1997, Mol. Cell. Biol., 17, 427-435; Miura, M. et al., 1995, J. Biol. Chem., 270, 22639-22644). The intracellular signaling pathway of ligand-activated IGF-I receptor involves phosphorylation of tyrosine residues of insulin receptor substrates (IRS-1 and IRS-2), which recruit phosphatidylinositol-3-kinase (PI-3-kinase) to the membrane. The membrane-bound phospholipid products of PI-3-kinase activate a serine/threonine kinase Akt, whose substrates include the pro-apoptotic protein BAD which is phosphorylated to an inactive state (Datta, S. R., Brunet, A. and Greenberg, M. E., 1999, Genes & Development, 13, 2905-2927; Kulik, G., Klippel, A. and Weber, M. J., 1997, Mol. Cell. Biol. 17, 1595-1606). The mitogenic signaling of IGF-I receptor in MCF-7 human breast cancer cells requires PI-3-kinase and is independent of mitogen-activated protein kinase, whereas the survival signaling in differentiated rat pheochromocytoma PC12 cells requires both PI-3-kinase and mitogen-activated protein kinase pathways (Dufourny, B. et al., 1997, J. Biol. Chem., 272, 31163-31171; Parrizas, M., Saltiel, A. R. and LeRoith, D., 1997, J. Biol. Chem., 272, 154-161).

Down-regulation of IGF-I receptor level by anti-sense strategies has been shown to reduce the tumorigenicity of several tumor cell lines in vivo and in vitro, such as melanoma, lung carcinoma, ovarian cancer, glioblastoma, neuroblastoma and rhabdomyosarcoma (Resnicoff, M. et al., 1994, Cancer Res., 54, 4848-4850; Lee, C.-T. et al., 1996, Cancer Res., 56, 3038-3041; Muller, M. et al., 1998, Int. J. Cancer, 77, 567-571; Trojan, J. et al., 1993, Science, 259, 94-97; Liu, X. et al., 1998, Cancer Res., 58, 5432-5438; Shapiro, D. N. et al., 1994, J. Clin. Invest., 94, 1235-1242). Likewise, a dominant negative mutant of IGF-I receptor has been reported to reduce the tumorigenicity in vivo and growth in vitro of transformed Rat-1 cells over expressing IGF-I receptor (Prager, D. et al., 1994, *Proc. Natl. Acad. Sci. USA,* 91, 2181-2185).

Tumor cells expressing an antisense to the IGF-I receptor mRNA undergo massive apoptosis when injected into animals in biodiffusion chambers. This observation makes the IGF-I receptor an attractive therapeutic target, based upon the hypothesis that tumor cells are more susceptible than normal cells to apoptosis by inhibition of IGF-I receptor (Resnicoff, M. et al., 1995, *Cancer Res.,* 55, 2463-2469; Baserga, R., 1995, *Cancer Res.,* 55, 249-252).

Another strategy to inhibit the function of IGF-I receptor in tumor cells has been to use anti-IGF-I receptor antibodies which bind to the extracellular domains of IGF-I receptor and inhibit its activation. Several attempts have been reported to develop mouse monoclonal antibodies against IGF-I receptor, of which two inhibitory antibodies—IR3 and 1H7—are available and their use has been reported in several IGF-I receptor studies.

The IR3 antibody was developed using a partially purified placental preparation of insulin receptor to immunize mice, which yielded an antibody, IR1, that was selective for binding insulin receptor, and two antibodies, IR2 and IR3, that showed preferential immunoprecipitation of IGF-I receptor (somatomedin-C receptor) but also weak immunoprecipitation of insulin receptor (Kull, F. C. et al., 1983, *J. Biol. Chem.,* 258, 6561-6566).

The 1H7 antibody was developed by immunizing mice with purified placental preparation of IGF-I receptor, which yielded the inhibitory antibody 1H7 in addition to three stimulatory antibodies (Li, S. -L. et al., 1993, *Biochem. Biophys. Res. Commun.,* 196, 92-98; Xiong, L. et al., 1992, *Proc. Natl. Acad. Sci. USA,* 89, 5356-5360).

In another report, a panel of mouse monoclonal antibodies specific for human IGF-I receptor were obtained by immunization of mice with transfected 3T3 cells expressing high levels of IGF-I receptor, which were categorized into seven groups by binding competition studies and by their inhibition or stimulation of IGF-I binding to transfected 3T3 cells (Soos, M. A. et al., 1992, *J. Biol. Chem.,* 267, 12955-12963).

Thus, although IR3 antibody is the most commonly used inhibitory antibody for IGF-I receptor studies in vitro, it suffers from the drawback that it exhibits agonistic activity in transfected 3T3 and CHO cells expressing human IGF-I receptor (Kato, H. et al., 1993, *J. Biol. Chem.,* 268, 2655-2661; Steele-Perkins, G. and Roth, R. A., 1990, *Biochem. Biophys. Res. Commun.,* 171, 1244-1251). Similarly, among the panel of antibodies developed by Soos et al., the most inhibitory antibodies 24-57 and 24-60 also showed agonistic activities in the transfected 3T3 cells (Soos, M. A. et al., 1992, *J. Biol. Chem.,* 267, 12955-12963). Although, IR3 antibody is reported to inhibit the binding of IGF-I (but not IGF-II) to expressed receptors in intact cells and after solubilization, it is shown to inhibit the ability of both IGF-I and IGF-II to stimulate DNA synthesis in cells in vitro (Steele-Perkins, G. and Roth, R. A., 1990, *Biochem. Biophys. Res. Commun.,* 171, 1244-1251). The binding epitope of IR3 antibody has been inferred from chimeric insulin-IGF-I receptor constructs to be the 223-274 region of IGF-I receptor (Gustafson, T. A. and Rutter, W. J., 1990, *J. Biol. Chem.,* 265, 18663-18667; Soos, M. A. et al., 1992, *J. Biol. Chem.,* 267, 12955-12963).

The MCF-7 human breast cancer cell line is typically used as a model cell line to demonstrate the growth response of IGF-I and IGF-II in vitro (Dufourny, B. et al., 1997, *J. Biol. Chem.,* 272, 31163-31171). In MCF-7 cells, the IR3 antibody incompletely blocks the stimulatory effect of exogenously added IGF-I and IGF-II in serum-free conditions by approximately 80%. Also, the IR3 antibody does not significantly inhibit (less than 25%) the growth of MCF-7 cells in 10% serum (Cullen, K. J. et al., 1990, *Cancer Res.,* 50, 48-53). This weak inhibition of serum-stimulated growth of MCF-7 cells by IR3 antibody in vitro may be related to the results of an in vivo study in which IR3 antibody treatment did not significantly inhibit the growth of a MCF-7 xenograft in nude mice (Arteaga, C. L. et al., 1989, *J. Clin. Invest.,* 84, 1418-1423).

Because of the weak agonistic activities of the IR3 and other reported antibodies, and their inability to significantly inhibit the growth of tumor cells such as MCF-7 cells in the more physiological condition of serum-stimulation (instead of stimulation by exogenously added IGF-I or IGF-II in serum-free condition), there is a need for new anti-IGF-I receptor antibodies which significantly inhibit the serum-stimulated growth of tumor cells but which do not show significant agonistic activity by themselves.

SUMMARY OF THE INVENTION

Accordingly, it is an object of the invention to provide antibodies, antibody fragments and antibody derivatives that specifically bind to insulin-like growth factor-I receptor and inhibit the cellular activity of the receptor by antagonizing the receptor, and are also substantially devoid of agonist activity towards the receptor.

Thus, in a first embodiment, there is provided murine antibody EM164, which is fully characterized herein with respect to the amino acid sequences of both its light and heavy chain variable regions, the cDNA sequences of the genes for the light and heavy chain variable regions, the identification of its CDRs (complementarity-determining regions), the identification of its surface amino acids, and means for its expression in recombinant form.

In a second embodiment, there are provided resurfaced or humanized versions of antibody EM164 wherein surface-exposed residues of the antibody or its fragments are replaced in both light and heavy chains to more closely resemble known human antibody surfaces. Such humanized antibodies may have increased utility, compared to murine EM164, as therapeutic or diagnostic agents. Humanized versions of antibody EM164 are also fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form.

In a third embodiment, there is provided an antibody that is capable of inhibiting the growth of a cancer cell by greater than about 80% in the presence of a growth stimulant such as, for example, serum, insulin-like growth factor-I and insulin-like growth factor-II.

In a fourth embodiment, there is provided an antibody or antibody fragment having a heavy chain including CDRs having amino acid sequences represented by SEQ ID NOS: 1-3, respectively:

```
SYWMH,              (SEQ ID NO:1)

EINPSNGRTNYNEKFKR,  (SEQ ID NO:2)

GRPDYYGSSKWYFDV;    (SEQ ID NO:3)
``` and having a light chain that comprises CDRs having amino acid sequences represented by SEQ ID NOS:4-6:

```
RSSQSIVHSNVNTYLE;      (SEQ ID NO:4)

KVSNRFT;               (SEQ ID NO:5)

FQGSHVPPT.             (SEQ ID NO:6)
```

In a fifth embodiment, there are provided antibodies having a heavy chain that has an amino acid sequence that shares at least 90% sequence identity with an amino acid sequence represented by SEQ ID NO:7:

```
                                                  (SEQ ID NO:7)
QVQLQQSGAELVKPGASVKLSCKASGYTFTSYWMHWVKQRPGQGLEWIGE

INPSNGRTNYNEKFKRKATLTVDKSSSTAYMQLSSLTSEDSAVYYFARGR

PDYYGSSKWYFDVWGAGTTVTVSS.
```

Similarly, there are provided antibodies having a light chain that has an amino acid sequence that shares at least 90% sequence identity with an amino acid sequence represented by SEQ ID NO:8:

```
DVLMTQTPLSLPVSLGDQASISCRSSQSIVHSNVNTYLEWYLQKPGQSPKLLIYK     (SEQ ID NO:8)

VSNRFSGVPDRFSGSGSGTDFTLRISRVEAEDLGIYYCFQGSHVPPTFGGGTKLEIKR.
```

In a sixth embodiment, antibodies are provided having a humanized or resurfaced light chain variable region having an amino acid sequence corresponding to one of SEQ ID NOS:-9-12:

```
DVVMTQTPLSLPVSLGDPASISCRSSQSIVHSNVNTYLEWYLQKPGQSPRLLIYKV    (SEQ ID NO:9)

SNRFSGVPDRFSGSGAGTDFTLRISRVEAEDLGIYYCFQGSHVPPTFGGGTKLEIK

R;

DVLMTQTPLSLPVSLGDPASISCRSSQSIVHSNVNTYLEWYLQKPGQSPKLLIYKV    (SEQ ID NO:10)

SNRFSGVPDRESGSGAGTDFTLRISRVEAEDLGIYYCFQGSHVPPTFGGGTKLEIK

R;

DVLMTQTPLSLPVSLGDPASISCRSSQSIVHSNVNTYLEWYLQKPGQSPRLLIYKV    (SEQ ID NO:11)

SNRFSGVPDRFSGSGAGTDFTLRISRVEAEDLGIYYCFQGSHVPPTFGGGTKLEIK

R; or

DVVMTQTPLSLPVSLGDPASISCRSSQSIVHSNVNTYLEWYLQKPGQSPKLLIYK     (SEQ ID NO:12)

VSNRFSGVPDRFSGSGAGTDFTLRISRVEAEDLGIYYCFQGSHVPPTFGGGTKLEI

KR.
```

Similarly, antibodies are provided having a humanized or resurfaced heavy chain variable region having an amino acid sequence corresponding to SEQ ID NO:13:

```
QVQLVQSGAEVVKPGASVKLSCKASGYTFTSYWMHWVKQRPGQGLEWIGEINP    (SEQ ID NO:13)

SNGRTNYNQKFQGKATLTVDKSSSTAYMQLSSLTSEDSAVYYFARGRPDYYGSS

KWYFDVWGQGTTVTVSS.
```

In a seventh embodiment, antibodies or antibody fragments of the present invention are provided that have improved properties. For example, antibodies or antibody fragments having improved affinity for IGF-I-receptor are prepared by affinity maturation of an antibody or fragment of the present invention.

The present invention further provides conjugates of said antibodies, wherein a cytotoxic agent is covalently attached, directly or via a cleavable or non-cleavable linker, to an antibody or epitope-binding fragment of an antibody of the present invention. In preferred embodiments, the cytotoxic agent is a taxol, a maytansinoid, CC-1065 or a CC-1065 analog.

The present invention further provides for antibodies or fragments thereof that are further labeled for use in research or diagnostic applications. In preferred embodiments, the label is a radiolabel, a fluorophore, a chromophore, an imaging agent or a metal ion.

A method for diagnosis is also provided in which said labeled antibodies or fragments are administered to a subject suspected of having a cancer, and the distribution of the label within the body of the subject is measured or monitored.

In a eighth embodiment, the invention provides methods for the treatment of a subject having a cancer by administering an antibody, antibody fragment or antibody conjugate of the present invention, either alone or in combination with other cytotoxic or therapeutic agents. The cancer can be one or more of, for example, breast cancer, colon cancer, ovarian carcinoma, osteosarcoma, cervical cancer, prostate cancer, lung cancer, synovial carcinoma, pancreatic cancer, or other cancer yet to be determined in which IGF-I receptor levels are elevated.

BRIEF DESCRIPTION OF THE FIGURES

FIG. 1 shows fluorescence activated cell sorting (FACS) analysis of the specific binding of purified EM164 antibody to cells over expressing human Y1251F IGF-I receptor or human insulin receptor.

FIG. 12 shows the cDNA (SEQ ID NO:49) and amino acid sequences (SEQ ID NO:50) of the light chain leader and variable region of the murine anti-IGF-I receptor antibody EM164. The arrow marks the start of framework 1. The 3 CDR sequences according to Kabat are underlined.

FIG. 13 shows the cDNA (SEQ ID NO:51) and amino acid sequences (SEQ ID NO:52) of the heavy chain leader and variable region for the murine anti-IGF-I receptor antibody EM164. The arrow marks the start of framework 1. The 3 CDR sequences according to Kabat are underlined.

FIG. 14 shows the light and heavy chain CDR amino acid sequences of antibody EM164 as determined from Chothia canonical class definitions. AbM modeling software definitions for the heavy chain CDRs are also shown. EM164 as determined from Chothia canonical class definitions. AbM modeling software definitions for the heavy chain CDRs are also shown. Light Chain: CDR1 is SEQ ID NO:4, CDR2 is SEQ ID NO:5, and CDR3 is SEQ ID NO:6. Heavy Chain: CDR1 is SEQ ID NO:1, CDR2 is SEQ ID NO:2, and CDR3 is SEQ ID NO:3. AbM Heavy Chain: CDR1 is SEQ ID NO:53, CDR2 is SEQ ID NO:54, and CDR3 is SEQ ID NO:55.

FIG. 15 shows the light chain and heavy chain amino acid sequences for anti-IGF-I-receptor antibody EM164 aligned with the germline sequences for the Cr1 (SEQ ID NO:56) and J558.c genes (SEQ ID NO:57)genes. Dashes (-) indicate sequence identity.

FIG. 18 shows the 10 most homologous amino acid sequences of the heavy chains screened from the 127 antibodies in the set of structure files used to predict the surface residues of EM164. em164 HC (SEQ ID NO:70), 1nqb (SEQ ID NO:71), 1ngp (SEQ ID NO:72), 1fbi (SEQ ID NO:73), 1afv (SEQ ID NO:74), 1yuh (SEQ ID NO:75), 1plg (SEQ ID NO:76), 1d5b (SEQ ID NO:77), 1ae6 (SEQ ID NO:78), 1axs (SEQ ID NO:79), 3hfl (SEQ ID NO:80), Consensus (SEQ ID NO:81).

FIG. 19 shows the average accessibility for each of the (A) light, and (B) heavy chain variable region residues from the 10 most homologous structures. The numbers represent the Kabat antibody sequence position numbers.

FIG. 20 shows the light chain variable region amino acid sequences for murine EM164 (muEM164) and humanized EM164 (huEM164) antibodies. muEM164 (SEQ ID NO:82), huEM164 V1.0 (SEQ ID NO:83), huEM164 V1.1 (SEQ ID NO:84), huEM164 V1.2 (SEQ ID NO:85), huEM164 V1.3 (SEQ ID NO:86).

FIG. 21 shows the heavy chain variable region amino acid sequences for murine (muEM164, SEQ ID NO:87)and humanized EM164 antibodies (huEM164, SEQ ID NO:88).

FIG. 22 shows the huEM164 v1.0 variable region DNA and amino acid sequences. for both the light (DNA, SEQ ID NO:89, amino acid SEQ ID NO:90) and heavy chains (DNA, SEQ ID NO:91, amino acid SEQ ID NO:92).

FIG. 23 shows the light chain variable region DNA and amino acid sequences for humanized EM164 v1.1 (DNA, SEQ ID NO:93; amino acid SEQ ID NO:94), v1.2 (DNA, SEQ ID NO:95; amino acid SEQ ID NO:96) and v1.3 (DNA, SEQ ID NO:97; amino acid SEQ ID NO:98).

DETAILED DESCRIPTION OF THE INVENTION

Figure 2:
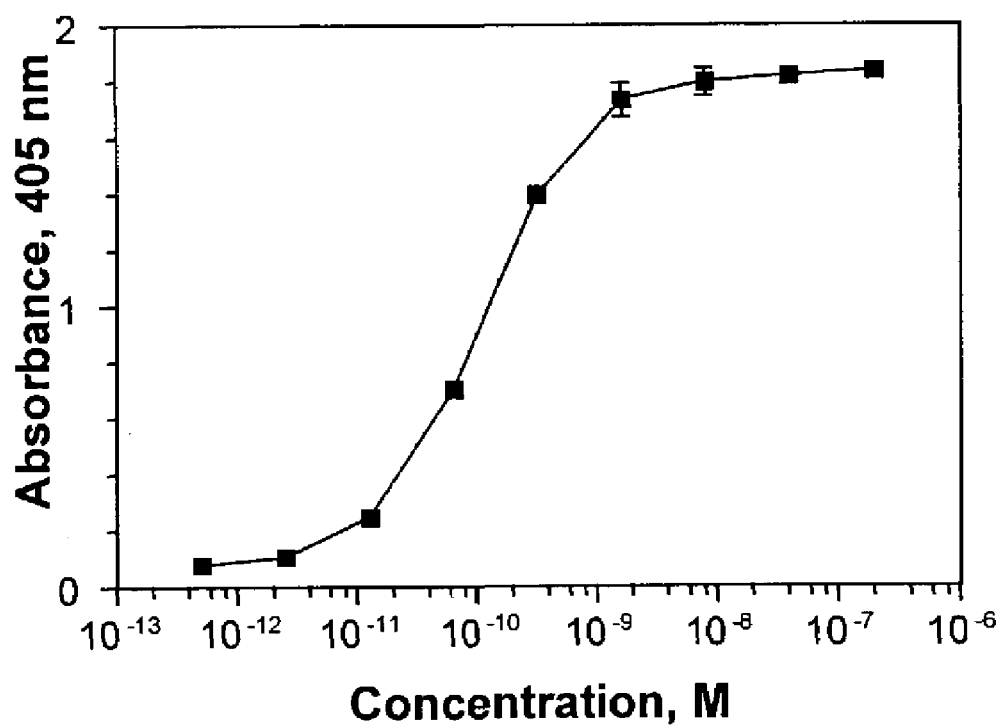
FIG. 2 shows a binding titration curve for the binding of EM164 antibody to biotinylated human IGF-I receptor.

The present inventors have discovered and improved novel antibodies that specifically bind to the human insulin-like growth factor-I receptor (IGF-IR) on the cell surface. The antibodies and fragments have the unique ability to inhibit the cellular functions of the receptor without the capacity to activate the receptor themselves. Thus, while previously known antibodies that specifically bind and inhibit IGF-IR also activate the receptor even in the absence of IGF-IR ligands, the antibodies or fragments of the present invention antagonize IGF-IR but are substantially devoid of agonist activity. Furthermore, the antibodies and antibody fragments of the present invention inhibit the growth of human tumor cells such as MCF-7 cells in the presence of serum by greater than 80%, which is a higher degree of inhibition than is obtained using previously known anti-IGF-IR antibodies.

The present invention proceeds from a murine anti-IGF-IR antibody, herein EM164, that is fully characterized with respect to the amino acid sequences of both light and heavy chains, the identification of the CDRs, the identification of surface amino acids, and means for its expression in recombinant form.

The germline sequences are shown in FIG. 15 aligned with the sequence of EM164. The comparison identifies probable somatic mutations in EM164, including one each in CDR1 in the light chain and in CDR2 in the heavy chain.

The primary amino acid and DNA sequences of antibody EM164 light and heavy chains, and of humanized versions, are disclosed herein. However, the scope of the present invention is not limited to antibodies and fragments comprising these sequences. Instead, all antibodies and fragments that specifically bind to an insulin-like growth factor-I receptor and antagonize the biological activity of the receptor, but which are substantially devoid of agonist activity, fall within the scope of the present invention. Thus, antibodies and antibody fragments may differ from antibody EM164 or the humanized derivatives in the amino acid sequences of their scaffold, CDRs, light chain and heavy chain, and still fall within the scope of the present invention.

The CDRs of antibody EM164 are identified by modeling and their molecular structures have been predicted. Again, while the CDRs are important for epitope recognition, they are not essential to the antibodies and fragments of the invention. Accordingly, antibodies and fragments are provided that have improved properties produced by, for example, affinity maturation of an antibody of the present invention.

Diverse antibodies and antibody fragments, as well as antibody mimics may be readily produced by mutation, deletion and/or insertion within the variable and constant region sequences that flank a particular set of CDRs. Thus, for example, different classes of Ab are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework. The term "variable" is used herein to describe certain portions of the variable domains that differ in sequence among antibodies and are used in the binding and specificity of each particular antibody for its antigen. However, the variability is not usually evenly distributed through the variable domains of the antibodies. It is typically concentrated in three segments called complementarity determining regions (CDRs) or hypervariable regions both in the light chain and the heavy chain variable domains. The more highly conserved portions of the variable domains are called the framework (FR). The variable domains of heavy and light chains each comprise four framework regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen binding site of antibodies (E. A. Kabat et al. *Sequences of Proteins of Immunological Interest*, fifth edition, 1991, NIH). The constant domains are not involved directly in binding an antibody to an antigen, but exhibit various effector functions, such as participation of the antibody in antibody-dependent cellular toxicity.

Humanized antibodies, or antibodies adapted for non-rejection by other mammals, may be produced using several technologies such as resurfacing and CDR grafting. In the resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host, are disclosed in U.S. Pat. No. 5,639,641, which is hereby incorporated in its entirety by reference. In the CDR grafting technology, the murine heavy and light chain CDRs are grafted into a fully human framework sequence.

The invention also includes functional equivalents of the antibodies described in this specification. Functional equivalents have binding characteristics that are comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424, which are incorporated in their respective entireties by reference.

Functional equivalents include polypeptides with amino acid sequences substantially the same as the amino acid sequence of the variable or hypervariable regions of the antibodies of the invention. "Substantially the same" as applied to an amino acid sequence is defined herein as a sequence with at least about 90%, and more preferably at least about 95% sequence identity to another amino acid sequence, as determined by the FASTA search method in accordance with Pearson and Lipman, Proc. Natl. Acad. Sci. USA 85, 2444-2448 (1988).

Chimerized antibodies preferably have constant regions derived substantially or exclusively from human antibody constant regions and variable regions derived substantially or exclusively from the sequence of the variable region from a mammal other than a human. Humanized forms of the antibodies are made by substituting the complementarity determining regions of, for example, a mouse antibody, into a human framework domain, e.g., see PCT Pub. No. W092/22653. Humanized antibodies preferably have constant regions and variable regions other than the complementarity determining regions (CDRs) derived substantially or exclusively from the corresponding human antibody regions and CDRs derived substantially or exclusively from a mammal other than a human.

Functional equivalents also include single-chain antibody fragments, also known as single-chain antibodies (scFvs). These fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the ($V_L$) and ($V_H$) domains occurs once they are linked so as to maintain the target molecule binding-specificity of the whole antibody from which the single-chain antibody fragment is derived. Generally, the carboxyl terminus of the ($V_L$) or ($V_H$) sequence may be covalently linked by such a peptide linker to the amino acid terminus of a complementary ($V_L$) and ($V_H$) sequence. Single-chain antibody fragments may be generated by molecular cloning, antibody phage display library or similar techniques. These proteins may be produced either in eukaryotic cells or prokaryotic cells, including bacteria.

Single-chain antibody fragments contain amino acid sequences having at least one of the variable or complementarity determining regions (CDRs) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Functional equivalents further include fragments of antibodies that have the same, or comparable binding characteristics to those of the whole antibody. Such fragments may contain one or both Fab fragments or the F(ab')$_2$ fragment. Preferably the antibody fragments contain all six complementarity determining regions of the whole antibody, although fragments containing fewer than all of such regions, such as three, four or five CDRs, are also functional. Further, the functional equivalents may be or may combine members of any one of the following immunoglobulin classes: IgG, IgM, IgA, IgD, or IgE, and the subclasses thereof.

The knowledge of the amino acid and nucleic acid sequences for the anti-IGF-I receptor antibody EM164 and its humanized variants, which are described herein, can be used to develop other antibodies which also bind to human IGF-I receptor and inhibit the cellular functions of the IGF-I receptor. Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.*, 254, 392-403; Rader, C. et al., 1998, *Proc. Natl. Acad. Sci. USA*, 95, 8910-8915; Vaughan, T. J. et al., 1998, *Nature Biotechnology*, 16, 535-539).

In these studies, variants of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16, 535-539; Adey, N. B. et al., 1996, Chapter 16, pp. 277-291, in *"Phage Display of Peptides and Proteins"*, Eds. Kay, B. K. et al., Academic Press). These methods of changing the sequence of the primary antibody have resulted in improved affinities of the secondary antibodies (Gram, H. et al., 1992, *Proc. Natl. Acad. Sci. USA*, 89, 3576-3580; Boder, E. T. et al., 2000, *Proc. Natl. Acad. Sci. USA*, 97, 10701-10705; Davies, J. and Riechmann, L., 1996, *Immunotechnolgy*, 2, 169-179; Thompson, J. et al., 1996, *J. Mol. Biol.*, 256, 77-88; Short, M. K. et al., 2002, *J. Biol. Chem.*, 277, 16365-16370; Furukawa, K. et al., 2001, *J. Biol. Chem.*, 276, 27622-27628).

By a similar directed strategy of changing one or more amino acid residues of the antibody, the antibody sequences described in this invention can be used to develop anti-IGF-I receptor antibodies with improved functions.

The conjugates of the present invention comprise the antibody, fragments, and their analogs as disclosed herein, linked to a cytotoxic agent. Preferred cytotoxic agents are maytansinoids, taxanes and analogs of CC-1065. The conjugates can be prepared by in vitro methods. In order to link the cytotoxic agent to the antibody, a linking group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the cytotoxic agent.

Maytansinoids and maytansinoid analogs are among the preferred cytotoxic agents. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Taxanes are also preferred cytotoxic agents. Taxanes suitable for use in the present invention are disclosed in U.S. Pat. Nos. 6,372,738 and 6,340,701.

CC-1065 and its analogs are also preferred cytotoxic drugs for use in the present invention. CC-1065 and its analogs are disclosed in U.S. Pat. Nos. 6,372,738; 6,340,701; 5,846,545 and 5,585,499.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., *Cancer Res.*, 42, 3532-3537 (1982)).

Cytotoxic drugs such as methotrexate, daunorubicin, doxorubicin, vincristine, vinblastine, melphalan, mitomycin C, chlorambucil, and calicheamicin are also suitable for the preparation of conjugates of the present invention, and the drug molecules can also be linked to the antibody molecules through an intermediary carrier molecule such as serum albumin.

For diagnostic applications, the antibodies of the present invention typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{131}$I; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention can be employed in any known assay method, such as competitive binding assays, direct and indirect sandwich assays, and immunoprecipitation assays (Zola, Monoclonal Antibodies: A Manual of Techniques, pp.147-158 (CRC Press, Inc., 1987)).

The antibodies of the invention also are useful for in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies. The antibody may be labeled with any moiety that is detectable in a host, whether by nuclear magnetic resonance, radiology, or other detection means known in the art.

The antibodies of the invention also are useful as affinity purification agents. In this process, the antibodies are immobilized on a suitable support, such a Sephadex resin or filter paper, using methods well known in the art.

The antibodies of the invention also are useful as reagents in biological research, based on their inhibition of the function of IGF-I receptor in cells.

For therapeutic applications, the antibodies or conjugates of the invention are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The antibody may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The method of the present invention can be practiced in vitro, in vivo, or ex vivo.

In other therapeutic treatments, the antibodies, antibody fragments or conjugates of the invention are co-administered with one or more additional therapeutic agents. Suitable therapeutic agents include, but are not limited to, cytotoxic or cytostatic agents. Taxol is a preferred therapeutic agent that is also a cytotoxic agent.

Cancer therapeutic agents are those agents that seek to kill or limit the growth of cancer cells while doing minimal damage to the host. Thus, such agents may exploit any difference in cancer cell properties (e.g. metabolism, vascularization or cell-surface antigen presentation) from healthy host cells. Differences in tumor morphology are potential sites for intervention: for example, the second therapeutic can be an antibody such as an anti-VEGF antibody that is useful in retarding the vascularization of the interior of a solid tumor, thereby slowing its growth rate. Other therapeutic agents include, but are not limited to, adjuncts such as granisetron HCL, androgen inhibitors such as leuprolide acetate, antibiotics such as doxorubicin, antiestrogens such as tamoxifen, antimetabolites such as interferon alpha-2a, cytotoxic agents such as taxol, enzyme inhibitors such as ras farnesyl-transferase inhibitor, immunomodulators such as aldesleukin, and nitrogen mustard derivatives such as melphalan HCl, and the like.

When present in an aqueous dosage form, rather than being lyophilized, the antibody typically will be formulated at a concentration of about 0.1 mg/ml to 100 mg/ml, although wide variation outside of these ranges is permitted. For the treatment of disease, the appropriate dosage of antibody or conjugate will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded.

EXAMPLES

The invention is now described by reference to the following examples, which are illustrative only, and are not intended to limit the present invention.

Example 1

Murine EM164 Antibody

In this first example, the complete primary amino acid structure and cDNA sequence of a murine antibody of the present invention is disclosed, together with its binding properties and means for its expression in recombinant form. Accordingly, there is provided a full and complete disclosure of an antibody of the invention and its preparation, such that one of ordinary skill in the immunological arts would be able to prepare said antibody without undue experimentation.

A. Generation of Anti-IGF-I Receptor Monoclonal Antibody Hybridoma

A cell line expressing human IGF-I receptor with a Y1251F mutation was used for immunization as it expressed a high number of IGF-I receptors ($\sim 10^7$ per cell). The Y1251F-mutation in the cytoplasmic domain of IGF-I receptor resulted in loss of transformation and anti-apoptotic signaling, but did not affect IGF-I binding and IGF-I-stimulated mitogenic signaling (O'Connor, R. et al., 1997, *Mol. Cell. Biol.*, 17, 427-435; Miura, M. et al., 1995, *J. Biol. Chem.*, 270, 22639-22644). The mutation did not otherwise affect antibody generation because the antibody of this example bound to the extracellular domain of IGF-I receptor, which was identical for both the Y1251F mutant and the wild type receptor.

A cell line expressing human IGF-I receptor with a Y1251F mutation was generated from 3T3-like cells of a IGF-I-receptor-deficient mouse by transfection with Y1251F-mutant human IGF-I-receptor gene together with a puromycin-resistance gene, and was selected using puromycin (2.5 microgram/mL) and by FACS sorting for high IGF-I receptor expression (Miura, M. et al., 1995, *J. Biol. Chem.*, 270, 22639-22644). A cell line having a high level of IGF-I receptor expression was further selected using a high concentration of puromycin such as 25 microgram/mL, which was toxic to most of the cells. Surviving colonies were picked and those displaying a high level of IGF-I receptor expression were selected.

CAF1/J female mice, 6 months old, were immunized intraperitoneally on day 0 with Y1251F-mutant-human-IGF-I-receptor-over expressing cells ($5 \times 10^5$ cells, suspended in 0.2 mL PBS). The animals were boosted with 0.2 mL cell suspension as follows: day 2, $1 \times 10^6$ cells; day 5, $2 \times 10^6$ cells; days 7, 9, 12, and 23, $1 \times 10^7$ cells. On day 26, a mouse was sacrificed and its spleen removed.

The spleen was ground between two frosted glass slides to obtain a single cell suspension, which was washed with serum-free RPMI medium containing penicillin and streptomycin (SFM). The spleen cell pellet was resuspended in 10 mL of 0.83% (w/v) ammonium chloride solution in water for 10 min on ice to lyse the red blood cells, and was then washed with serum-free medium (SFM). Spleen cells ($1.2 \times 10^8$) were pooled with myeloma cells ($4 \times 10^7$) from the non-secreting mouse myeloma cell line P3X63Ag8.653 (ATCC, Rockville, Md.; Cat. # CRL1580) in a tube, and washed with the serum-free RPMI-1640 medium (SFM). The supernatant was removed and the cell pellet resuspended in the residual medium. The tube was placed in a beaker of water at 37° C. and 1.5 mL of polyethylene glycol solution (50% PEG (w/v), average molecular weight 1500 in 75 mM HEPES, pH 8) was added slowly at a drop rate of 0.5 mL/minute while the tube was gently shaken. After a wait of one minute, 10 mL of SFM was added as follows: 1 mL over the first minute, 2 mL over the second minute, and 7 mL over the third minute. Another 10 mL was then added slowly over one minute. Cells were pelleted by centrifugation, washed in SFM and resuspended in RPMI-1640 growth medium supplemented with 5% fetal bovine serum (FBS), hypoxanthine/aminopterin/ thymidine (HAT), penicillin, streptomycin, and 10% hybridoma cloning supplement (HCS). Cells were seeded into 96-well flat-bottom tissue culture plates at $2 \times 10^5$ spleen cells in 200 μL per well. After 5-7 days, 100 μL per well were removed and replaced with growth medium supplemented with hypoxanthine/thymidine (HT) and 5% FBS. The general conditions used for immunization and hybridoma production were as described by J. Langone and H. Vunakis (Eds., Methods in Enzymology, Vol. 121, "Immunochemical Techniques, Part I"; 1986; Academic Press, Florida) and E. Harlow and D. Lane ("Antibodies: A Laboratory Manual"; 1988; Cold Spring Harbor Laboratory Press, New York). Other techniques of immunization and hybridoma production can also be used, as are well known to those of skill in the art.

Culture supernatants from hybridoma clones were screened for binding to purified human IGF-I receptor by ELISA, for specific binding to cells over expressing human IGF-I receptor, and for a lack of binding to cells over expressing human insulin receptor by ELISA and FACS screening as described below. Clones exhibiting higher binding affinity to cells over expressing human IGF-I receptor than to cells over expressing human insulin receptor were expanded and subcloned. The culture supernatants of the subclones were further screened by the above binding assays. By this procedure, subclone 3F1-C8-D7 (EM164) was selected, and the heavy and light chain genes were cloned and sequenced as described below.

Human IGF-I receptor was isolated for use in the screening of supernatants from hybridoma clones for their binding to IGF-I receptor by the method below. Biotinylated IGF-I was prepared by modification of recombinant IGF-I using biotinylating reagents such as sulfo-NHS-LC-biotin, sulfo-NHS-SS-biotin, or NHS-PEO$_4$-biotin. Biotinylated IGF-I was absorbed on streptavidin-agarose beads and incubated with lysate from cells that over expressed human wild type or Y1251F mutant IGFR. The beads were washed and eluted with a buffer containing 2 to 4 M urea and detergent such as triton X-100 or octyl-β-glucoside. Eluted IGF-I receptor was dialyzed against PBS and was analyzed for purity by SDS-PAGE under reducing conditions, which showed alpha and beta chain bands of IGF-I receptor of molecular weights about 135 kDa and 95 kDa, respectively.

To check for the binding of hybridoma supernatants to purified IGF-I receptor, an Immulon-4HB ELISA plate (Dynatech) was coated with a purified human IGF-I receptor sample (prepared by dialysis from urea/octyl-β-glucoside elution of affinity purified sample) diluted in 50 mM CHES buffer at pH 9.5 (100 μL; 4° C., overnight). The wells were blocked with 200 μL of blocking buffer (10 mg/mL BSA in TBS-T buffer containing 50 mM Tris, 150 mM NaCl, pH 7.5, and 0.1% tween-20) and incubated with supernatants from hybridoma clones (100 μL; diluted in blocking buffer) for about 1 h to 12 h, washed with TBS-T buffer, and incubated with goat-anti-mouse-IgG-Fc-antibody-horseradish peroxidase (HRP) conjugate (100 μL; 0.8 μg/mL in blocking buffer; Jackson ImmunoResearch Laboratories), followed by washes and detection using ABTS/H$_2$O$_2$ substrate at 405 nm (0.5 mg/mL ABTS, 0.03% H$_2$O$_2$ in 0.1 M citrate buffer, pH 4.2). Typically, a supernatant from a 3F1 hybridoma subclone yielded a signal of about 1.2 absorbance units within 3 min of development, in contrast to values of 0.0 obtained for supernatants from some other hybridoma clones. General conditions for this ELISA were similar to the standard ELISA conditions for antibody binding and detection as described by E. Harlow and D. Lane ("Using Antibodies: A Laboratory Manual"; 1999, Cold Spring Harbor Laboratory Press, New York), which conditions can also be used.

Screening of hybridoma supernatants for specific binding to human IGF-I receptor and not to human insulin receptor was performed using ELISA on cell lines that over expressed human Y1251F-IGF-I receptor and on cell lines that over expressed human insulin receptor. Both cell lines were generated from 3T3-like cells of IGF-I receptor deficient mice. The IGF-I receptor over expressing cells and insulin receptor over expressing cells were separately harvested from tissue culture flasks by quick trypsin/EDTA treatment, suspended in growth medium containing 10% FBS, pelleted by centrifugation, and washed with PBS. The washed cells (100 μL of about $1-3 \times 10^6$ cells/mL) were added to wells of an Immulon-2HB plate coated with phytohemagglutinin (100 μL of 20 μg/mL PHA), centrifuged and allowed to adhere to PHA-coated wells for 10 min. The plate with cells was flicked to remove PBS and was then dried overnight at 37° C. The wells were blocked with 5 mg/mL BSA solution in PBS for 1 h at 37° C. and were then washed gently with PBS. Aliquots of the supernatants from hybridoma clones (100 μL; diluted in blocking buffer) were then added to wells containing IGF-I-receptor-overexpressing cells and to wells containing insulin receptor-over expressing cells and were incubated at ambient temperature for 1 h. The wells were washed with PBS, incubated with goat-anti-mouse-IgG-Fc-antibody-horseradish peroxidase conjugate (100 μL; 0.8 μg/mL in blocking buffer) for 1 h, followed by washes and then binding was detected using an ABTS/H$_2$O$_2$ substrate. A typical supernatant from a 3F1 hybridoma subclone upon incubation with cells over expressing IGF-I receptor yielded a signal of 0.88 absorbance units within 12 min of development, in contrast to a value of 0.22 absorbance units obtained upon incubation with cells over expressing human insulin receptor.

The hybridoma was grown in Integra CL 350 flasks (Integra Biosciences, Maryland), according to manufacturer's specifications, to provide purified EM164 antibody. A yield of about 0.5-1 mg/mL antibody was obtained in the harvested supernatants from the Integra flasks, based on quantitation by ELISA and by SDS-PAGE/Coomassie blue staining using antibody standards. The antibody was purified by affinity chromatography on Protein A-agarose bead column under standard purification conditions of loading and washing in 100 mM Tris buffer, pH 8.9, containing 3 M NaCl, followed by elution in 100 mM acetic acid solution containing 150 mM NaCl. The eluted fractions containing antibody were neutralized with cold 2 M K$_2$HPO$_4$ solution and dialyzed in PBS at 4° C. The concentration of the antibody was determined by measuring absorbance at 280 nm (extinction coefficient=1.4 mg$^{-1}$ mL cm$^{-1}$). The purified antibody sample was analyzed by SDS-PAGE under reducing conditions and Coomassie blue staining, which indicated only heavy and light chain bands of antibody at about 55 kDa and 25 kDa, respectively. The isotype of the purified antibody was IgG, with kappa light chain.

B. Binding Characterization of EM164 Antibody

The specific binding of the purified EM 164 antibody was demonstrated by fluorescence activated cell sorting (FACS) using cells over expressing human IGF-I receptor and by using cells that over expressed human insulin receptor (FIG. 1). Incubation of EM 164 antibody (50-100 nM) in 100 μL cold FACS buffer (1 mg/mL BSA in Dulbecco's MEM medium) was performed using cells over expressing IGF-I receptor and using cells over expressing insulin receptor ($2 \times 10^5$ cells/mL) in a round-bottom 96-well plate for 1 h. The cells were pelleted by centrifugation and washed with cold FACS buffer by gentle flicking, followed by incubation with goat-anti-mouse-IgG-antibody-FITC conjugate (100 μL; 10 μg/mL in FACS buffer) on ice for 1 h. The cells were pelleted, washed, and resuspended in 120 μL of 1% formaldehyde solution in PBS. The plate was analyzed using a FACSCalibur reader (BD Biosciences).

A strong fluorescence shift was obtained upon incubation of IGF-I receptor over expressing cells with EM 164 antibody, in contrast to an insignificant shift upon incubation of insulin receptor over expressing cells with EM 164 antibody (FIG. 1), which demonstrated that the EM 164 antibody was selective in its binding to IGF-I receptor and did not bind to insulin receptor. The control antibodies, anti-IGF-I receptor antibody 1H7 (Santa Cruz Biotechnology) and anti-insulin receptor alpha antibody (BD Pharmingen Laboratories), yielded fluorescence shifts upon incubations with cells that over expressed IGF-I receptor and insulin receptor, respectively (FIG. 1). A strong fluorescence shift was also observed by FACS assay using EM 164 antibody and human breast cancer MCF-7 cells, which expressed IGF-I receptor (Dufourny, B. et al., 1997, *J. Biol. Chem.*, 272, 31163-31171), which showed that EM164 antibody bound to human IGF-I receptor on the surface of human tumor cells.

The dissociation constant ($K_d$) for the binding of EM164 antibody with human IGF-I receptor was determined by ELISA titration of the binding of antibody at several concentrations with either directly coated IGF-I receptor (affinity purified using biotinylated IGF-I, as above) or indirectly captured biotinylated IGF-I receptor. Biotinylated IGF-I receptor was prepared by biotinylation of detergent-solubilized lysate from IGF-I receptor over expressing cells using PEO-maleimide-biotin reagent (Pierce, Molecular Biosciences), which was affinity purified using an anti-IGF-I receptor beta chain antibody immobilized on NHS-agarose beads and was eluted with 2-4 M urea in buffer containing NP-40 detergent and dialyzed in PBS.

The $K_d$ determination for the binding of EM164 antibody with biotinylated IGF-I receptor was carried out by coating Immulon-2HB plates with 100 μL of 1 μg/mL streptavidin in carbonate buffer (150 mM sodium carbonate, 350 mM sodium bicarbonate) at 4° C. overnight. The streptavidin-coated wells were blocked with 200 μL of blocking buffer (10 mg/mL BSA in TBS-T buffer), washed with TBS-T buffer and incubated with biotinylated IGF-I receptor (10 to 100 ng) for 4 h at ambient temperature. The wells containing indirectly captured biotinylated IGF-I receptor were then washed and incubated with EM164 antibody in blocking buffer at several concentrations ($5.1 \times 10^{-13}$ M to 200 nM) for 2 h at ambient temperature and were then incubated overnight at 4° C. The wells were next washed with TBS-T buffer and incubated with goat-anti-mouse-IgG$_{H+L}$-antibody-horseradish peroxidase conjugate (100 μL; 0.5 μg/mL in blocking buffer), followed by washes and detection using ABTS/H$_2$O$_2$ substrate at 405 nm. The value of $K_d$ was estimated by non-linear regression for one-site binding.

A similar binding titration was carried out using the Fab fragment of EM164 antibody, prepared by papain digestion of the antibody as described by E. Harlow and D. Lane ("Using Antibodies: A Laboratory Manual"; 1999, Cold Spring Harbor Laboratory Press, New York).

The binding titration curve for the binding of EM164 antibody to biotinylated human IGF-I receptor yielded a $K_d$ value of 0.1 nM (FIG. 2). The Fab fragment of EM164 antibody also bound the human IGF-I receptor very tightly with a $K_d$ value of 0.3 nM, which indicated that the monomeric binding of the EM164 antibody to IGF-I receptor was also very strong.

This extremely low value of dissociation constant for the binding of IGF-I receptor by EM164 antibody was in part due to a very slow $k_{off}$ rate as verified by the strong binding signals observed after prolonged 1-2 day washes of the antibody bound to immobilized IGF-I receptor.

EM164 antibody can be used for immunoprecipitation of IGF-I receptor, as demonstrated by incubation of detergent-solubilized lysate of the human breast cancer MCF-7 cells with EM164 antibody immobilized on protein G-agarose beads (Pierce Chemical Company). A Western blot of the EM164 antibody immunoprecipitate was detected using a rabbit polyclonal anti-IGF-I receptor beta chain (C-terminus) antibody (Santa Cruz Biotechnology) and a goat-anti-rabbit-IgG-antibody-horseradish peroxidase conjugate, followed by washes and enhanced chemiluminescence (ECL) detection. The Western blot of EM164 immunoprecipitate from MCF-7 cells exhibited bands corresponding to the beta chain of IGF-I receptor at about 95 kDa and the pro-IGF-I receptor at about 220 kDa. Similar immunoprecipitations were carried out for other cell types to check species specificity of the binding of EM164 antibody, which also bound to IGF-I receptor from cos-7 cells (African green monkey), but did not bind to IGF-I receptor of 3T3 cells (mouse), CHO cells (chinese hamster) or goat fibroblast cells (goat). The EM164 antibody did not detect SDS-denatured human IGF-I receptor in Western blots of lysates from MCF-7 cells, which indicated that it bound to a conformational epitope of native, non-denatured human IGF-I receptor.

The binding domain of EM164 antibody was further characterized using a truncated alpha chain construct, which comprised the cysteine rich domain flanked by L1 and L2 domains (residues 1-468) fused with the 16-mer-C-terminus piece (residues 704-719) and which was terminated by a C-terminus epitope tag. This smaller IGF-I receptor, which lacked residues 469-703, has been reported to bind IGF-I, although less tightly compared to the native full-length IGF-I receptor (Molina, L. et al., 2000, *FEBS Letters*, 467, 226-230; Kristensen, C. et al., 1999, *J. Biol. Chem.*, 274, 37251-37356). Thus, a truncated IGF-I receptor alpha chain construct was prepared comprising residues 1-468 fused to the C-terminus piece that is residues 704-719 and flanked by a C-terminus myc epitope tag. A stable cell line which expressed this construct, and which also expresses the construct transiently in human embryonic kidney 293T cells, was constructed. A strong binding of EM164 antibody to this truncated IGF-I receptor alpha chain construct was observed. Of the two antibodies tested, IR3 (Calbiochem) also bound to this truncated alpha chain, but 1H7 antibody (Santa Cruz Biotechnology) did not bind, which indicated that the epitope of EM164 antibody was clearly distinct from that of 1H7 antibody.

C. Inhibition of Binding of IGF-I to MCF-7 Cells by EM164 Antibody

Figure 3:
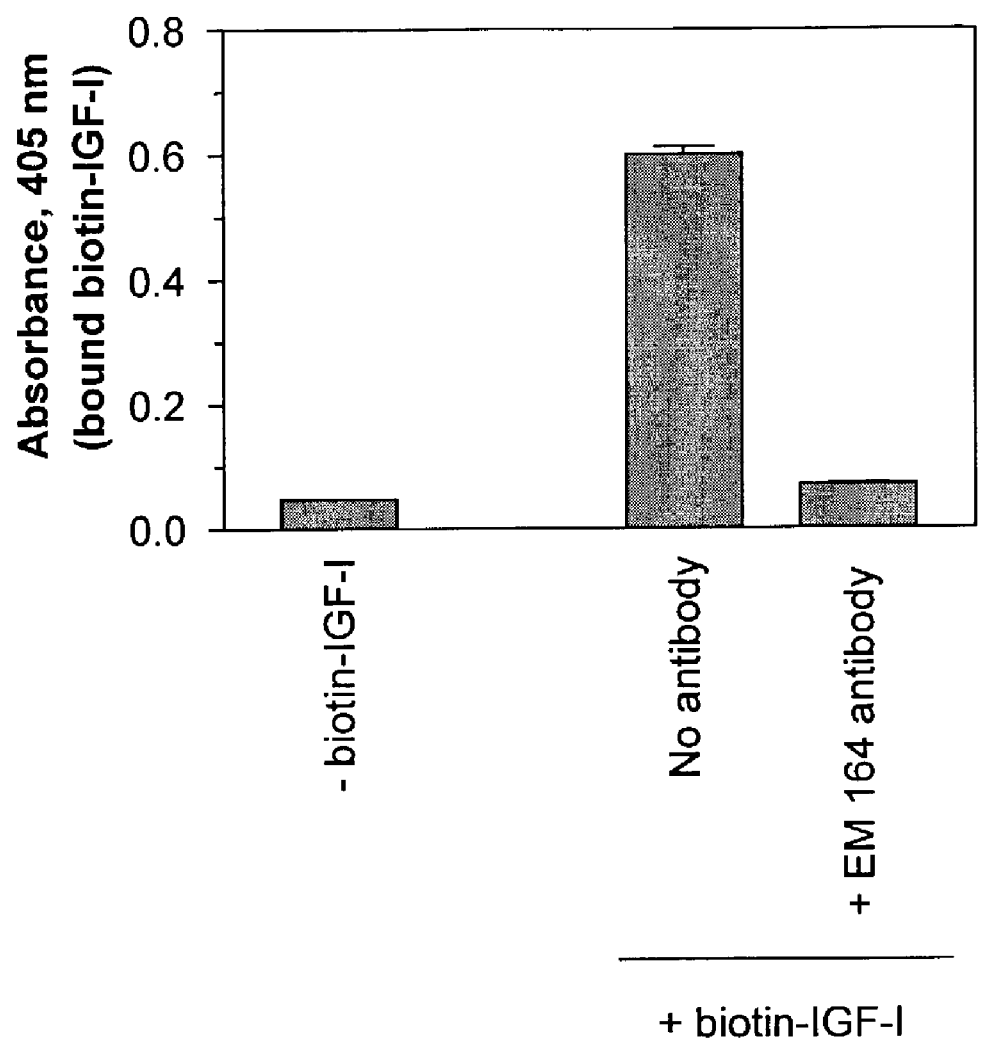
FIG. 3 shows the inhibition of the binding of biotinylated IGF-I to human breast cancer MCF-7 cells by EM164 antibody.

The binding of IGF-I to human breast cancer MCF-7 cells was inhibited by EM164 antibody (FIG. 3). MCF-7 cells were incubated with or without 5 µg/mL EM164 antibody for 2 h in serum-free medium, followed by incubation with 50 ng/mL biotinylated IGF-I for 20 min at 37° C. The cells were then washed twice with serum-free medium to remove unbound biotin-IGF-I, and were then lysed in 50 mM HEPES, pH 7.4, containing 1% NP-40 and protease inhibitors. An Immulon-2HB ELISA plate was coated with a mouse monoclonal anti-IGF-I receptor beta chain antibody and was used to capture the IGF-I receptor and bound biotin-IGF-I from the lysate. The binding of the coated antibody to the cytoplasmic C-terminal domain of the beta chain of IGF-I receptor did not interfere with the binding of biotin-IGF-I to the extracellular domain of IGF-I receptor. The wells were washed, incubated with streptavidin-horseradish peroxidase conjugate, washed again, and then detected using ABTS/$H_2O_2$ substrate. The inhibition of IGF-I binding to MCF-7 cells by 5 µg/mL EM164 antibody was essentially quantitative, and was almost equivalent to that of the ELISA background obtained using a control lacking biotin-IGF-I.

D. Inhibition of IGF-I Receptor Mediated Cell Signaling by EM164 Antibody

Figure 4:
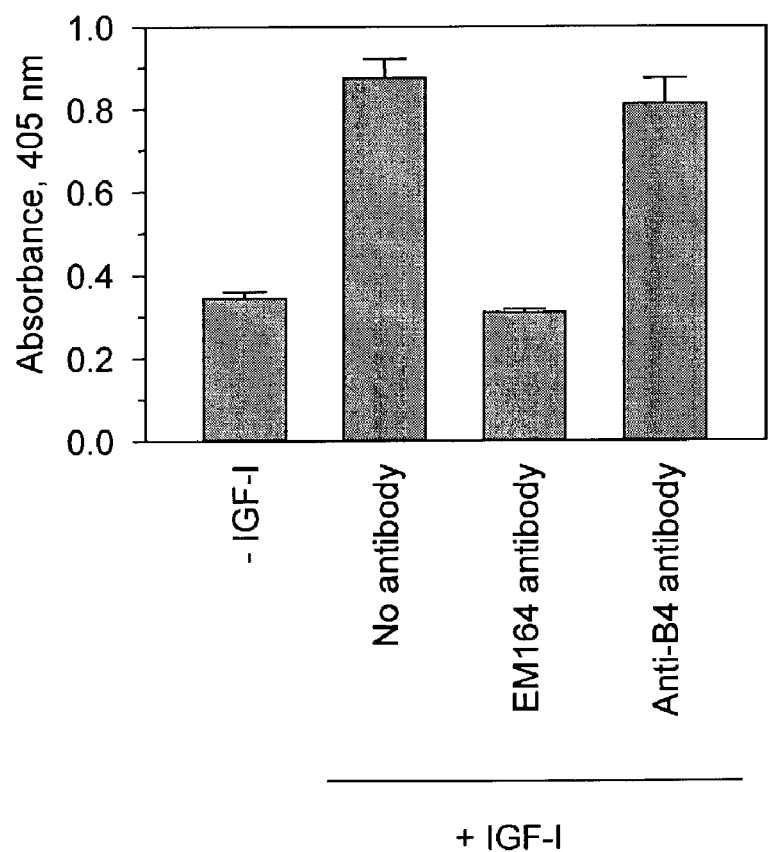
FIG. 4 shows the inhibition of IGF-I-stimulated autophosphorylation of IGF-I receptor in MCF-7 cells by EM164 antibody.
Figure 5:
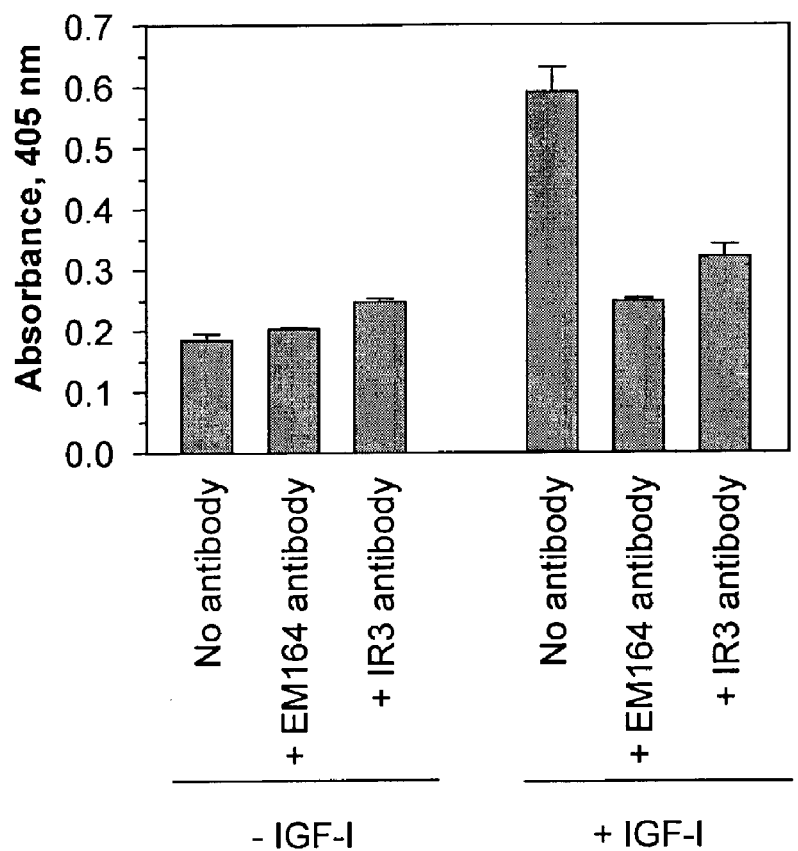
FIG. 5 shows the inhibition of IGF-I-stimulated IRS-1-phosphorylation in MCF-7 cells by EM164 antibody.
Figure 6:
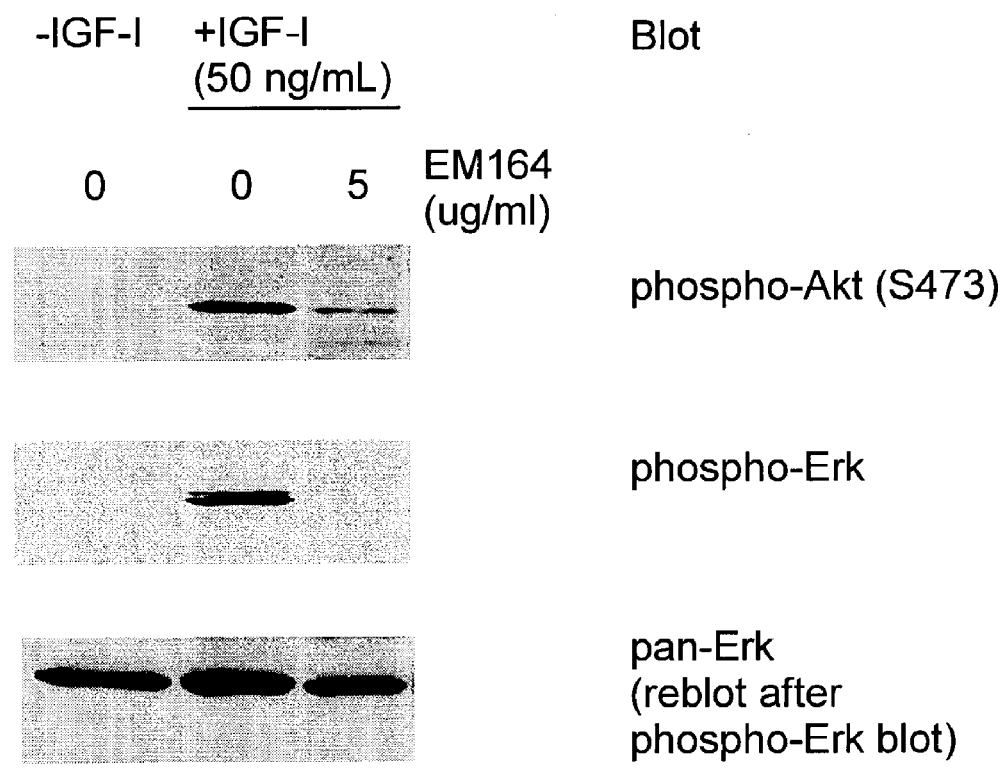
FIG. 6 shows the inhibition of IGF-I-stimulated signal transduction in SaOS-2 cells by EM164 antibody.

Treatment of breast cancer MCF-7 cells and osteosarcoma SaOS-2 cells with EM164 antibody almost completely inhibited intracellular IGF-I receptor signaling, as shown by the inhibition of IGF-I receptor autophosphorylation and by the inhibition of phosphorylation of its downstream effectors such as insulin receptor substrate-1 (IRS-1), Akt and Erk1/2 (FIGS. 4-6).

In FIG. 4, the MCF-7 cells were grown in a 12-well plate in regular medium for 3 days, and were then treated with 20 µg/mL EM164 antibody (or anti-B4 control antibody) in serum-free medium for 3 h, followed by stimulation with 50 ng/mL IGF-I for 20 min at 37° C. The cells were then lysed in ice-cold lysis buffer containing protease and phosphatase inhibitors (50 mM HEPES buffer, pH 7.4, 1% NP-40, 1 mM sodium orthovanadate, 100 mM sodium fluoride, 10 mM sodium pyrophosphate, 2.5 mM EDTA, 10 µM leupeptin, 5 µM pepstatin, 1 mM PMSF, 5 mM benzamidine, and 5 µg/mL aprotinin). An ELISA plate was pre-coated with anti-IGF-I receptor beta chain C-terminus monoclonal antibody TC123 and was incubated with the lysate samples for 5 h at ambient temperature to capture IGF-I receptor. The wells containing the captured IGF-I receptor were then washed and incubated with biotinylated anti-phosphotyrosine antibody (PY20; 0.25 µg/mL; BD Transduction Laboratories) for 30 min, followed by washes and incubation with streptavidin-horseradish peroxidase conjugate (0.8 µg/mL) for 30 min. The wells were washed and detected with ABTS/$H_2O_2$ substrate. Use of a control anti-B4 antibody showed no inhibition of the IGF-I stimulated autophosphorylation of IGF-I receptor. In contrast, a complete inhibition of the IGF-I stimulated autophosphorylation of IGF-I receptor was obtained upon treatment with EM164 antibody (FIG. 4).

To demonstrate inhibition of phosphorylation of insulin receptor substrate-1 (IRS-1), an ELISA using immobilized anti-IRS-1 antibody to capture IRS-1 from lysates was used, followed by measurement of the associated p85 subunit of phosphatidylinositol-3-kinase (PI-3-kinase) that binds to the phosphorylated IRS-1 (Jackson, J. G. et al., 1998, *J. Biol. Chem.*, 273, 9994-10003). In FIG. 5, MCF-7 cells were treated with 5 µg/mL antibody (EM164 or IR3) in serum-free medium for 2 h, followed by stimulation with 50 ng/mL IGF-I for 10 min at 37° C. Anti-IRS-1 antibody (rabbit polyclonal; Upstate Biotechnology) was indirectly captured by incubation with coated goat-anti-rabbit-IgG antibody on an ELISA plate, which was then used to capture IRS-1 from the cell lysate samples by overnight incubation at 4° C. The wells were then incubated with mouse monoclonal anti-p85-PI-3-kinase antibody (Upstate Biotechnology) for 4 h, followed by treatment with goat-anti-mouse-IgG-antibody-HRP conjugate for 30 min. The wells were then washed and detected using ABTS/ $H_2O_2$ substrate (FIG. 5). As shown in FIG. 5, EM164 antibody was more effective at inhibiting the IGF-I-stimulated IRS-1 phosphorylation than was IR3 antibody, and EM164 antibody did not show any agonistic activity on IRS-1 phosphorylation when incubated with cells in the absence of IGF-1.

The activation of other downstream effectors, such as Akt and Erk1/2, was also inhibited in a dose-dependent manner by EM164 antibody in SaOS-2 cells (FIG. 6) and in MCF-7 cells, as was shown using Western blots of lysates and phosphorylation-specific antibodies (rabbit polyclonal anti-phospho-Ser$^{473}$ Akt polyclonal and anti-phospho-ERK1/2 antibodies; Cell Signaling Technology). A pan-ERK antibody demonstrated equal protein loads in all lanes (FIG. 6). Treatment of SaOS-2 cells with EM164 antibody did not inhibit the EGF-stimulated phosphorylation of Erk1/2, thus demonstrating the specificity of inhibition of IGF-I receptor signaling pathway by EM164 antibody.

E. Inhibition of IGF-I-, IGF-II- and Serum-Stimulated Growth and Survival of Human Tumor Cells by EM164 Antibody Several human tumor cell lines were tested in serum-free conditions for their growth and survival response to IGF-I. These cell lines were treated with EM164 antibody in the presence of IGF-I, IGF-II, or serum, and their growth and survival responses were measured using an MTT assay after 2-4 days. Approximately 1500 cells were plated in a 96-well plate in regular medium with serum, which was replaced with serum-free medium the following day (either serum-free RPMI medium supplemented with transferrin and BSA, or phenol-red free medium as specified by Dufourny, B. et al., 1997, *J. Biol. Chem.*, 272, 31163-31171). After one day of growth in serum-free medium, the cells were incubated with about 75 µL of 10 µg/mL antibody for 2-3 h, followed by the addition of 25 µL of IGF-I (or IGF-II or serum) solution to obtain a final concentration of 10 ng/mL IGF-I, or 20 ng/mL IGF-II, or 0.04-10% serum. The cells were then allowed to grow for another 2-3 days. A solution of MTT (3-(4,5)-dimethylthiazol-2-yl)-2,5-diphenyltetrazolium bromide; 25 µL of a 5 mg/mL solution in PBS) was then added and the cells were returned to the incubator for 2-3 h. The medium was then removed and replaced by 100 µL DMSO, mixed, and the absorbance of the plate was measured at 545 nm. Several human tumor cell lines showed a growth and survival response upon addition of IGF-I or IGF-II or serum that was significantly inhibited by EM164 antibody (Table 1).

TABLE 1

INHIBITION OF IGF-I-STIMULATED GROWTH AND SURVIVAL OF TUMOR CELLS BY EM164 ANTIBODY

| Tumor Cell Type | Fold growth response to IGF-I (MTT assay: ratio for IGF-I treated vs untreated cells in serum-free medium)[a] | % Inhibition by EM164 antibody of IGF-I-stimulated growth in serum-free medium | Inhibition by EM164 antibody of Growth/survival of cells in 1.25-10% serum[b] |
|---|---|---|---|
| MCF-7 (breast) | 1.7-2.8 | 100% | 85% |
| HT-3 (cervical) | 2 | 70-90% | ND |
| Colo 205 (colon) | 2.3 | 50% | Yes |
| HT-29 | 1.5 | 60% | Yes |
| NCI-H838 (lung) | 3 | 100% | 85-90% |
| Calu-6 | 1.6-1.8 | 85% | Yes |
| SK-LU-1 | 1.4 | 100% | No |
| NCI-H596 | 1.4 | 100% | Weakly |
| A 549 | 1.2 | 80% | ND |
| A 375 (melanoma) | 1.6 | 90% | No |
| SK-Mel-37 | 1.4 | 85% | ND |
| RD (rhabdomyocarcoma) | 1.7 | 85-100% | Yes |
| SaOS-2 (osteosarcoma) | 2.5 | 100% | Yes |
| A 431 (epidermoid) | 2.2 | 85% | Yes |
| SK-N-SH (neuroblastoma) | 2 | 85% | 30-50% |

[a]MTT assay of 3- to 4-day growth/survival of cells in response to 10 ng/mL IGF-I in serum-free medium containing 5-10 µg/mL EM164 antibody.
[b]inhibition of growth of cells in 1.25-10% serum in the presence of 5-10 µg/mL EM164 antibody by MTT assay or colony formation assay based on comparison with the control (with serum but without antibody); the extent of inhibition was quantitatively measured for MCF-7, NCI-H838 and SK-N-SH cells based on controls (without serum but with antibody, and with serum but without antibody) to account for autocrine/paracrine IGF-stimulation by cells. NDindicates no data or poor data due to staining difficulties.

Figure 7:
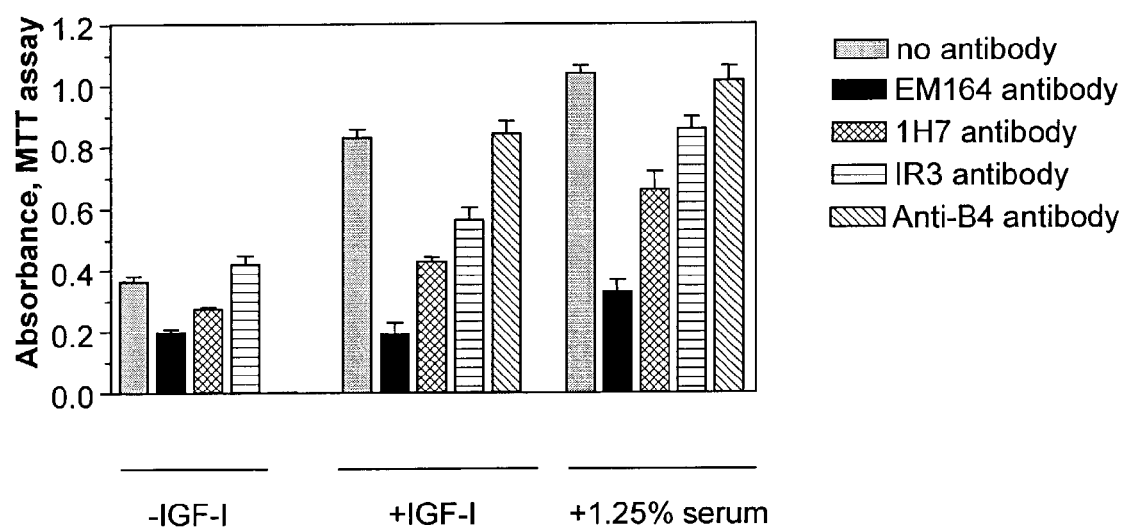
FIG. 7 shows the effect of EM164 antibody on the growth and survival of MCF-7 cells under different growth conditions, as assessed by MTT assay.
Figure 8:
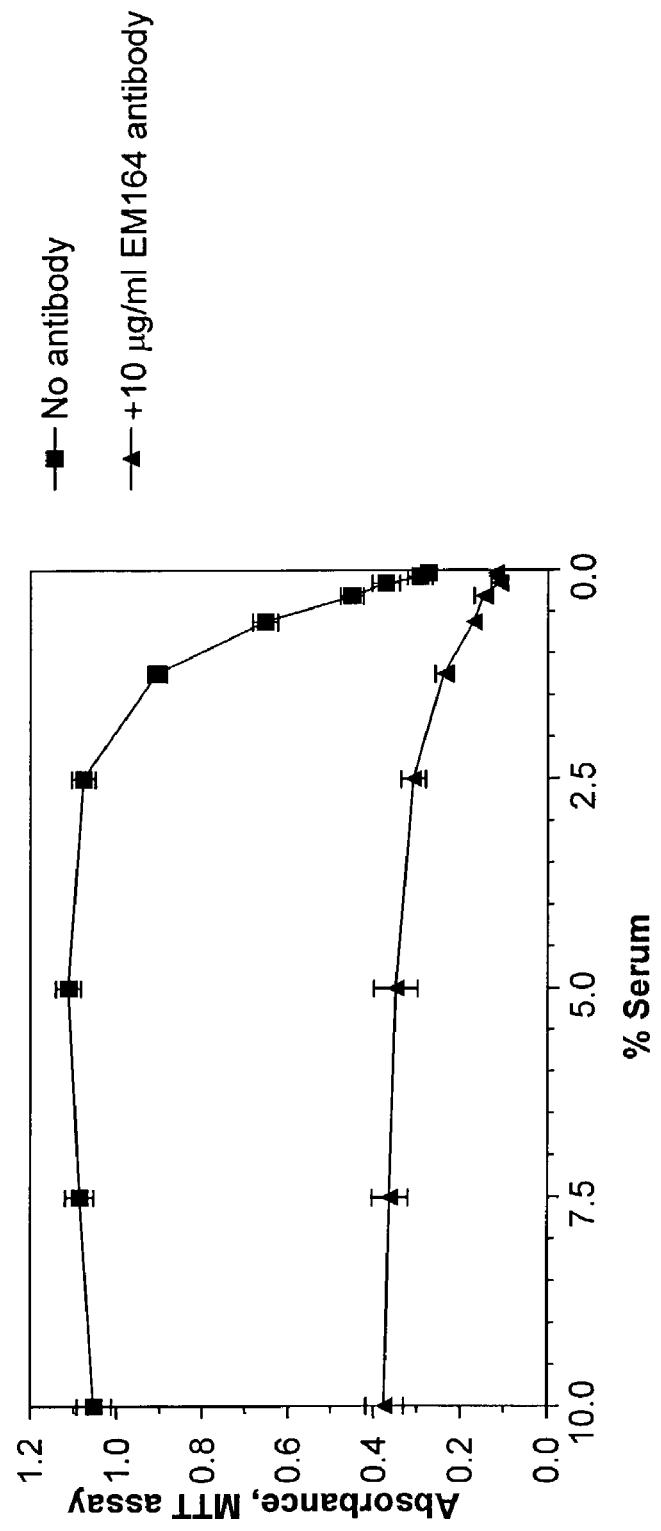
FIG. 8 shows the effect of EM164 antibody on the growth and survival of MCF-7 cells in the presence of various serum concentrations.

The EM164 antibody strongly inhibited IGF-1-or serum-stimulated growth and survival of breast cancer MCF-7 cells (FIGS. 7 and 8). In a separate experiment, the EM164 antibody strongly inhibited IGF-II-stimulated growth and survival of MCF-7 cells. Previous reports using commercially available antibodies such as IR3 antibody showed only weak inhibition of serum-stimulated growth and survival of MCF-7 cells, as confirmed in FIG. 7 for the IR3 and 1H7 antibodies (Cullen, K. J. et al., 1990, *Cancer Res.*, 50, 48-53). In contrast, EM164 antibody was a potent inhibitor of the serum- or IGF-stimulated growth of MCF-7 cells. As shown in FIG. 8, EM164 antibody was equally effective in inhibiting the growth and survival of MCF-7 cells over a wide range of serum concentrations (0.04-10% serum).

The growth inhibition of MCF-7 cells by EM164 antibody was measured by counting cells. Thus, in a 12-well plate, about 7500 cells were plated in RPMI medium with 10% FBS, in the presence or absence of 10 µg/mL EM164 antibody. After 5 days of growth, the cell count for the untreated control sample was $20.5 \times 10^4$ cells, in contrast to a cell count of only $1.7 \times 10^4$ cells for the EM164 antibody-treated sample. Treatment with the EM164 antibody inhibited the growth of MCF-7 cells by about 12-fold in 5 days. This inhibition by EM164 antibody was significantly greater than was a reported 2.5-fold inhibition using IR3 antibody in a 6-day assay for MCF-7 cells (Rohlik, Q. T. et al., 1987, *Biochem. Biophys. Res. Commun.*, 149, 276-281).

Figure 9:
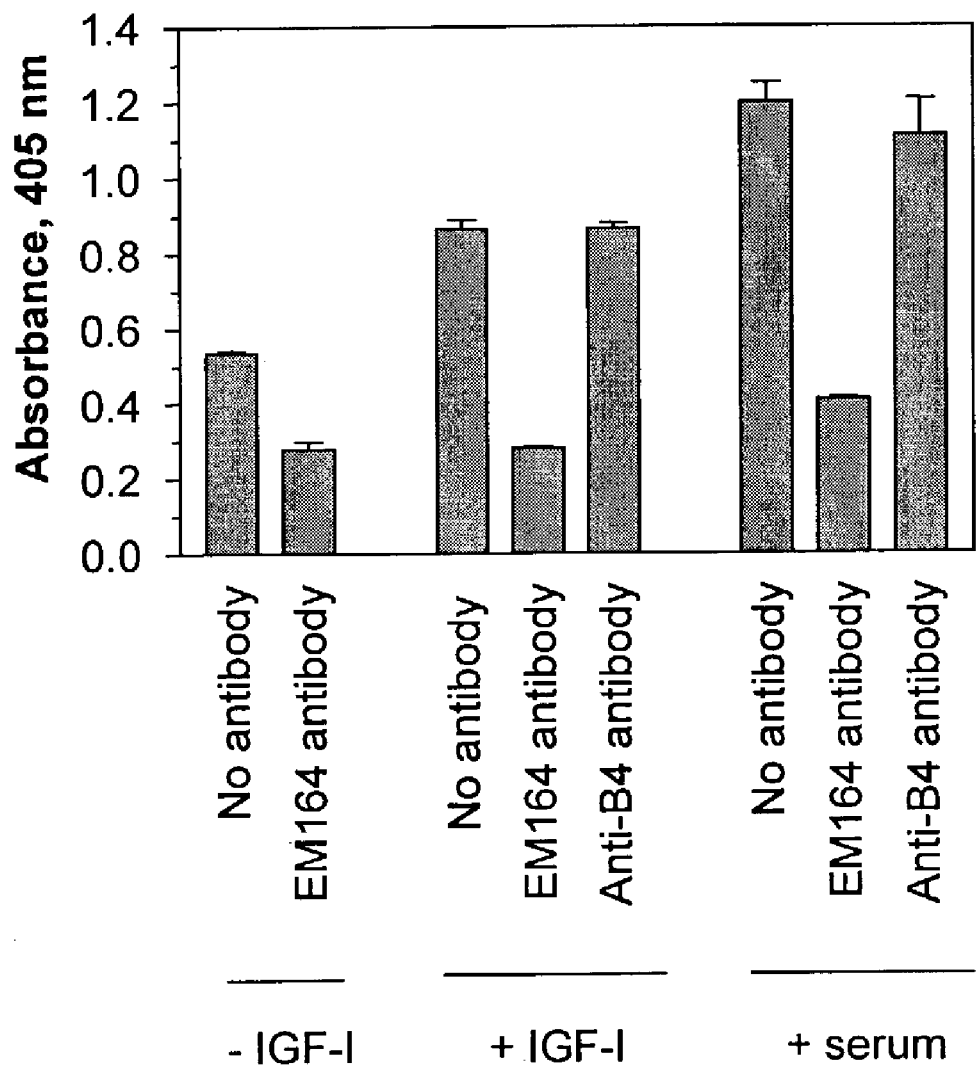
FIG. 9 shows the inhibition of IGF-I- and serum-stimulated growth and survival of NCI-H838 cells by EM164 antibody.

The IGF-I- and serum-stimulated growth and survival of a non-small cell lung cancer line NCI-H838 were also strongly inhibited by EM164 antibody, compared to a control anti-B4 antibody (FIG. 9). Treatment with EM164 antibody in serum-free medium produced a smaller signal than the untreated sample for both NCI-H838 and MCF-7 cells, presumably because EM 164 antibody also inhibited the autocrine and paracrine IGF-I and IGF-II stimulation of these cells (FIGS. 7 and 9). The colony size of HT29 colon cancer cells was also greatly reduced upon treatment with EM164 antibody.

EM164 antibody is therefore unique among all known anti-IGF-I receptor antibodies in its effectiveness to inhibit the serum-stimulated growth of tumor cells such as MCF-7 cells and NCI-H838 cells by greater than 80%.

F. Synergistic Inhibition by EM164 Antibody of Growth and Survival of Human Tumor Cells in Combinations with Other Cytotoxic and Cytostatic Agents The combined administration of EM164 antibody with taxol was significantly more inhibitory to the growth and survival of non-small cell lung cancer Calu6 cells than was taxol alone. Similarly, the combination of EM164 antibody with camptothecin was significantly more inhibitory than camptothecin alone toward the growth and survival of colon cancer HT29 cells. Because EM164 antibody alone was not expected to be as toxic to cells as organic chemotoxic drugs, the synergism between the predominantly cytostatic effect of EM164 antibody and the cytotoxic effect of the chemotoxic drug may be highly efficacious in combination cancer therapies in clinical settings.

The combined effect of EM164 antibody with an anti-EGF receptor antibody (KS77) was significantly more inhibitory than either EM164 antibody or KS77 antibody alone on the growth and survival of several tumor cell lines such as HT-3 cells, RD cells, MCF-7 cells, and A431 cells. Therefore, the synergistic effect of combining neutralizing antibodies for two growth factor receptors such as IGF-I receptor and EGF receptor may also be useful in clinical cancer treatment.

Conjugates of EM164 antibody with cytotoxic drugs are also valuable in targeted delivery of the cytotoxic drugs to the tumors over expressing IGF-I receptor. Conjugates of EM164 antibody with radiolabels or other labels can be used in the treatment and imaging of tumors that over express IGF-I receptor.

Figure 10:
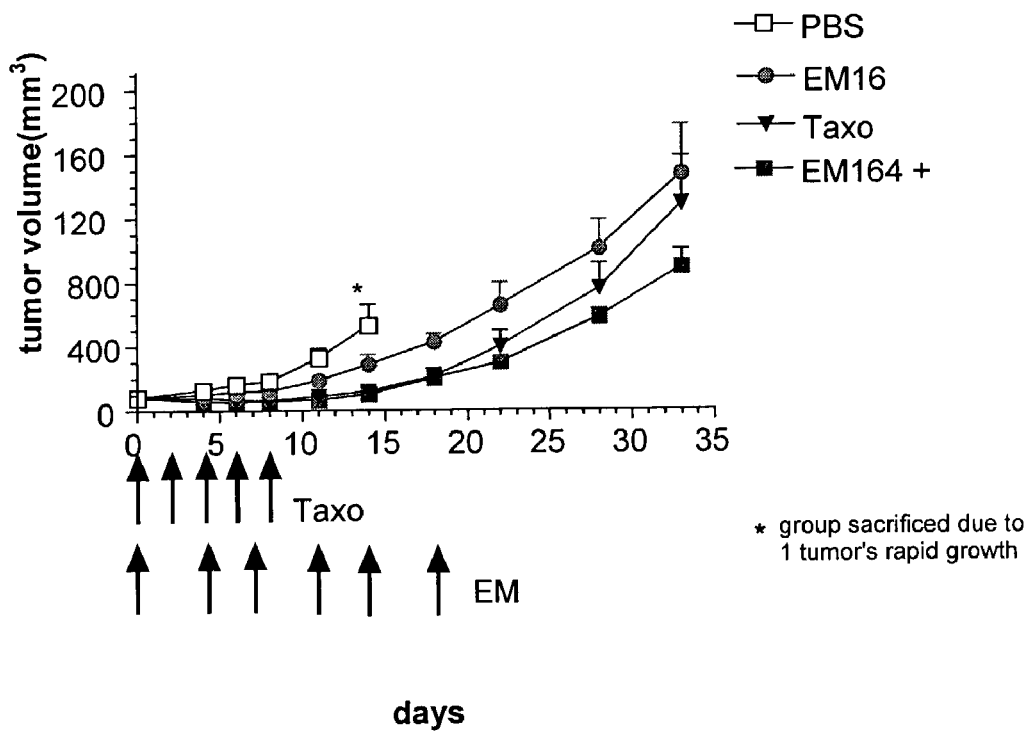
FIG. 10 shows the effect of treatment with EM164 antibody, taxol, or a combination of EM164 antibody and taxol, on the growth of a Calu-6 lung cancer xenograft in mice.

G. EM164 Antibody Treatment Alone, and in Combination with Taxol, on Mice with Human Tumor Calu-6 Xenograft Human non-small cell lung cancer Calu-6 xenografts were established in mice by subcutaneous injections of $1 \times 10^7$ Calu-6 cells. As shown in FIG. 10, these mice containing established 100 mm³ Calu-6 xenografts were treated with EM 164 antibody alone (6 injections of 0.8 mg/mouse, i. v., two per week) or with taxol alone (five injections of taxol, i.p. every two days; 15 mg/kg), or with a combination of taxol and EM164 antibody treatments, or PBS alone (200 µL/mouse, 6 injections, two per week, i.v.) using five mice per treatment group. The growth of tumors was significantly slowed by EM164 antibody treatment compared to a PBS control. No toxicity of EM164 antibody was observed, based on measurements of the weights of the mice. Although taxol treatment alone was effective until day 14, the tumor then started to grow back. However, the growth of the tumor was delayed significantly in the group that was treated by a combination of taxol and EM164 antibody, compared to the group that was treated with taxol alone.

H. Cloning and Sequencing of the Light and Heavy Chains of EM164 Antibody

Total RNA was purified from EM164 hybridoma cells. Reverse transcriptase reactions were performed using 4-5 µg total RNA and either oligo dT or random hexamer primers.

PCR reactions were performed using a RACE method described in Co et al. (J. Immunol., 148, 1149-1154 (1992)) and using degenerate primers as described in Wang et al., (J. Immunol. Methods, 233, 167-177 (2000)). The RACE PCR method required an intermediate step to add a poly G tail on the 3'ends of the first strand cDNAs. RT reactions were purified with Qianeasy (Qiagen) columns and eluted in 50 µl 1×NEB buffer 4. A dG tailing reaction was performed on the eluate with 0.25 mM $CoCl_2$, 1 mM dGTP, and 5 units terminal transferase (NEB), in 1× NEB buffer 4. The mixture was incubated at 37° C. for 30 minutes and then ⅕ of the reaction (10 µl) was added directly to a PCR reaction to serve as the template DNA.

The RACE and degenerate PCR reactions were identical except for differences in primers and template. The terminal transferase reaction was used directly for the RACE PCR template, while the RT reaction mix was used directly for degenerate PCR reactions.

In both RACE and degenerate PCR reactions the same 3' light chain primer:

HindKL—tatagagctcaagcttggatggtgggaa-gatggatacagttggtgc (SEQ ID NO: 14) and 3' heavy chain primer:

Bgl2IgG1—ggaagatctatagacagatgggggtgtcgttttggc (SEQ ID NO: 15) were used.

In the RACE PCR, one poly C 5' primer was used for both the heavy and light chain:

EcoPolyC—TATATCTAGAATTC-CCCCCCCCCCCCCCCC (SEQ ID NO: 16), while the degenerate 5' end PCR primers were:

Sac1MK—GGGAGCTCGAYATTGTGMTSACMCAR-WCTMCA (SEQ ID NO: 17) for the light chain, and an equal mix of:

(EcoR1MH1—CTTCCGGAATTCSARGTNMAGCTG-SAGSAGTC) (SEQ ID NO: 18) and (EcoR1MH2—CTTCCGGAATTCSARGTNMAGCTG-SAGSAGTCWGG) (SEQ ID NO: 19) for the heavy chain.

In the above primer sequences, mixed bases are defined as follows: H=A+T+C, S=g+C, Y=C+T, K=G+T, M=A+C, R=A+g, W=A+T, V=A+C+G.

The PCR reactions were performed using the following program: 1) 94° C. 3 min, 2) 94° C. 15 sec, 3) 45° C. 1 min, 4) 72° C. 2 min, 5) cycle back to step #2 29 times, 6) finish with a final extension step at 72° C. for 10 min.

The PCR products were cloned into pBluescript II SK+ (Stratagene) using restriction enzymes created by the PCR primers.

Several individual light and heavy chain clones were sequenced by conventional means to identify and avoid possible polymerase generated sequence errors (FIGS. 12 and 13). Using Chothia canonical classification definitions, the three light chain and heavy chain CDRs were identified (FIGS. 12-14).

A search of the NCBI IgBlast database indicated that the anti-IGF-I receptor antibody light chain variable region probably derived from the mouse IgVk Cr1 germline gene while the heavy chain variable region probably derived from the IgVh J558.c germline gene (FIG. 15).

Protein sequencing of murine EM164 antibody was performed to confirm the sequences shown in FIGS. 12 and 13. The heavy and light chain protein bands of purified EM164 antibody were transferred to a PVDF membrane from a gel (SDS-PAGE, reducing conditions), excised from the PVDF membrane and analyzed by protein sequencing. The N-terminal sequence of the light chain was determined by Edman sequencing to be: DVLMTQTPLS (SEQ ID NO: 20) which matches the N-terminal sequence of the cloned light chain gene obtained from the EM164 hybridoma.

The N-terminus of the heavy chain was found to be blocked for Edman protein sequencing. A tryptic digest peptide fragment of the heavy chain of mass 1129.5 (M+H+, monoisotopic) was fragmented via post-source decay (PSD) and its sequence was determined to be GRPDYYGSSK (SEQ ID NO: 21). Another tryptic digest peptide fragment of the heavy chain of mass 2664.2 (M+H+, monoisotopic) was also fragmented via post-source decay (PSD) and its sequence was identified as: SSSTAYMQLSSLTSEDSAVYYFAR (SEQ ID NO: 22). Both of these sequences match perfectly those of CDR3 and framework 3 (FR3) of the cloned heavy chain gene obtained from the EM164 hybridoma.

I. Recombinant Expression of EM164 Antibody

Figure 16:
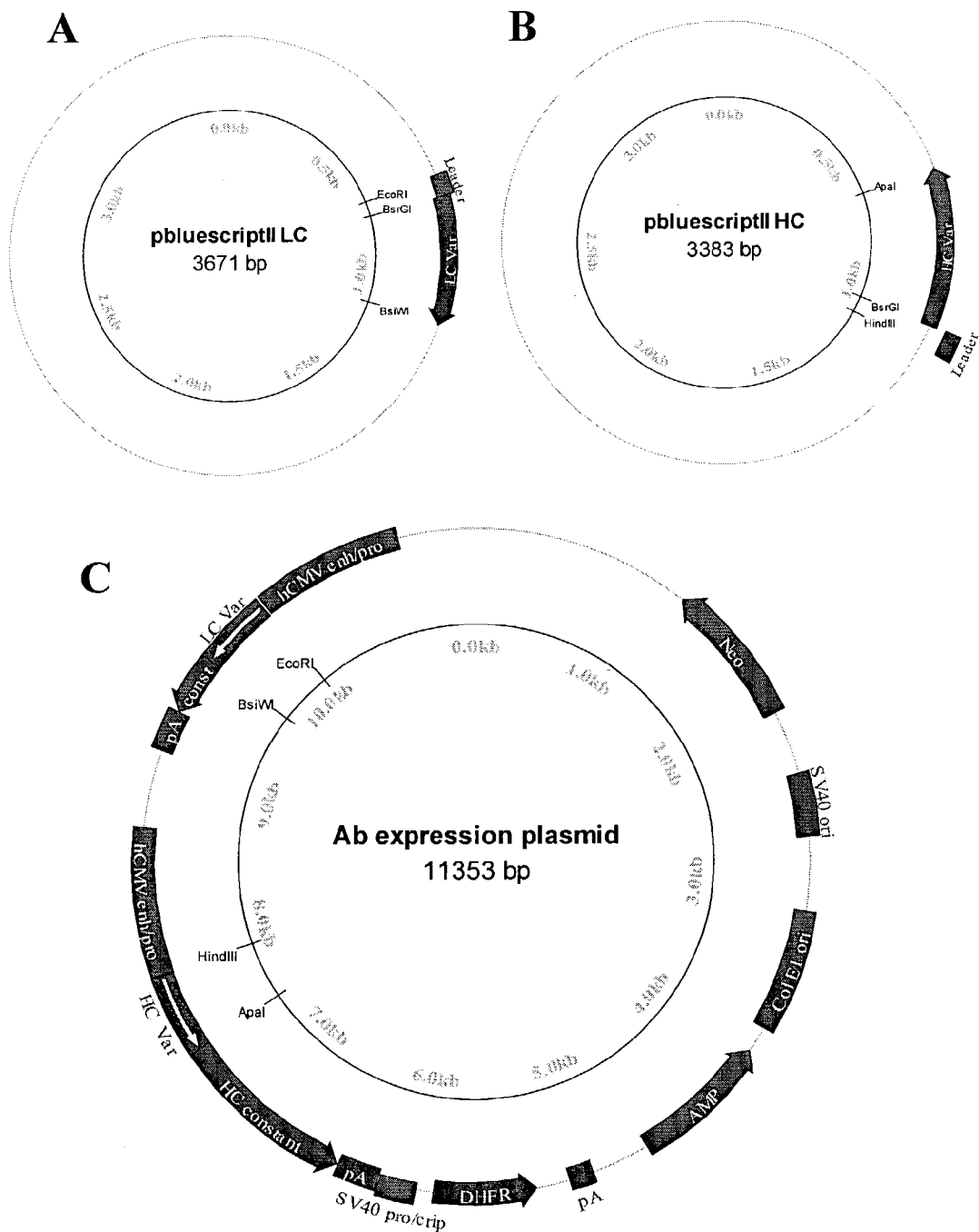
FIG. 16 shows the plasmids used to build and express the recombinant chimeric and humanized EM164 antibodies. A) a light chain cloning plasmid, B) a heavy chain cloning plasmid, C) a mammalian antibody expression plasmid.

The light and heavy chain paired sequences were cloned into a single mammalian expression vector (FIG. 16). The PCR primers for the human variable sequences created restriction sites that allowed the human signal sequence to be attached while in the pBluescriptII cloning vector, and the variable sequences were cloned into the mammalian expression plasmid using EcoRI and BsiWI or HindIII and ApaI sites for the light chain or heavy chain, respectively (FIG. 16). The light chain variable sequences were cloned in-frame onto the human IgK constant region and the heavy chain variable sequences were cloned into the human Iggamma1 constant region sequence. In the final expression plasmids, human CMV promoters drove the expression of both the light and heavy chain cDNA sequences. Expression and purification of the recombinant mouse EM164 antibody proceeded according to methods that are well-known in the art.

Example 2

Humanized Versions of EM164 Antibody

Resurfacing of the EM164 antibody to provide humanized versions suitable as therapeutic or diagnostic agents generally proceeds according to the principles and methods disclosed in U.S. Pat. No. 5,639,641, and as follows.

A. Surface Prediction

The solvent accessibility of the variable region residues for a set of antibodies with solved structures was used to predict the surface residues for the murine anti-IGF-I receptor antibody (EM164) variable region. The amino acid solvent accessibility for a set of 127 unique antibody structure files (Table 2) were calculated with the MC software package (Pedersen et al., 1994, J. Mol. Biol., 235, 959-973). The ten most similar light chain and heavy chain amino acid sequences from this set of 127 structures were determined by sequence alignment. The average solvent accessibility for each variable region residue was calculated, and positions with greater than a 30% average accessibility were considered to be surface residues. Positions with average accessibilities of between 25% and 35% were further examined by calculating the individual residue accessibility for only those structures with two identical flanking residues.

TABLE 2

127 antibody structures from the Brookhaven database used to predict the surface of anti-IGF-I-receptor antibody (EM164)
127 Brookhaven structure files used for surface predictions

| | | | | | | | | | |
|---|---|---|---|---|---|---|---|---|---|
| 2rcs | 3hfl | 3hflm | 1aif | 1a3r | 1bbj | 43c9 | 4fab | 6fab | 7fab |
| 2gfb | 2h1p | 2hfl | 1a6t | 1axt | 1bog | 2hrp | 2jel | 2mcp | 2pcp |
| 1yuh | 2bfv | 2cgr | 8fab | 1ae6 | 1bvl | 2dbl | 2f19 | 2fb4 | 2fbj |
| 1sm3 | 1tet | 1vfa | glb2 | 1a4j | 1cly | 1vge | 1yec | 1yed | 1yee |
| 1nsn | 1opg | 1osp | 1aj7 | 1ayl | 1clz | 1plg | 1psk | 1rmf | 1sbs |
| 1ncd | 1nfd | 1ngp | 1acy | 1afv | 1cbv | 1nld | 1nma | 1nmb | 1nqb |
| 1mcp | 1mfb | 1mim | 15c8 | 1a5f | 1axs | 1mlb | 1mpa | 1nbv | 1ncb |
| 1jrh | 1kb5 | 1kel | 1ap2 | 1b2w | 1adq | 1kip | 1kir | 1lve | 1mam |
| 1igi | 1igm | 1igt | 1ad0 | 1baf | 1cfv | 1igy | 1ikf | 1jel | 1jhl |
| 1gpo | 1hil | 1hyx | 1a0q | 1bjm | 1clo | 1iai | 1ibg | 1igc | 1igf |
| 1fpt | 1frg | 1fvc | 1aqk | 1bln | 1d5b | 1gaf | 1ggi | 1ghf | 1gig |
| 1fai | 1fbi | 1fdl | 1ad9 | 1bbd | 1f58 | 1fgv | 1fig | 1flr | 1for |
| | 1dbl | 1dfb | 1a3l | 1bfo | 1eap | 1dsf | 1dvf | | |

B. Molecular Modeling:

A molecular model of murine EM164 was generated using the Oxford Molecular software package AbM. The antibody framework was built from structure files for the antibodies with the most similar amino acid sequences, which were 2jel for the light chain and 1nqb for the heavy chain. The non-canonical CDRs were built by searching a C-α structure database containing non-redundant solved structures. Residues that lie within 5 Å of a CDR were determined.

C. Human Ab Selection

The surface positions of murine EM164 were compared to the corresponding positions in human antibody sequences in the Kabat database (Johnson, G. and Wu, T. T. (2001) Nucleic Acids Research, 29: 205-206). The antibody database management software SR (Searle 1998) was used to extract and align the antibody surface residues from natural heavy and light chain human antibody pairs. The human antibody surface with the most identical surface residues, with special consideration given to positions that come within 5 Å of a CDR, was chosen to replace the murine anti-IGF-I receptor antibody surface residues.

D. PCR Mutagenesis

PCR mutagenesis was performed on the murine EM164 cDNA clone (above) to build the resurfaced, human EM164 (herein huEM164). Primer sets were designed to make the 8 amino acid changes required for all tested versions of huEM164, and additional primers were designed to alternatively make the two 5 Å residue changes (Table 3). PCR reactions were performed with the following program: 1) 94° C. 1 min, 2) 94° C. 15 sec, 3) 55° C. 1 min, 4) 72° C. 1 min, 5) cycle back to step #2 29 times, 6) finish with a final extension step at 72° C. for 4 min. The PCR products were digested with their corresponding restriction enzymes and were cloned into the pBluescript cloning vectors as described above. Clones were sequenced to confirm the desired amino acid changes.

TABLE 3

PCR primers used to build 4 humanized EM164 antibodies

| Primer | Sequence | SEQ ID NO: |
|---|---|---|
| Em164hcvv | CAGGTGTACACTCCCAGGTCCAACTGGTGCAGTCTGGGGCTGAAGTGGTGAAGCCTG | 23 |
| Em164hcqqgo11 | CAATCAGAAGTTCCAGGGGAAGGCCACAC | 24 |
| Em164hcqqgo12 | CCTTCCCCTGGAACTTCTGATTGTAGTTAGTACG | 25 |
| Em164lcv3 | CAGGTGTACACTCCGATGTTGTGATGACCCAAACTCC | 26 |
| Em164lc13 | CAGGTGTACACTCCGATGTTTTGATGACCCAAACTCC | 27 |
| Em164lcp18 | GACTAGATCTGCAAGAGATGGAGGCTGGATCTCCAAGAC | 28 |
| Em164lcbg12 | TTGCAGATCTAGTCAGAGCATAGTACATAGTAATG | 29 |
| Em164r45 | GAATGGTACCTGCAGAAACCAGGCCAGTCTCCAAGGCTCCTGATCTAC | 30 |
| Em164a67o11 | GTGGCAGTGGAGCAGGGACAGATTTCAC | 31 |
| Em164a67o12 | GAAATCTGTCCCTGCTCCACTGCCACTG | 32 |

E. Variable Region Surface Residues

The antibody resurfacing techniques described by Pedersen et al. (J. Mol. Biol., 235, 959-973, 1994) and Roguska et al. (Protein Eng., 9, 895-904, 1996) begin by predicting the surface residues of the murine antibody variable sequences. A surface residue is defined as an amino acid that has at least 30% of its total surface area accessible to a water molecule.

Figure 17:
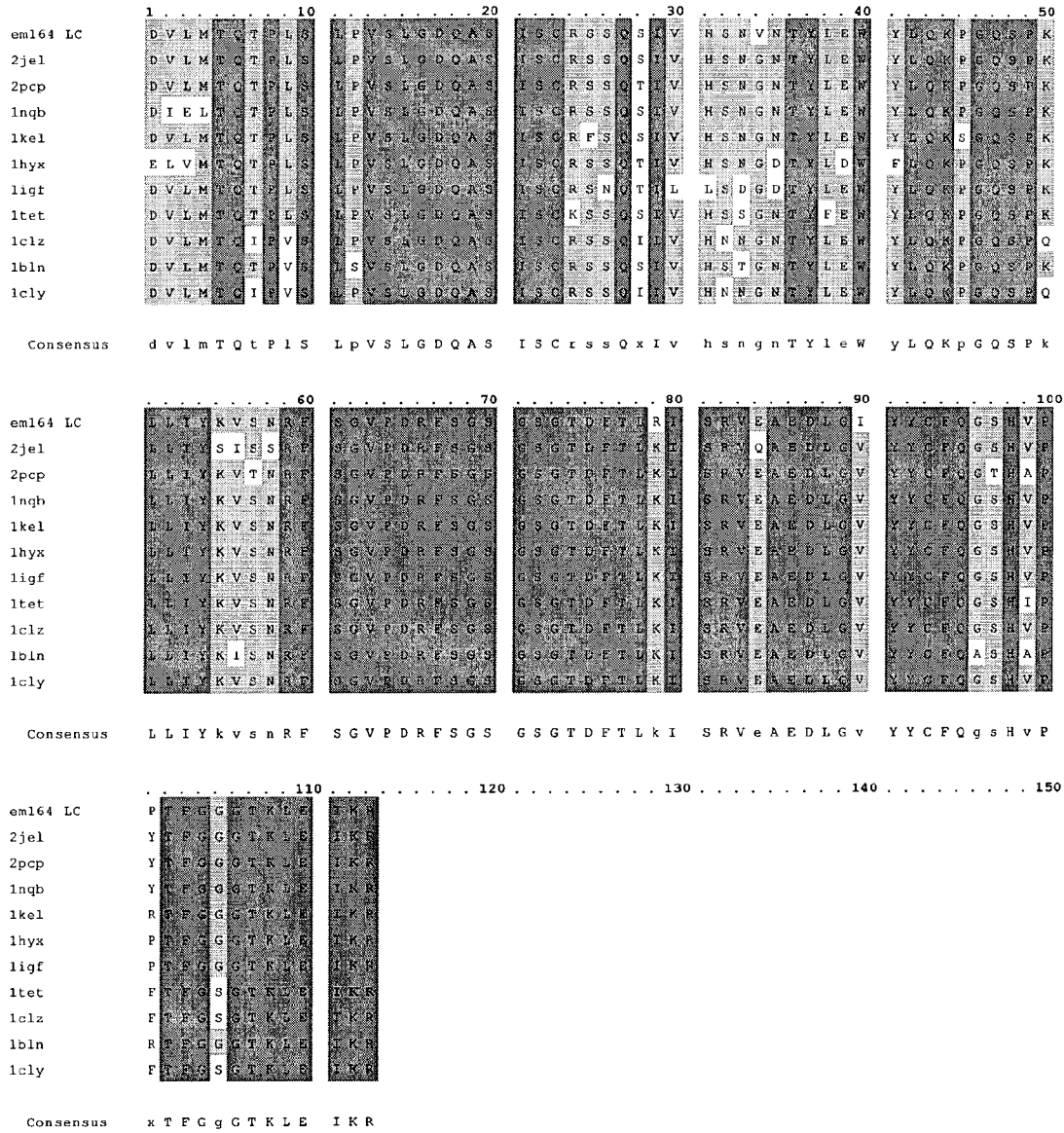
FIG. 17 shows the 10 most homologous amino acid sequences of the light chains screened from the 127 antibodies in the set of structure files used to predict the surface residues of EM164. em164 LC (SEQ ID NO:58), 2jel (SEQ ID NO:59), 2pcp (SEQ ID NO:60), 1nqb (SEQ ID NO:61), 1kel (SEQ ID NO:62), 1hyx (SEQ ID NO:63), 1igf (SEQ ID NO:64), 1tet (SEQ ID NO:65), 1clz (SEQ ID NO:66), 1bln (SEQ ID NO:67), 1cly (SEQ ID NO:68), Consensus (SEQ ID NO:69).

The 10 most homologous antibodies in the set of 127 antibody structure files were identified (FIGS. 17 and 18). The solvent accessibility for each Kabat position was averaged for these aligned sequences and the distribution of the relative accessibilities for each residue were as shown in FIG. 19. Both the light and heavy chain have 26 residues with average relative accessibilities of at least 30% (FIG. 19): these residues were therefore the predicted surface residues for EM164. Several residues had average accessibilities of between 25% and 35%, and these were further examined by averaging only the antibodies with two identical residues flanking either side of the residue (Tables 4 and 5). After this additional analysis, the original set of surface residues that was identified above remained unchanged.

TABLE 4

Surface residues and average accessibility (ave. acc.) for the light and heavy chain variable sequences of EM164 antibody
EM164 Surface Residues

| Light Chain | | | Heavy Chain | | |
| --- | --- | --- | --- | --- | --- |
| EM164 | Kabat # | Ave. Acc. | EM164 | Kabat # | Ave. Acc. |
| D | 1 | 45.89 | Q | 1 | 58.19 |
| L | 3 | 41.53 | Q | 3 | 34.08 |
| T | 7 | 31.40 | Q | 5 | 34.36 |
| L | 9 | 50.08 | A | 9 | 38.01 |
| L | 15 | 35.45 | L | 11 | 47.72 |
| Q | 18 | 39.79 | K | 13 | 46.51 |
| R | 24 | 34.36 | P | 14 | 31.49 |
| S | 26 | 32.63 | G | 15 | 31.42 |
| Q | 27 | 34.35 | K | 19 | 34.41 |
| N | 28 | 36.38 | K | 23 | 31.23 |
| P | 40 | 43.05 | T | 28 | 36.24 |
| G | 41 | 46.56 | P | 41 | 44.01 |
| Q | 42 | 34.92 | G | 42 | 42.62 |
| K | 45 | 30.58 | Q | 43 | 46.85 |
| S | 52 | 30.40 | E | 61 | 46.68 |
| S | 56 | 41.46 | K | 62 | 44.87 |
| G | 57 | 42.41 | K | 64 | 38.92 |
| D | 60 | 45.96 | R | 65 | 40.06 |
| S | 67 | 38.20 | K | 73 | 35.92 |
| R | 77 | 42.61 | S | 74 | 48.91 |
| E | 81 | 38.46 | S | 82B | 32.72 |
| V | 95E | 34.83 | S | 84 | 35.21 |
| K | 103 | 31.10 | E | 85 | 39.62 |
| K | 107 | 36.94 | D | 98 | 36.00 |
| R | 108 | 60.13 | A | 106 | 37.65 |
| A | 109 | 53.65 | S | 113 | 43.42 |

TABLE 5

Residues which had average accessibilities between 25% and 35% were further analyzed by averaging a subset of antibodies that had two identical residues flanking either side of the residue in question. These borderline surface positions and their new average accessibilities are given. The NA's refer to residues with no identical flanking residues in the 10 most similar antibodies.
Borderline Surface Residues

| Light Chain | | | Heavy Chain | | |
| --- | --- | --- | --- | --- | --- |
| EM164 | Kabat # | Ave. Acc. | EM164 | Kabat # | Ave. Acc. |
| T | 5 | 28.68 | Q | 3 | 31.62 |
| T | 7 | 30.24 | Q | 5 | 36.07 |

TABLE 5-continued

Residues which had average accessibilities between 25% and 35% were further analyzed by averaging a subset of antibodies that had two identical residues flanking either side of the residue in question. These borderline surface positions and their new average accessibilities are given. The NA's refer to residues with no identical flanking residues in the 10 most similar antibodies.
Borderline Surface Residues

| Light Chain | | | Heavy Chain | | |
| --- | --- | --- | --- | --- | --- |
| EM164 | Kabat # | Ave. Acc. | EM164 | Kabat # | Ave. Acc. |
| P | 12 | 26.59 | P | 14 | 29.88 |
| G | 16 | 25.20 | G | 15 | 30.87 |
| D | 17 | 25.73 | S | 17 | 25.64 |
| S | 20 | 25.37 | K | 19 | 35.06 |
| R | 24 | 36.73 | K | 23 | 31.48 |
| S | 26 | 31.00 | G | 26 | 30.53 |
| Q | 27 | 32.29 | S | 31 | 27.12 |
| S | 27A | 29.78 | R | 56 | NA |
| V | 27C | 29.05 | T | 68 | 27.71 |
| V | 29 | NA | T | 70 | 24.65 |
| Q | 42 | 34.92 | S | 75 | 18.80 |
| K | 45 | 32.24 | S | 82B | 32.87 |
| S | 52 | 30.02 | P | 97 | NA |
| R | 54 | 29.50 | Y | 99 | NA |
| D | 70 | 26.03 | V | 103 | NA |
| R | 74 | NA | T | 111 | 25.95 |
| E | 79 | 26.64 | | | |
| A | 80 | 29.61 | | | |
| V | 95E | 42.12 | | | |
| G | 100 | 29.82 | | | |
| K | 103 | 31.10 | | | |
| E | 105 | 25.78 | | | |

F. Molecular Modeling to Determine Which Residues Fall Within 5 Å of a CDR

The molecular model above, generated with the AbM software package, was analyzed to determine which EM164 surface residues were within 5 Å of a CDR. In order to resurface the murine EM164 antibody, all surface residues outside of a CDR should be changed to the human counterpart, but residues within 5 Å of a CDR are treated with special care because they may also contribute to antigen specificity. Therefore, these latter residues must be identified and carefully considered throughout the humanization process. The CDR definitions used for resurfacing combine the AbM definition for heavy chain CDR2 and Kabat definitions for the remaining 5 CDRs (FIG. 14). Table 6 shows the residues that were within 5 Å of any CDR residue in either the light or heavy chain sequence of the EM164 model.

TABLE 6

EM164 antibody framework surface residues within 5Å of a CDR
EM164 Surface Residues within 5Å of a CDR

| Light chain | Heavy chain |
| --- | --- |
| D1 | T28 |
| L3 | K73 |
| T7 | S74 |
| P40 | |
| Q42 | |
| K45 | |
| G57 | |
| D60 | |
| E81 | |

G. Identification of the Most Homologous Human Surfaces

Candidate human antibody surfaces for resurfacing EM164 were identified within the Kabat antibody sequence database using SR software, which provided for the searching of only specified residue positions against the antibody database. To preserve the natural pairings, surface residues of both the light and heavy chains were compared together. The most homologous human surfaces from the Kabat database were aligned in rank order of sequence identity. The top 5 surfaces are given in Table 7. These surfaces were then compared to identify which of them would require the least changes within 5 Å of a CDR. The Leukemic B-cell antibody, CLL 1.69, required the least number of surface residue changes (10 in total) and only two of these residues were within 5 Å of a CDR.

The full length variable region sequence for EM164 was also aligned against the Kabat human antibody database and CLL 1.69 was again identified as the most similar human variable region sequence. Together, these sequence comparisons identified the human Leukemic B-cell antibody CLL 1.69 as the preferred choice as a human surface for EM164.

TABLE 7

| The top 5 human sequences extracted from the Kabat database<br>Most Homologous Human Antibody Surfaces | | |
|---|---|---|
| Antibody | Light Chain | SEQ ID NO: |
| MuEM164 | D L T L L Q P G Q K G D S R E K K R A | 33 |
| CLL1.69 | D V T L L P P G Q R G D A R E K K R - | 34 |
| MSL5 | D Q S L I P P G Q K G D S R D K K R A | 35 |
| CDP571 | D M S S V R P G Q K G S S S D K K R - | 36 |
| LC3aPB | E V S G P R P G Q R G D S R E K K R - | 37 |
| SSbPB | E V S G P R P G Q R G D S R E K K R - | 38 |
| Antibody | Heavy Chain | |
| MuEM164 | Q Q Q A L K P G K K T P G Q E K K R K S S S E A S | 39 |
| CLL1.69 | Q Q V A V K P G K K T P G Q Q K Q G K S S S E Q S | 40 |
| MSL5 | Q Q Q P L K P G K K T P G K D D K G T S N N E Q S | 41 |
| CDP571 | Q Q V A V K P G K K T P G Q Q K K G K S S S E Q S | 42 |
| LC3aPB | - Q V A V K P G K K T P G Q Q K Q G K S S S E Q S | 43 |
| SSbPB | - Q V A V K P G K K T P G Q Q K Q G E S S S E Q S | 44 |

Alignments were generated by SR (Pedersen 1993).
The EM164 surface residues that come within 5Å of a CDR are underlined.

H. Construction of Humanized EM164 Genes

The ten surface residue changes for EM164 (Table 7) were made using PCR mutagenesis techniques as described above. Because eight of the surface residues for CLL 1.69 were not within 5 Å of a CDR, these residues were changed from murine to human in all versions of humanized EM164 (Tables 8 and 9). The two light chain surface residues that were within 5 Å of a CDR (Kabat positions 3 and 45) were either changed to human or were retained as murine. Together, these options generate the four humanized versions of EM164 that were constructed (FIGS. 22 and 23).

Of the four humanized versions, version 1.0 has all 10 human surface residues. The most conservative version with respect to changes in the vicinity of the CDR is version 1.1, which retained both of the murine surface residues that were within 5 Å of a CDR. All four humanized EM164 antibody genes were cloned into an antibody expression plasmid (FIG. 16) for use in transient and stable transfections.

TABLE 8

| Residue changes for versions 1.0-1.3 of humanized EM164 antibody | | | | |
|---|---|---|---|---|
| Changes in all versions | | | | |
| Light Chain: | muQ18 to huP18; | muS67 to huA67 | | |
| Heavy Chain: | muQ5 to huV5; | muL11 to huV11; | muE61 to huQ61; | muK64 to huQ64; |
| | muR65 to huG65; | muA106 to huQ106 | | |

TABLE 8-continued

| Residue changes for versions 1.0-1.3 of humanized EM164 antibody | | | | | |
|---|---|---|---|---|---|
| huEM164 changes | | | | | |
| | Light Chain aa3 | | Light Chain aa45 | | Total 5A |
| | Mu | hu | mu | hu | Mouse Res |
| v1.0 | | V | | R | 0 |
| v1.1 | L | | K | | 2 |
| v1.2 | L | | | R | 1 |
| v1.3 | | V | K | | 1 |

I. Comparison of the Affinities of Humanized EM164 Antibody Versions with Murine EM164 Antibody for Binding to Full-Length IGF-I Receptor and to Truncated IGF-I Receptor Alpha Chain The affinities of the humanized EM164 antibody versions 1.0-1.3 were compared to those of murine EM164 antibody through binding competition assays using biotinylated full-length human IGF-I receptor or myc-epitope tagged truncated IGF-I receptor alpha chain, as described above. Humanized EM164 antibody samples were obtained by transient transfection of the appropriate expression vectors in human embryonic kidney 293T cells, and antibody concentrations were determined by ELISA using purified humanized antibody standards. For ELISA binding competition measurements, mixtures of humanized antibody samples and various concentrations of murine EM164 antibody were incubated with indirectly captured biotinylated full-length IGF-I receptor or myc-epitope tagged truncated IGF-I receptor alpha chain. After equilibration, the bound humanized antibody was detected using a goat-anti-human-Fab'$_2$-antibody-horseradish peroxidase conjugate. Plots of ([bound murine Ab]/[bound humanized Ab]) vs ([murine Ab]/[humanized Ab]), which theoretically yield a straight line with slope= ($K_{d\ humanized\ Ab}/K_{d\ murine\ Ab}$), were used to determine the relative affinities of the humanized and murine antibodies.

Figure 11:
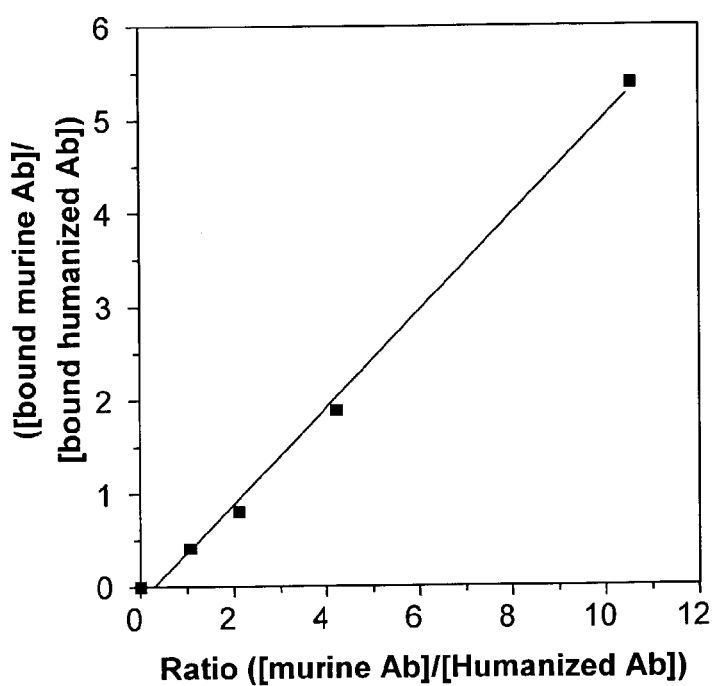
FIG. 11 shows competition between the binding of humanized EM164 antibody (v.1.0) and murine EM164 antibody.
Figure 24:
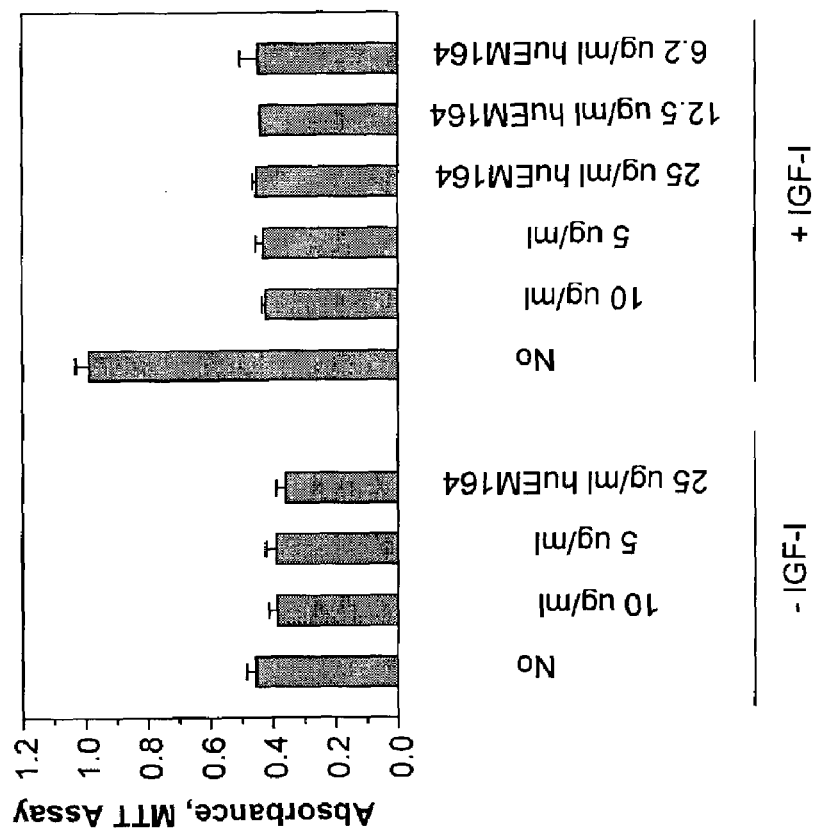
FIG. 24 shows the inhibition of IGF-I-stimulated growth and survival of MCF-7 cells by humanized EM164 v1.0 antibody and murine EM164 antibody.

An exemplary competition assay is shown in FIG. 11. An Immulon-2HB ELISA plate was coated with 100 μL of 5 μg/mL streptavidin per well in carbonate buffer at ambient temperature for 7 h. The streptavidin-coated wells were blocked with 200 μL of blocking buffer (10 mg/mL BSA in TBS-T buffer) for 1 h, washed with TBS-T buffer and incubated with biotinylated IGF-I receptor (5 ng per well) overnight at 4° C. The wells containing indirectly captured biotinylated IGF-I receptor were then washed and incubated with mixtures of humanized EM164 antibody (15.5 ng) and murine antibody (0 ng, or 16.35 ng, or 32.7 ng, or 65.4 ng, or 163.5 ng) in 100 μL blocking buffer for 2 h at ambient temperature and were then incubated overnight at 4° C. The wells were then washed with TBS-T buffer and incubated with goat-anti-human-Fab'$_2$-antibody-horseradish peroxidase conjugate for 1 h (100 μL; 1 μg/mL in blocking buffer), followed by washes and detection using ABTS/$H_2O_2$ substrate at 405 nm. The plot of ([bound murine Ab]/[bound humanized Ab]) vs ([murine Ab]/[humanized Ab]) yielded a straight line ($r^2$=0.996) with slope (=$K_{d\ humanized\ Ab}/K_{d\ murine\ Ab}$) of 0.52. The humanized antibody version 1.0 therefore bound to IGF-I receptor more tightly than did murine EM164 antibody. Similar values for the gradient, ranging from about 0.5 to 0.8, were obtained for competitions of versions 1.0, 1.1, 1.2 and 1.3 of humanized EM164 antibodies with murine EM164 antibody for binding to full-length IGF-I receptor or to truncated IGF-I receptor alpha chain, which indicated that all of the humanized versions of EM 164 antibody had similar affinities, which were all better than that of the parent murine EM164 antibody. A chimeric version of EM164 antibody with 92F→C mutation in heavy chain showed a slope of about 3 in a similar binding competition with murine EM164 antibody, which indicated that the 92F→C mutant of EM 164 had a 3-fold lower affinity than did murine EM164 antibody for binding to IGF-I receptor. The humanized EM164 v1.0 antibody showed a similar inhibition of IGF-I-stimulated growth and survival of MCF-7 cells as did the murine EM164 antibody (FIG. 24). The inhibition of serum-stimulated growth and survival of MCF-7 cells by humanized EM164 v1.0 antibody was similar to the inhibition by murine EM164 antibody.

TABLE 9

The Kabat numbering system is used for the light chain and heavy chain variable region polypeptides of the different versions of the EM164 Ab. The amino acid residues are grouped into Framework (FR) and Complementarity Determining Regions (CDR) according to position in the polypeptide chain.
Taken from Kabat et al. Sequences of Proteins of Immunological Interest, Fifth Edition, 1991, NIH Publication No. 91-3242

| Segment | Light Chain | Heavy Chain |
| --- | --- | --- |
| FR1 | 1-23 (with an occasional residue at 0, and a deletion at 10 in V$_\lambda$ chains) | 1-30 (with an occasional residue at 0) |
| CDR1 | 24-34 (with possible insertions numbered as 27A, B, C, D, E, F) | 31-35 (with possible insertions numbered as 35A, B) |
| FR2 | 35-49 | 36-49 |
| CDR2 | 50-56 | 50-65 (with possible insertions numbered as 52A, B, C) |
| FR3 | 57-88 | 66-94 (with possible insertions numbered as 82A, B, C) |
| CDR3 | 89-97 (with possible insertions numbered as 95A, B, C, D, E, F) | 95-102 (with possible insertions numbered as 100A, B, C, D, E, F, G, H, I, J, K) |
| FR4 | 98-107 (with a possible insertion numbered as 106A) | 103-113 |

J. Process of Providing Improved Anti-IGF-I-Receptor Antibodies Starting from the Murine and Humanized Antibody Sequences Described Herein:

The amino acid and nucleic acid sequences of the anti-IGF-I receptor antibody EM164 and its humanized variants were used to develop other antibodies that have improved properties and that are also within the scope of the present invention. Such improved properties include increased affinity for the IGF-I receptor. Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.*, 254, 392-403; Rader, C. et al., 1998, *Proc. Natl. Acad. Sci. USA*, 95, 8910-8915; Vaughan, T. J. et al., 1998, *Nature Biotechnology*, 16, 535-539).

In these studies, variants of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16, 535-539; Adey, N. B. et al., 1996, Chapter 16, pp. 277-291, in *"Phage Display of Peptides and Proteins"*, Eds. Kay, B. K. et al., Academic Press). These methods of changing the sequence of the primary antibody have resulted, through the use of standard screening techniques, in improved affinities of such secondary antibodies (Gram, H. et al., 1992, *Proc. Natl. Acad. Sci. USA*, 89, 3576-3580; Boder, E. T. et al., 2000, *Proc. Natl. Acad. Sci. USA*, 97, 10701-10705; Davies, J. and Riechmann, L., 1996, *Immunotechnolgy*, 2, 169-179; Thompson, J. et al., 1996, *J. Mol. Biol.*, 256, 77-88; Short, M. K. et al., 2002, *J. Biol. Chem.*, 277, 16365-16370; Furukawa, K. et al., 2001, *J. Biol. Chem.*, 276, 27622-27628).

By a similar directed strategy of changing one or more amino acid residues of the antibody, the antibody sequences described in this invention can be used to develop anti-IGF-I receptor antibodies with improved functions, such as antibodies having suitable groups such as free amino groups or thiols at convenient attachment points for covalent modification for use, for example, in the attachment of therapeutic agents.

K. Alternative Expression System for Murine, Chimeric and Other Anti-IGF-I Receptor Antibodies The murine anti IGF-I receptor antibody was also expressed from mammalian expression plasmids similar to those used to express the humanized antibody (above). Expression plasmids are known that have murine constant regions including the light chain kappa and heavy chain gamma-1 sequences (McLean et al., 2000, *Mol Immunol.*, 37, 837-845). These plasmids were designed to accept any antibody variable region, such as for example the murine anti-IGF-I receptor antibody, by a simple restriction digest and cloning. Additional PCR of the anti-IGF-1 receptor antibody was usually required to create the restriction compatible with those in the expression plasmid.

An alternative approach for expressing the fully murine anti-IGF-I receptor antibody was to replace the human constant regions in the chimeric anti-IGF-I receptor antibody expression plasmid. The chimeric expression plasmid (FIG. 16) was constructed using cassettes for the variable regions and for both the light and heavy chain constant regions. Just as the antibody variable sequences were cloned into this expression plasmid by restriction digests, separate restriction digests were used to clone in any constant region sequences. The kappa light chain and gamma-1 heavy chain cDNAs were cloned, for example, from murine hybridoma RNA, such as the RNA described herein for cloning of the anti-IGF-1 antibody variable regions. Similarly, suitable primers were designed from sequences available in the Kabat database (see Table 10). For example, RT-PCR was used to clone the constant region sequences and to create the restriction sites needed to clone these fragments into the chimeric anti-IGF-I receptor antibody expression plasmid. This plasmid was then used to express the fully murine anti-IGF-I receptor antibody in standard mammalian expression systems such as the CHO cell line.

TABLE 10

Primers designed to clone the murine gamma-1 constant region and murine kappa constant region respectively.
Murine Constant Region Primers

| Primer name | Primer Sequence | SEQ ID NO: |
|---|---|---|
| MuIgG1 C3endX | TTTTGAGCTCTTATTTACCAGGAGAGTG GGAGAGGCTCTT | 45 |
| MuIgG1 C5endH | TTTTAAGCTTGCCAAAACGACACCCCCA TCTGTCTAT | 46 |
| MuIgKap C3endB | TTTTGGATCCTAACACTCATTCCTGTTG AAGC | 47 |
| MuIgKap C5endE | TTTTGAATTCGGGCTGATGCTGCACCAA CTG | 48 |

The primers were designed from sequences available in the Kabat database (Johnson, G and Wu, T. T. (2001) Nucleic Acids Research, 29: 205-206).

STATEMENT OF DEPOSIT

The hybridoma that makes murine EM164 antibody was deposited with the American Type Culture Collection, PO Box 1549, Manassas, Va. 20108, on Jun. 14, 2002, under the Terms of the Budapest Treaty, and assigned deposit number PTA-4457.

Certain patents and printed publications have been referred to in the present disclosure, the teachings of which are hereby each incorporated in their respective entireties by reference.

While the invention has been described in detail and with reference to specific embodiments thereof, it will be apparent to one of skill in the art that various changes and modifications can be made thereto without departing from the spirit and scope thereof.

---

What is claimed is:

1. An isolated antibody or fragment thereof that specifically binds to IGF-IR, comprising at least one heavy chain variable region and at least one light chain variable region, wherein said heavy chain variable region comprises three complementarity-determining regions comprising the amino acid sequences of SEQ ID NOS:1-3, and wherein said light chain variable region comprises three complementarity-determining regions comprising the amino acid sequences of SEQ ID NOS:4-6.

2. An isolated antibody or fragment thereof that specifically binds to IGF-IR, comprising at least one heavy chain variable region and at least one light chain variable region, wherein said heavy chain variable region comprises the amino acid sequence of SEQ ID NO:7.

3. An isolated antibody or fragment thereof that specifically binds to IGF-IR, comprising at least one heavy chain variable region and at least one light chain variable region, wherein said light chain variable comprises the amino acid sequence of SEQ ID NO:8.

4. An antibody or antibody fragment of claim 1, comprising a heavy chain variable region and a light chain variable region, wherein said heavy chain variable region comprises heavy chain complementarity-determining regions comprising the amino acid sequences of SEQ ID NOs:1-3, and wherein said light chain variable region comprises the amino acid sequence of SEQ ID NO:8.

5. An antibody or antibody fragment of claim 1, comprising at least one heavy chain variable region and at least one light chain variable region, wherein said heavy chain variable region comprises three complementarity-determining regions comprising the amino acid sequences of SEQ ID NOS:1-3, and wherein said light chain variable region comprises three complementarity-determining regions comprising the amino acid sequences of SEQ ID NOS:4-6, respectively, and wherein said heavy chain variable region comprises SEQ ID NO:7.

6. The antibody or fragment thereof of claim 1, comprising a light chain variable region having a sequence selected from the group consisting of
SEQ ID NO:9,
SEQ ID NO:10,
SEQ ID NO:11 and
SEQ ID NO:12.

7. The antibody or fragment thereof of claim 1, comprising a heavy chain variable region comprising the amino acid sequence of SEQ ID NO:13.

8. A pharmaceutical composition comprising the antibody or antibody fragment of claim 1 and a pharmaceutically acceptable carrier.

9. A conjugate comprising the antibody or antibody fragment of claim 1 linked to a cytotoxic agent.

10. The conjugate of claim 9, wherein said cytotoxic agent is selected from the group consisting of a maytansinoid, a small drug, a prodrug, a taxoid, CC-1065 and a CC-1065 analog.

11. A pharmaceutical composition comprising the conjugate of claim 10 and a pharmaceutically acceptable carrier.

12. A diagnostic reagent comprising the composition of claim 8, wherein said antibody or antibody fragment is labeled with a detectable moiety.

13. The diagnostic reagent of claim 12, wherein said detectable moiety is selected from the group consisting of a radiolabel, a fluorophore, a chromophore, an imaging agent and a metal ion.

14. A murine antibody EM164 (ATCC deposit number PTA-4457) or an epitope-binding fragment thereof that specifically binds to an insulin-like growth factor-I receptor, wherein said antibody or epitope-binding fragment is an antagonist of said receptor and is devoid of agonist activity toward said receptor.

15. A humanized or resurfaced antibody EM164 or an epitope-binding fragment thereof that specifically binds to an insulin-like growth factor-I receptor, wherein said antibody or fragment is an antagonist of said receptor and is devoid of agonist activity toward said receptor.

16. The antibody or fragment of claim 1, which specifically binds to a human insulin-like growth factor-I receptor.

17. A hybridoma cell line EM164 on deposit with the American Type Culture Collection as Accession Number PTA-4457.

18. The antibody or antibody fragment according to claim 1, wherein the antibody or antibody fragment has at least one property selected from the group consisting of:
- a) inhibits cellular function of a IGF-IR without activating said IGF-IR; and
- b) inhibits tumor cell growth in the presence of serum by at least 80%.

19. The antibody or antibody fragment according to claim 18, wherein the antibody or antibody fragment has all of said properties.

20. An isolated humanized antibody or epitope-binding antibody fragment that specifically binds to IGF-IR, comprising at least one heavy chain variable region and at least one light chain variable region, wherein said heavy chain variable region comprises three complementarity-determining regions comprising the amino acid sequences of SEQ ID NOS:1-3, and wherein said light chain variable region comprising a sequence selected from the group consisting of SEQ ID NO:9; SEQ ID NO:10; SEQ ID NO:11; SEQ ID NO:12; SEQ ID NO:83; SEQ ID NO:84; SEQ ID NO:85, and SEQ ID NO:86.

21. An isolated humanized antibody or epitope-binding antibody fragment that specifically binds to IGF-IR, comprising at least one heavy chain variable region and at least one light chain variable region, wherein said light chain variable region comprises three complementarity-determining regions comprising the amino acid sequences of SEQ ID NOS:4-6, and wherein said heavy chain variable region comprises a sequence selected from the group consisting of SEQ ID NO:13; and SEQ ID NO:88.

22. A method for inhibiting the growth of a cancer cell expressing IGF-IR comprising contacting said cell with the antibody or antibody fragment of claim 1.

23. A method for treating a patient having a cancer expressing IGF-IR comprising administering to said patient an effective amount of the antibody or antibody fragment of claim 1.

24. The method of claim 23 further comprising administering to said patient a therapeutic agent.

25. The method of claim 24 wherein said therapeutic agent is a cytotoxic agent.

26. A method for treating a patient having a cancer expressing IGF-IR comprising administering to said patient an effective amount of the conjugate of claim 9.

27. The method of treatment of claim 23, wherein said cancer is a cancer selected from the group consisting of breast cancer, colon cancer, ovarian carcinoma, osteosarcoma, cervical cancer, prostate cancer, lung cancer, synovial carcinoma and pancreatic cancer.

28. A method for diagnosing a subject suspect of having a cancer expressing IGF-IR, said method comprising:
- administering to said subject the diagnostic reagent of claim 12; and
- detecting the distribution of said reagent within said subject.

29. The method of diagnosis of claim 28, wherein said cancer is a cancer selected from the group consisting of breast cancer, colon cancer, ovarian carcinoma, osteosarcoma, cervical cancer, prostate cancer, lung cancer, synovial carcinoma and pancreatic cancer.

* * * * *

SEQUENCE LISTING

```
<160> NUMBER OF SEQ ID NOS: 98

<210> SEQ ID NO 1
<211> LENGTH: 5
<212> TYPE: PRT
<213> ORGANISM: Artificial Sequence
<220> FEATURE:
<223> OTHER INFORMATION: antibody heavy chain complementarity
      determining region

<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: antibody heavy chain complementarity
      determining region

<400> SEQUENCE: 2

Glu Ile Asn Pro Ser Asn Gly Arg Thr Asn Tyr Asn Glu Lys Phe Lys
1               5                   10                  15
```

-continued

```
Arg

<210> SEQ ID NO 3
<211> LENGTH: 15
<212> TYPE: PRT
<213> ORGANISM: Artificial Sequence
<220> FEATURE:
<223> OTHER INFORMATION: antibody heavy chain complementarity
      determining region

<400> SEQUENCE: 3

Gly Arg Pro Asp Tyr Tyr Gly Ser Ser Lys Trp Tyr Phe Asp Val
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: antibody light chain complementarity
      determining region

<400> SEQUENCE: 4

Arg Ser Ser Gln Ser Ile Val His Ser Asn Val Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: antibody light chain complementarity
      determining region

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: antibody light chain complementarity
      determining region

<400> SEQUENCE: 6

Phe Gln Gly Ser His Val Pro Pro Thr
1               5

<210> SEQ ID NO 7
<211> LENGTH: 124
<212> TYPE: PRT
<213> ORGANISM: Artificial Sequence
<220> FEATURE:
<223> OTHER INFORMATION: antibody heavy chain

<400> SEQUENCE: 7

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
```

```
                50                  55                  60
Lys Arg Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Phe
                 85                  90                  95

Ala Arg Gly Arg Pro Asp Tyr Tyr Gly Ser Ser Lys Trp Tyr Phe Asp
                100                 105                 110

Val Trp Gly Ala Gly Thr Thr Val Thr Val Ser Ser
            115                 120

<210> SEQ ID NO 8
<211> LENGTH: 113
<212> TYPE: PRT
<213> ORGANISM: Artificial Sequence
<220> FEATURE:
<223> OTHER INFORMATION: antibody light chain

<400> SEQUENCE: 8

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Val Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg

<210> SEQ ID NO 9
<211> LENGTH: 113
<212> TYPE: PRT
<213> ORGANISM: Artificial Sequence
<220> FEATURE:
<223> OTHER INFORMATION: humanized light chain variable region

<400> SEQUENCE: 9

Asp Val Val Met Thr Gln Thr Pro Leu Ser Leu Pro Val Ser Leu Gly
 1               5                  10                  15

Asp Pro Ala Ser Ile Ser Cys Arg Ser Ser Gln Ser Ile Val His Ser
                20                  25                  30

Asn Val Asn Thr Tyr Leu Glu Trp Tyr Leu Gln Lys Pro Gly Gln Ser
             35                  40                  45

Pro Arg Leu Leu Ile Tyr Lys Val Ser Asn Arg Phe Ser Gly Val Pro
         50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg
```

<210> SEQ ID NO 10
<211> LENGTH: 113
<212> TYPE: PRT
<213> ORGANISM: Artificial Sequence
<220> FEATURE:
<223> OTHER INFORMATION: humanized light chain variable region

<400> SEQUENCE: 10

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 11
<211> LENGTH: 113
<212> TYPE: PRT
<213> ORGANISM: Artificial Sequence
<220> FEATURE:
<223> OTHER INFORMATION: humanized light chain variable region

<400> SEQUENCE: 11

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 12
<211> LENGTH: 113
<212> TYPE: PRT
<213> ORGANISM: Artificial Sequence
<220> FEATURE:
<223> OTHER INFORMATION: humanized light chain variable region

<400> SEQUENCE: 12

```
Asp Val Val Met Thr Gln Thr Pro Leu Ser Leu Pro Val Ser Leu Gly
1               5                   10                  15
```

```
Asp Pro Ala Ser Ile Ser Cys Arg Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 13
<211> LENGTH: 124
<212> TYPE: PRT
<213> ORGANISM: Artificial Sequence
<220> FEATURE:
<223> OTHER INFORMATION: humanized heavy chain variable region

<400> SEQUENCE: 13

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Gln Lys Phe
    50                  55                  60

Gln Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser Ser
        115                 120

<210> SEQ ID NO 14
<211> LENGTH: 46
<212> TYPE: DNA
<213> ORGANISM: Artificial Sequence
<220> FEATURE:
<223> OTHER INFORMATION: degenerate 3' light chain PCR primer - HindKL

<400> SEQUENCE: 14
tatagagctc aagcttggat ggtgggaaga tggatacagt tggtgc                    46

<210> SEQ ID NO 15
<211> LENGTH: 36
<212> TYPE: DNA
<213> ORGANISM: Artificial Sequence
<220> FEATURE:
<223> OTHER INFORMATION: degenerate 3' heavy chain PCR primer- Bgl2IgG1

<400> SEQUENCE: 15
ggaagatcta tagacagatg ggggtgtcgt tttggc                               36
```

-continued

```
<210> SEQ ID NO 16
<211> LENGTH: 30
<212> TYPE: DNA
<213> ORGANISM: Artificial Sequence
<220> FEATURE:
<223> OTHER INFORMATION: poly C 5' PCR primer - EcoPolyC

<400> SEQUENCE: 16
tatatctaga attccccccc cccccccccc                                          30

<210> SEQ ID NO 17
<211> LENGTH: 32
<212> TYPE: DNA
<213> ORGANISM: Artificial Sequence
<220> FEATURE:
<223> OTHER INFORMATION: degenerate 5' light chain PCR primer - Sac1MK

<400> SEQUENCE: 17
gggagctcga yattgtgmts acmcarwctm ca                                       32

<210> SEQ ID NO 18
<211> LENGTH: 32
<212> TYPE: DNA
<213> ORGANISM: Artificial Sequence
<220> FEATURE:
<223> OTHER INFORMATION: degenerate 5' heavy chain PCR primer - EcoR1MH1
<220> FEATURE:
<221> NAME/KEY: misc_feature
<222> LOCATION: (18)..(18)
<223> OTHER INFORMATION: "n" may be any nucleic acid

<400> SEQUENCE: 18
cttccggaat tcsargtnma gctgsagsag tc                                       32

<210> SEQ ID NO 19
<211> LENGTH: 35
<212> TYPE: DNA
<213> ORGANISM: Artificial Sequence
<220> FEATURE:
<223> OTHER INFORMATION: degenerate 5' heavy chain PCR primer - EcoR1MH2
<220> FEATURE:
<221> NAME/KEY: misc_feature
<222> LOCATION: (18)..(18)
<223> OTHER INFORMATION: "n" may be any nucleotide

<400> SEQUENCE: 19
cttccggaat tcsargtnma gctgsagsag tcwgg                                    35

<210> SEQ ID NO 20
<211> LENGTH: 10
<212> TYPE: PRT
<213> ORGANISM: Mus musculus

<400> SEQUENCE: 20

Asp Val Leu Met Thr Gln Thr Pro Leu Ser
1               5                   10

<210> SEQ ID NO 21
<211> LENGTH: 10
<212> TYPE: PRT
<213> ORGANISM: Mus musculus

<400> SEQUENCE: 21

Gly Arg Pro Asp Tyr Tyr Gly Ser Ser Lys
1               5                   10
```

<210> SEQ ID NO 22
<211> LENGTH: 24
<212> TYPE: PRT
<213> ORGANISM: Mus musculus

<400> SEQUENCE: 22

Ser Ser Ser Thr Ala Tyr Met Gln Leu Ser Ser Leu Thr Ser Glu Asp
1               5                   10                  15

Ser Ala Val Tyr Tyr Phe Ala Arg
            20

<210> SEQ ID NO 23
<211> LENGTH: 57
<212> TYPE: DNA
<213> ORGANISM: Artificial Sequence
<220> FEATURE:
<223> OTHER INFORMATION: PCR primer

<400> SEQUENCE: 23
caggtgtaca ctcccaggtc caactggtgc agtctggggc tgaagtggtg aagcctg           57

<210> SEQ ID NO 24
<211> LENGTH: 29
<212> TYPE: DNA
<213> ORGANISM: Artificial Sequence
<220> FEATURE:
<223> OTHER INFORMATION: PCR primer

<400> SEQUENCE: 24
caatcagaag ttccagggga aggccacac                                         29

<210> SEQ ID NO 25
<211> LENGTH: 34
<212> TYPE: DNA
<213> ORGANISM: Artificial Sequence
<220> FEATURE:
<223> OTHER INFORMATION: PCR primer

<400> SEQUENCE: 25
ccttcccctg gaacttctga ttgtagttag tacg                                   34

<210> SEQ ID NO 26
<211> LENGTH: 37
<212> TYPE: DNA
<213> ORGANISM: Artificial Sequence
<220> FEATURE:
<223> OTHER INFORMATION: PCR primer

<400> SEQUENCE: 26
caggtgtaca ctccgatgtt gtgatgaccc aaactcc                                37

<210> SEQ ID NO 27
<211> LENGTH: 37
<212> TYPE: DNA
<213> ORGANISM: Artificial Sequence
<220> FEATURE:
<223> OTHER INFORMATION: PCR primer

<400> SEQUENCE: 27
caggtgtaca ctccgatgtt ttgatgaccc aaactcc                                37

<210> SEQ ID NO 28
<211> LENGTH: 39
<212> TYPE: DNA
<213> ORGANISM: Artificial Sequence
<220> FEATURE:

-continued

```
<223> OTHER INFORMATION: PCR primer

<400> SEQUENCE: 28
gactagatct gcaagagatg gaggctggat ctccaagac                               39

<210> SEQ ID NO 29
<211> LENGTH: 35
<212> TYPE: DNA
<213> ORGANISM: Artificial Sequence
<220> FEATURE:
<223> OTHER INFORMATION: PCR primer

<400> SEQUENCE: 29
ttgcagatct agtcagagca tagtacatag taatg                                  35

<210> SEQ ID NO 30
<211> LENGTH: 48
<212> TYPE: DNA
<213> ORGANISM: Artificial Sequence
<220> FEATURE:
<223> OTHER INFORMATION: PCR primer

<400> SEQUENCE: 30
gaatggtacc tgcagaaacc aggccagtct ccaaggctcc tgatctac                     48

<210> SEQ ID NO 31
<211> LENGTH: 28
<212> TYPE: DNA
<213> ORGANISM: Artificial Sequence
<220> FEATURE:
<223> OTHER INFORMATION: PCR primer

<400> SEQUENCE: 31
gtggcagtgg agcagggaca gatttcac                                          28

<210> SEQ ID NO 32
<211> LENGTH: 28
<212> TYPE: DNA
<213> ORGANISM: Artificial Sequence
<220> FEATURE:
<223> OTHER INFORMATION: PCR primer

<400> SEQUENCE: 32
gaaatctgtc cctgctccac tgccactg                                          28

<210> SEQ ID NO 33
<211> LENGTH: 19
<212> TYPE: PRT
<213> ORGANISM: Homo sapiens

<400> SEQUENCE: 33

Asp Leu Thr Leu Leu Gln Pro Gly Gln Lys Gly Asp Ser Arg Glu Lys
1               5                   10                  15

Lys Arg Ala

<210> SEQ ID NO 34
<211> LENGTH: 18
<212> TYPE: PRT
<213> ORGANISM: Homo sapiens

<400> SEQUENCE: 34

Asp Val Thr Leu Leu Pro Pro Gly Gln Arg Gly Asp Ala Arg Glu Lys
1               5                   10                  15

Lys Arg
```

-continued

<210> SEQ ID NO 35
<211> LENGTH: 19
<212> TYPE: PRT
<213> ORGANISM: Homo sapiens

<400> SEQUENCE: 35

Asp Gln Ser Leu Ile Pro Pro Gly Gln Lys Gly Asp Ser Arg Asp Lys
1               5                   10                  15

Lys Arg Ala

<210> SEQ ID NO 36
<211> LENGTH: 18
<212> TYPE: PRT
<213> ORGANISM: Homo sapiens

<400> SEQUENCE: 36

Asp Met Ser Ser Val Arg Pro Gly Gln Lys Gly Ser Ser Ser Asp Lys
1               5                   10                  15

Lys Arg

<210> SEQ ID NO 37
<211> LENGTH: 18
<212> TYPE: PRT
<213> ORGANISM: Homo sapiens

<400> SEQUENCE: 37

Glu Val Ser Gly Pro Arg Pro Gly Gln Arg Gly Asp Ser Arg Glu Lys
1               5                   10                  15

Lys Arg

<210> SEQ ID NO 38
<211> LENGTH: 18
<212> TYPE: PRT
<213> ORGANISM: Homo sapiens

<400> SEQUENCE: 38

Glu Val Ser Gly Pro Arg Pro Gly Gln Arg Gly Asp Ser Arg Glu Lys
1               5                   10                  15

Lys Arg

<210> SEQ ID NO 39
<211> LENGTH: 25
<212> TYPE: PRT
<213> ORGANISM: Homo sapiens

<400> SEQUENCE: 39

Gln Gln Gln Ala Leu Lys Pro Gly Lys Lys Thr Pro Gly Gln Glu Lys
1               5                   10                  15

Lys Arg Lys Ser Ser Ser Glu Ala Ser
                20                  25

<210> SEQ ID NO 40
<211> LENGTH: 25
<212> TYPE: PRT
<213> ORGANISM: Homo sapiens

<400> SEQUENCE: 40

Gln Gln Val Ala Val Lys Pro Gly Lys Lys Thr Pro Gly Gln Gln Lys
1               5                   10                  15

Gln Gly Lys Ser Ser Ser Glu Gln Ser

<210> SEQ ID NO 41
<211> LENGTH: 25
<212> TYPE: PRT
<213> ORGANISM: Homo sapiens

<400> SEQUENCE: 41

Gln Gln Gln Pro Leu Lys Pro Gly Lys Lys Thr Pro Gly Lys Asp Asp
1               5                   10                  15

Lys Gly Thr Ser Asn Asn Glu Gln Ser
            20                  25

<210> SEQ ID NO 42
<211> LENGTH: 25
<212> TYPE: PRT
<213> ORGANISM: Homo sapiens

<400> SEQUENCE: 42

Gln Gln Val Ala Val Lys Pro Gly Lys Lys Thr Pro Gly Gln Gln Lys
1               5                   10                  15

Lys Gly Lys Ser Ser Ser Glu Gln Ser
            20                  25

<210> SEQ ID NO 43
<211> LENGTH: 24
<212> TYPE: PRT
<213> ORGANISM: Homo sapiens

<400> SEQUENCE: 43

Gln Val Ala Val Lys Pro Gly Lys Lys Thr Pro Gly Gln Gln Lys Gln
1               5                   10                  15

Gly Lys Ser Ser Ser Glu Gln Ser
            20

<210> SEQ ID NO 44
<211> LENGTH: 24
<212> TYPE: PRT
<213> ORGANISM: Homo sapiens

<400> SEQUENCE: 44

Gln Val Ala Val Lys Pro Gly Lys Lys Thr Pro Gly Gln Gln Lys Gln
1               5                   10                  15

Gly Glu Ser Ser Ser Glu Gln Ser
            20

<210> SEQ ID NO 45
<211> LENGTH: 40
<212> TYPE: DNA
<213> ORGANISM: Artificial Sequence
<220> FEATURE:
<223> OTHER INFORMATION: PCR primer

<400> SEQUENCE: 45
ttttgagctc ttatttacca ggagagtggg agaggctctt                     40

<210> SEQ ID NO 46
<211> LENGTH: 37
<212> TYPE: DNA
<213> ORGANISM: Artificial Sequence
<220> FEATURE:
<223> OTHER INFORMATION: PCR primer

<400> SEQUENCE: 46

```
tttttaagctt gccaaaacga cacccccatc tgtctat                                37
```

<210> SEQ ID NO 47
<211> LENGTH: 32
<212> TYPE: DNA
<213> ORGANISM: Artificial Sequence
<220> FEATURE:
<223> OTHER INFORMATION: PCR primer

<400> SEQUENCE: 47

```
ttttggatcc taacactcat tcctgttgaa gc                                     32
```

<210> SEQ ID NO 48
<211> LENGTH: 31
<212> TYPE: DNA
<213> ORGANISM: Artificial Sequence
<220> FEATURE:
<223> OTHER INFORMATION: PCR primer

<400> SEQUENCE: 48

```
ttttgaattc gggctgatgc tgcaccaact g                                      31
```

<210> SEQ ID NO 49
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 49

```
atg aag ttg cct gtt agg ctg ttg gtg ctg atg ttc tgg att cct gct         48
Met Lys Leu Pro Val Arg Leu Leu Val Leu Met Phe Trp Ile Pro Ala
1               5                   10                  15 tcc agt agt gat gtt ttg atg acc caa act cca ctc tcc ctg cct gtc         96
Ser Ser Ser Asp Val Leu Met Thr Gln Thr Pro Leu Ser Leu Pro Val
            20                  25                  30 agt ctt gga gat caa gcc tcc atc tct tgc aga tct agt cag agc att        144
Ser Leu Gly Asp Gln Ala Ser Ile Ser Cys Arg Ser Ser Gln Ser Ile
        35                  40                  45 gta cat agt aat gta aac acc tat tta gaa tgg tac ctg cag aaa cca        192
Val His Ser Asn Val Asn Thr Tyr Leu Glu Trp Tyr Leu Gln Lys Pro
    50                  55                  60 ggc cag tct cca aag ctc ctg atc tac aaa gtt tcc aac cga ttt tct        240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg aca gat ttc aca        288
Gly Val Pro Asp Arg Phe Ser Gly Ser Gly Ser Gly Thr Asp Phe Thr
                85                  90                  95 ctc agg atc agc aga gtg gag gct gag gat ctg gga att tat tac tgc        336
Leu Arg Ile Ser Arg Val Glu Ala Glu Asp Leu Gly Ile Tyr Tyr Cys
            100                 105                 110 ttt caa ggt tca cat gtt cct ccg acg ttc ggt gga ggc acc aag ctg        384
Phe Gln Gly Ser His Val Pro Pro Thr Phe Gly Gly Gly Thr Lys Leu
        115                 120                 125 gaa atc aaa cgg                                                        396
Glu Ile Lys Arg
    130
```

<210> SEQ ID NO 50
<211> LENGTH: 132
<212> TYPE: PRT
<213> ORGANISM: Mus musculus

<400> SEQUENCE: 50

```
Met Lys Leu Pro Val Arg Leu Leu Val Leu Met Phe Trp Ile Pro Ala
1               5                   10                  15
Ser Ser Ser Asp Val Leu Met Thr Gln Thr Pro Leu Ser Leu Pro Val
            20                  25                  30
Ser Leu Gly Asp Gln Ala Ser Ile Ser Cys Arg Ser Ser Gln Ser Ile
        35                  40                  45
Val His Ser Asn Val Asn Thr Tyr Leu Glu Trp Tyr Leu Gln Lys Pro
    50                  55                  60
Gly Gln Ser Pro Lys Leu Leu Ile Tyr Lys Val Ser Asn Arg Phe Ser
65                  70                  75                  80
Gly Val Pro Asp Arg Phe Ser Gly Ser Gly Ser Gly Thr Asp Phe Thr
                85                  90                  95
Leu Arg Ile Ser Arg Val Glu Ala Glu Asp Leu Gly Ile Tyr Tyr Cys
            100                 105                 110
Phe Gln Gly Ser His Val Pro Pro Thr Phe Gly Gly Gly Thr Lys Leu
        115                 120                 125
Glu Ile Lys Arg
        130
```

<210> SEQ ID NO 51
<211> LENGTH: 429
<212> TYPE: DNA
<213> ORGANISM: Mus musculus
<220> FEATURE:
<221> NAME/KEY: CDS
<222> LOCATION: (1)..(429)

<400> SEQUENCE: 51

```
atg gga tgg agc tat atc atc ctc ttt ttg gta gca aca gct aca gaa      48
Met Gly Trp Ser Tyr Ile Ile Leu Phe Leu Val Ala Thr Ala Thr Glu
1               5                   10                  15 gtc cac tcc cag gtc caa ctg cag cag tct ggg gct gaa ctg gtg aag      96
Val His Ser Gln Val Gln Leu Gln Gln Ser Gly Ala Glu Leu Val Lys
            20                  25                  30 cct ggg gct tca gtg aag ctg tcc tgt aag gct tct ggc tac acc ttc     144
Pro Gly Ala Ser Val Lys Leu Ser Cys Lys Ala Ser Gly Tyr Thr Phe
        35                  40                  45 acc agc tac tgg atg cac tgg gtg aag cag agg cct gga caa ggc ctt     192
Thr Ser Tyr Trp Met His Trp Val Lys Gln Arg Pro Gly Gln Gly Leu
    50                  55                  60 gag tgg att gga gag att aat cct agc aac ggt cgt act aac tac aat     240
Glu Trp Ile Gly Glu Ile Asn Pro Ser Asn Gly Arg Thr Asn Tyr Asn
65                  70                  75                  80 gag aag ttc aag agg aag gcc aca ctg act gta gac aaa tcc tcc agc     288
Glu Lys Phe Lys Arg Lys Ala Thr Leu Thr Val Asp Lys Ser Ser Ser
                85                  90                  95 aca gcc tac atg caa ctc agc agc ctg aca tct gag gac tct gcg gtc     336
Thr Ala Tyr Met Gln Leu Ser Ser Leu Thr Ser Glu Asp Ser Ala Val
            100                 105                 110 tat tac ttt gca aga gga aga cca gat tac tac ggt agt agc aag tgg     384
Tyr Tyr Phe Ala Arg Gly Arg Pro Asp Tyr Tyr Gly Ser Ser Lys Trp
        115                 120                 125 tac ttc gat gtc tgg ggc gca ggg acc acg gtc acc gtc tcc tca         429
Tyr Phe Asp Val Trp Gly Ala Gly Thr Thr Val Thr Val Ser Ser
    130                 135                 140
```

<210> SEQ ID NO 52

```
<211> LENGTH: 143
<212> TYPE: PRT
<213> ORGANISM: Mus musculus

<400> SEQUENCE: 52

Met Gly Trp Ser Tyr Ile Ile Leu Phe Leu Val Ala Thr Ala Thr Glu
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asn Pro Ser Asn Gly Arg Thr Asn Tyr Asn
65                  70                  75                  80

Glu Lys Phe Lys Arg Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Phe Ala Arg Gly Arg Pro Asp Tyr Tyr Gly Ser Ser Lys Trp
        115                 120                 125

Tyr Phe Asp Val Trp Gly Ala Gly Thr Thr Val Thr Val Ser Ser
    130                 135                 140

<210> SEQ ID NO 53
<211> LENGTH: 10
<212> TYPE: PRT
<213> ORGANISM: Mus musculus

<400> SEQUENCE: 53

Gly Tyr Thr Phe Thr Ser Tyr Trp Met His
1               5                   10

<210> SEQ ID NO 54
<211> LENGTH: 10
<212> TYPE: PRT
<213> ORGANISM: Mus musculus

<400> SEQUENCE: 54

Glu Ile Asn Pro Ser Asn Gly Arg Thr Asn
1               5                   10

<210> SEQ ID NO 55
<211> LENGTH: 15
<212> TYPE: PRT
<213> ORGANISM: Mus musculus

<400> SEQUENCE: 55

Gly Arg Pro Asp Tyr Tyr Gly Ser Ser Lys Trp Tyr Phe Asp Val
1               5                   10                  15

<210> SEQ ID NO 56
<211> LENGTH: 100
<212> TYPE: PRT
<213> ORGANISM: Mus musculus

<400> SEQUENCE: 56

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30
```

```
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
            100

<210> SEQ ID NO 57
<211> LENGTH: 98
<212> TYPE: PRT
<213> ORGANISM: Mus musculus

<400> SEQUENCE: 57

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg

<210> SEQ ID NO 58
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 58

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 59
```

<211> LENGTH: 113
<212> TYPE: PRT
<213> ORGANISM: Artificial Sequence
<220> FEATURE:
<223> OTHER INFORMATION: synthetic antibody structure

<400> SEQUENCE: 59

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Ser Ile Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gln Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 60
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 60

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr His Ala Pro Tyr Thr Phe Gly Gly Gly Thr Lys Leu Glu Ile Lys
            100                 105                 110

Arg

<210> SEQ ID NO 61
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 61

Asp Ile Glu Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

```
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
                100                 105                 110
Arg

<210> SEQ ID NO 62
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 62

Asp Val Leu Met Thr Gln Thr Pro Leu Ser Leu Pro Val Ser Leu Gly
 1               5                  10                  15

Asp Gln Ala Ser Ile Ser Cys Arg Phe Ser Gln Ser Ile Val His Ser
                 20                  25                  30

Asn Gly Asn Thr Tyr Leu Glu Trp Tyr Leu Gln Lys Ser Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Arg Thr Phe Gly Gly Gly Thr Lys Leu Glu Ile Lys
                100                 105                 110
Arg

<210> SEQ ID NO 63
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 63

Glu Leu Val Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
                 20                  25                  30

Asn Gly Asp Thr Tyr Leu Asp Trp Phe Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95
```

```
Ser His Val Pro Pro Thr Phe Gly Gly Gly Thr Lys Leu Glu Ile Lys
            100                 105                 110
Arg

<210> SEQ ID NO 64
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 64

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Leu Leu Ser
            20                  25                  30

Asp Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Gln Gln Gly
                85                  90                  95

Ser His Val Pro Pro Thr Phe Gly Gly Gly Thr Lys Leu Glu Ile Lys
            100                 105                 110
Arg

<210> SEQ ID NO 65
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 65

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Ser Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Phe Thr Phe Gly Ser Gly Thr Lys Leu Glu Ile Lys
            100                 105                 110
Arg

<210> SEQ ID NO 66
<211> LENGTH: 113
<212> TYPE: PRT
<213> ORGANISM: Artificial Sequence
<220> FEATURE:
<223> OTHER INFORMATION: synthetic antibody structure
```

```
<400> SEQUENCE: 66

Asp Val Leu Met Thr Gln Ile Pro Val Ser Leu Pro Val Ser Leu Gly
1               5                   10                  15

Asp Gln Ala Ser Ile Ser Cys Arg Ser Ser Gln Ile Ile Val His Asn
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg

<210> SEQ ID NO 67
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 67

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Ala Pro Arg Thr Phe Gly Gly Gly Thr Lys Leu Glu Ile Lys
            100                 105                 110

Arg

<210> SEQ ID NO 68
<211> LENGTH: 113
<212> TYPE: PRT
<213> ORGANISM: Artificial Sequence
<220> FEATURE:
<223> OTHER INFORMATION: synthetic antibody structure

<400> SEQUENCE: 68

Asp Val Leu Met Thr Gln Ile Pro Val Ser Leu Pro Val Ser Leu Gly
1               5                   10                  15

Asp Gln Ala Ser Ile Ser Cys Arg Ser Ser Gln Ile Ile Val His Asn
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
            100                 105                 110

Arg

<210> SEQ ID NO 69
<211> LENGTH: 113
<212> TYPE: PRT
<213> ORGANISM: Artificial Sequence
<220> FEATURE:
<223> OTHER INFORMATION: synthetic antibody structure
<220> FEATURE:
<221> NAME/KEY: MISC_FEATURE
<222> LOCATION: (28)..(28)
<223> OTHER INFORMATION: "X" may be any amino acid
<220> FEATURE:
<221> NAME/KEY: MISC_FEATURE
<222> LOCATION: (101)..(101)
<223> OTHER INFORMATION: "X" may be any amino acid

<400> SEQUENCE: 69

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Xaa Ile Val His Ser
                20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Xaa Thr Phe Gly Gly Gly Thr Lys Leu Glu Ile Lys
            100                 105                 110

Arg

<210> SEQ ID NO 70
<211> LENGTH: 124
<212> TYPE: PRT
<213> ORGANISM: Artificial Sequence
<220> FEATURE:
<223> OTHER INFORMATION: synthetic antibody structure

<400> SEQUENCE: 70

Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
             35                  40                  45

Gly Glu Ile Asn Pro Ser Asn Gly Arg Thr Asn Tyr Asn Glu Lys Phe
         50                  55                  60

Lys Arg Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Phe
```

```
                    85                  90                  95
Ala Arg Gly Arg Pro Asp Tyr Tyr Gly Ser Ser Lys Trp Tyr Phe Asp
                100                 105                 110

Val Trp Gly Ala Gly Thr Thr Val Thr Val Ser Ser
            115                 120

<210> SEQ ID NO 71
<211> LENGTH: 120
<212> TYPE: PRT
<213> ORGANISM: Artificial Sequence
<220> FEATURE:
<223> OTHER INFORMATION: synthetic antibody structure

<400> SEQUENCE: 71

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Arg Gly Leu Glu Trp Ile
            35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
                100                 105                 110

Gly Thr Thr Val Thr Val Ser Ser
            115                 120

<210> SEQ ID NO 72
<211> LENGTH: 120
<212> TYPE: PRT
<213> ORGANISM: Artificial Sequence
<220> FEATURE:
<223> OTHER INFORMATION: synthetic antibody structure

<400> SEQUENCE: 72

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Arg Gly Leu Glu Trp Ile
            35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
                100                 105                 110

Gly Thr Thr Leu Thr Val Ser Ser
            115                 120

<210> SEQ ID NO 73
<211> LENGTH: 122
```

<212> TYPE: PRT
<213> ORGANISM: Artificial Sequence
<220> FEATURE:
<223> OTHER INFORMATION: synthetic antibody structure

<400> SEQUENCE: 73

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Gly Pro Gly Gln Gly Leu Glu Trp Ile
        35                  40                  45

Gly Glu Ile Asp Pro Ser Asp Ser Tyr Pro Asn Tyr Asn Glu Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Leu Tyr Tyr Tyr Gly Thr Ser Tyr Gly Val Leu Asp Tyr Trp
            100                 105                 110

Gly Gln Gly Thr Ser Val Thr Val Ser Ser
        115                 120
```

<210> SEQ ID NO 74
<211> LENGTH: 120
<212> TYPE: PRT
<213> ORGANISM: Artificial Sequence
<220> FEATURE:
<223> OTHER INFORMATION: synthetic antibody structure

<400> SEQUENCE: 74

```
Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Ala Lys Gln Arg Pro Gly Gln Gly Leu Glu Trp Ile
        35                  40                  45

Gly Glu Ile His Pro Asn Ser Gly Asn Thr Asn Tyr Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Trp Arg Tyr Gly Ser Pro Tyr Tyr Phe Asp Tyr Trp Gly Gln
            100                 105                 110

Gly Thr Thr Leu Thr Val Ser Ser
        115                 120
```

<210> SEQ ID NO 75
<211> LENGTH: 118
<212> TYPE: PRT
<213> ORGANISM: Artificial Sequence
<220> FEATURE:
<223> OTHER INFORMATION: synthetic antibody structure

<400> SEQUENCE: 75

```
Gln Val Gln Phe Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
```

```
                    20                  25                  30
Leu Met His Trp Ile Lys Gln Arg Pro Gly Arg Gly Leu Glu Trp Ile
            35                  40                  45

Gly Arg Ile Asp Pro Asn Asn Val Val Thr Lys Phe Asn Glu Lys Phe
        50                  55                  60

Lys Ser Lys Ala Thr Leu Thr Val Asp Lys Pro Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Tyr Ala Tyr Cys Arg Pro Met Asp Tyr Trp Gly Gln Gly Thr
            100                 105                 110

Thr Val Thr Val Ser Ser
        115

<210> SEQ ID NO 76
<211> LENGTH: 117
<212> TYPE: PRT
<213> ORGANISM: Artificial Sequence
<220> FEATURE:
<223> OTHER INFORMATION: synthetic antibody structure

<400> SEQUENCE: 76

Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Lys Gln Arg Pro Gly Glu Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Lys Phe Ala Met Asp Tyr Trp Gly Gln Gly Thr Ser
            100                 105                 110

Val Thr Val Ser Ser
        115

<210> SEQ ID NO 77
<211> LENGTH: 120
<212> TYPE: PRT
<213> ORGANISM: Artificial Sequence
<220> FEATURE:
<223> OTHER INFORMATION: synthetic antibody structure

<400> SEQUENCE: 77

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Phe
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Gly Thr His Tyr Asn Glu Lys Phe
        50                  55                  60

Lys Gly Lys Ala Thr Phe Thr Ala Asp Lys Ser Ser Asn Thr Ala Tyr
65                  70                  75                  80
```

```
Met Gln Leu Ser Ser Leu Thr Ser Glu Asp Ser Ala Val Tyr Tyr Cys
            85                  90                  95

Ala Arg Gly His Ser Tyr Tyr Phe Tyr Asp Gly Asp Tyr Trp Gly Gln
        100                 105                 110

Gly Thr Ser Val Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: synthetic antibody structure

<400> SEQUENCE: 78

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Met Lys Gln Lys Pro Gly Gln Gly Leu Glu Trp Ile
        35                  40                  45

Gly Trp Ile Asp Pro Gly Ser Gly Asn Thr Lys Tyr Asn Glu Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Thr Ala Val Tyr Phe Cys
            85                  90                  95

Ala Arg Glu Lys Thr Thr Tyr Tyr Tyr Ala Met Asp Tyr Trp Gly Gln
        100                 105                 110

Gly Thr Ser Val Thr Val Ser Ala
        115                 120

<210> SEQ ID NO 79
<211> LENGTH: 120
<212> TYPE: PRT
<213> ORGANISM: Artificial Sequence
<220> FEATURE:
<223> OTHER INFORMATION: synthetic antibody structure

<400> SEQUENCE: 79

Gln Val Gln Leu Leu Glu Ser Gly Ala Glu Leu Met Lys Pro Gly Ala
1               5                   10                  15

Ser Val Lys Ile Ser Cys Lys Ala Thr Gly Tyr Thr Phe Ser Ser Phe
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Gly Thr His Tyr Asn Glu Lys Phe
    50                  55                  60

Lys Gly Lys Ala Thr Phe Thr Ala Asp Lys Ser Asn Thr Ala Tyr
65                  70                  75                  80

Met Gln Leu Ser Ser Leu Thr Ser Glu Asp Ser Ala Val Tyr Tyr Cys
            85                  90                  95

Ala Arg Gly His Ser Tyr Tyr Phe Tyr Asp Gly Asp Tyr Trp Gly Gln
        100                 105                 110

Gly Thr Ser Val Thr Val Ser Ser
        115                 120

<210> SEQ ID NO 80
```

```
<211> LENGTH: 115
<212> TYPE: PRT
<213> ORGANISM: Artificial Sequence
<220> FEATURE:
<223> OTHER INFORMATION: synthetic antibody structure

<400> SEQUENCE: 80

Val Gln Leu Gln Gln Ser Gly Ala Glu Leu Met Lys Pro Gly Ala Ser
1               5                   10                  15

Val Lys Ile Ser Cys Lys Ala Ser Gly Tyr Thr Phe Ser Asp Tyr Trp
            20                  25                  30

Ile Glu Trp Val Lys Gln Arg Pro Gly His Gly Leu Glu Trp Ile Gly
        35                  40                  45

Glu Ile Leu Pro Gly Ser Gly Ser Thr Asn Tyr His Glu Arg Phe Lys
    50                  55                  60

Gly Lys Ala Thr Phe Thr Ala Asp Thr Ser Ser Ser Thr Ala Tyr Met
65                  70                  75                  80

Gln Leu Asn Ser Leu Thr Ser Glu Asp Ser Gly Val Tyr Tyr Cys Leu
                85                  90                  95

His Gly Asn Tyr Asp Phe Asp Gly Trp Gly Gln Gly Thr Thr Leu Thr
            100                 105                 110

Val Ser Ser
        115

<210> SEQ ID NO 81
<211> LENGTH: 121
<212> TYPE: PRT
<213> ORGANISM: Artificial Sequence
<220> FEATURE:
<223> OTHER INFORMATION: synthetic antibody structure
<220> FEATURE:
<221> NAME/KEY: MISC_FEATURE
<222> LOCATION: (20)..(20)
<223> OTHER INFORMATION: "X" may be any amino acid
<220> FEATURE:
<221> NAME/KEY: MISC_FEATURE
<222> LOCATION: (34)..(34)
<223> OTHER INFORMATION: "X" may be any amino acid
<220> FEATURE:
<221> NAME/KEY: MISC_FEATURE
<222> LOCATION: (43)..(43)
<223> OTHER INFORMATION: "X" may be any amino acid
<220> FEATURE:
<221> NAME/KEY: MISC_FEATURE
<222> LOCATION: (50)..(50)
<223> OTHER INFORMATION: "X" may be any amino acid
<220> FEATURE:
<221> NAME/KEY: MISC_FEATURE
<222> LOCATION: (52)..(52)
<223> OTHER INFORMATION: "X" may be any amino acid
<220> FEATURE:
<221> NAME/KEY: MISC_FEATURE
<222> LOCATION: (54)..(54)
<223> OTHER INFORMATION: "X" may be any amino acid
<220> FEATURE:
<221> NAME/KEY: MISC_FEATURE
<222> LOCATION: (57)..(57)
<223> OTHER INFORMATION: "X" may be any amino acid
<220> FEATURE:
<221> NAME/KEY: MISC_FEATURE
<222> LOCATION: (59)..(59)
<223> OTHER INFORMATION: "X" may be any amino acid
<220> FEATURE:
<221> NAME/KEY: MISC_FEATURE
<222> LOCATION: (99)..(99)
<223> OTHER INFORMATION: "X" may be any amino acid
<220> FEATURE:
<221> NAME/KEY: MISC_FEATURE
<222> LOCATION: (100)..(100)
<223> OTHER INFORMATION: "X" may be any amino acid
```

```
<220> FEATURE:
<221> NAME/KEY: MISC_FEATURE
<222> LOCATION: (103)..(108)
<223> OTHER INFORMATION: "X" may be any amino acid
<220> FEATURE:
<221> NAME/KEY: MISC_FEATURE
<222> LOCATION: (116)..(116)
<223> OTHER INFORMATION: "X" may be any amino acid

<400> SEQUENCE: 81

Gln Val Gln Leu Gln Gln Ser Gly Ala Glu Leu Val Lys Pro Gly Ala
1               5                   10                  15

Ser Val Lys Xaa Ser Cys Lys Ala Ser Gly Tyr Thr Phe Thr Ser Tyr
            20                  25                  30

Trp Xaa His Trp Val Lys Gln Arg Pro Gly Xaa Gly Leu Glu Trp Ile
        35                  40                  45

Gly Xaa Ile Xaa Pro Xaa Ser Gly Xaa Thr Xaa Tyr Asn Glu Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Val Tyr Cys
                85                  90                  95

Ala Arg Xaa Xaa Tyr Tyr Xaa Xaa Xaa Xaa Xaa Asp Tyr Trp Gly
            100                 105                 110

Gln Gly Thr Xaa Val Thr Val Ser Ser
            115                 120

<210> SEQ ID NO 82
<211> LENGTH: 113
<212> TYPE: PRT
<213> ORGANISM: Mus musculus

<400> SEQUENCE: 82

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 83
<211> LENGTH: 113
<212> TYPE: PRT
<213> ORGANISM: Artificial Sequence
<220> FEATURE:
<223> OTHER INFORMATION: humanized EM164 antibody

<400> SEQUENCE: 83

Asp Val Val Met Thr Gln Thr Pro Leu Ser Leu Pro Val Ser Leu Gly
1               5                   10                  15
```

```
Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 84
<211> LENGTH: 113
<212> TYPE: PRT
<213> ORGANISM: Artificial Sequence
<220> FEATURE:
<223> OTHER INFORMATION: humanized EM164 antibody

<400> SEQUENCE: 84

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 85
<211> LENGTH: 113
<212> TYPE: PRT
<213> ORGANISM: Artificial Sequence
<220> FEATURE:
<223> OTHER INFORMATION: humanized EM164 antibody

<400> SEQUENCE: 85

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
```

```
                    85                  90                  95
Ser His Val Pro Pro Thr Phe Gly Gly Gly Thr Lys Leu Glu Ile Lys
            100                 105                 110

Arg

<210> SEQ ID NO 86
<211> LENGTH: 113
<212> TYPE: PRT
<213> ORGANISM: Artificial Sequence
<220> FEATURE:
<223> OTHER INFORMATION: humanized EM164 antibody

<400> SEQUENCE: 86

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 87
<211> LENGTH: 123
<212> TYPE: PRT
<213> ORGANISM: Mus musculus

<400> SEQUENCE: 87

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Ala Gly Thr Thr Val Thr Val Ser
        115                 120

<210> SEQ ID NO 88
<211> LENGTH: 123
<212> TYPE: PRT
<213> ORGANISM: Artificial Sequence
<220> FEATURE:
<223> OTHER INFORMATION: humanized EM164 antibody
```

```
<400> SEQUENCE: 88

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Gln Lys Phe
    50                  55                  60

Gln Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser
            115                 120

<210> SEQ ID NO 89
<211> LENGTH: 339
<212> TYPE: DNA
<213> ORGANISM: Artificial Sequence
<220> FEATURE:
<223> OTHER INFORMATION: variable region of humanized EM164 antibody -
      light chain
<220> FEATURE:
<221> NAME/KEY: CDS
<222> LOCATION: (1)..(339)

<400> SEQUENCE: 89 gat gtt gtg atg acc caa act cca ctc tcc ctg cct gtc agt ctt gga        48
Asp Val Val Met Thr Gln Thr Pro Leu Ser Leu Pro Val Ser Leu Gly
1               5                   10                  15 gat cca gcc tcc atc tct tgc aga tct agt cag agc ata gta cat agt       96
Asp Pro Ala Ser Ile Ser Cys Arg Ser Ser Gln Ser Ile Val His Ser
            20                  25                  30 aat gta aac acc tat tta gaa tgg tac ctg cag aaa cca ggc cag tct      144
Asn Val Asn Thr Tyr Leu Glu Trp Tyr Leu Gln Lys Pro Gly Gln Ser
        35                  40                  45 cca agg ctc ctg atc tac aaa gtt tcc aac cga ttt tct ggg gtc cca      192
Pro Arg Leu Leu Ile Tyr Lys Val Ser Asn Arg Phe Ser Gly Val Pro
    50                  55                  60 gac agg ttc agt ggc agt gga gca ggg aca gat ttc aca ctc agg atc      240
Asp Arg Phe Ser Gly Ser Gly Ala Gly Thr Asp Phe Thr Leu Arg Ile
65                  70                  75                  80 agc aga gtg gag gct gag gat ctg gga att tat tac tgc ttt caa ggt      288
Ser Arg Val Glu Ala Glu Asp Leu Gly Ile Tyr Tyr Cys Phe Gln Gly
                85                  90                  95 tca cat gtt cct ccg acg ttc ggt gga ggc acc aaa ctg gaa atc aaa      336
Ser His Val Pro Pro Thr Phe Gly Gly Gly Thr Lys Leu Glu Ile Lys
            100                 105                 110 cgt                                                                   339
Arg

<210> SEQ ID NO 90
<211> LENGTH: 113
<212> TYPE: PRT
<213> ORGANISM: Artificial Sequence
<220> FEATURE:
<223> OTHER INFORMATION: Synthetic Construct
```

-continued

<400> SEQUENCE: 90

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 91
<211> LENGTH: 369
<212> TYPE: DNA
<213> ORGANISM: Artificial Sequence
<220> FEATURE:
<223> OTHER INFORMATION: variable region of humanized EM164 antibody -
      heavy chain
<220> FEATURE:
<221> NAME/KEY: CDS
<222> LOCATION: (1)..(369)

<400> SEQUENCE: 91 cag gtc caa ctg gtg cag tct ggg gct gaa gtg gtg aag cct ggg gct        48
Gln Val Gln Leu Val Gln Ser Gly Ala Glu Val Val Lys Pro Gly Ala
1               5                   10                  15 tca gtg aag ctg tcc tgt aag gct tct ggc tac acc ttc acc agc tac        96
Ser Val Lys Leu Ser Cys Lys Ala Ser Gly Tyr Thr Phe Thr Ser Tyr
            20                  25                  30 tgg atg cac tgg gtg aag cag agg cct gga caa ggc ctt gag tgg att       144
Trp Met His Trp Val Lys Gln Arg Pro Gly Gln Gly Leu Glu Trp Ile
        35                  40                  45 gga gag att aat cct agc aac ggt cgt act aac tac aat cag aag ttc       192
Gly Glu Ile Asn Pro Ser Asn Gly Arg Thr Asn Tyr Asn Gln Lys Phe
    50                  55                  60 cag ggg aag gcc aca ctg act gta gac aaa tcc tcc agc aca gcc tac       240
Gln Gly Lys Ala Thr Leu Thr Val Asp Lys Ser Ser Ser Thr Ala Tyr
65                  70                  75                  80 atg caa ctc agc agc ctg aca tct gag gac tct gcg gtc tat tac ttt       288
Met Gln Leu Ser Ser Leu Thr Ser Glu Asp Ser Ala Val Tyr Tyr Phe
                85                  90                  95 gca aga gga aga cca gat tac tac ggt agt agc aag tgg tac ttc gat       336
Ala Arg Gly Arg Pro Asp Tyr Tyr Gly Ser Ser Lys Trp Tyr Phe Asp
            100                 105                 110 gtc tgg ggc caa ggg acc acg gtc acc gtc tcc                           369
Val Trp Gly Gln Gly Thr Thr Val Thr Val Ser
        115                 120

<210> SEQ ID NO 92
<211> LENGTH: 123
<212> TYPE: PRT
<213> ORGANISM: Artificial Sequence
<220> FEATURE:
<223> OTHER INFORMATION: Synthetic Construct

<400> SEQUENCE: 92

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Gln Lys Phe
    50                  55                  60

Gln Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser
            115                 120

<210> SEQ ID NO 93
<211> LENGTH: 339
<212> TYPE: DNA
<213> ORGANISM: Artificial Sequence
<220> FEATURE:
<223> OTHER INFORMATION: light chain variable region of humanized EM164
      v1.1 antibody
<220> FEATURE:
<221> NAME/KEY: CDS
<222> LOCATION: (1)..(339)

<400> SEQUENCE: 93 gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat cca gcc tcc atc tct tgc aga tct agt cag agc ata gta cat agt      96
Asp Pro Ala Ser Ile Ser Cys Arg Ser Ser Gln Ser Ile Val His Ser
            20                  25                  30 aat gta aac acc tat tta gaa tgg tac ctg cag aaa cca ggc cag tct     144
Asn Val Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga gca ggg aca gat ttc aca ctc agg atc     240
Asp Arg Phe Ser Gly Ser Gly Ala Gly Thr Asp Phe Thr Leu Arg Ile
65                  70                  75                  80 agc aga gtg gag gct gag gat ctg gga att tat tac tgc ttt caa ggt     288
Ser Arg Val Glu Ala Glu Asp Leu Gly Ile Tyr Tyr Cys Phe Gln Gly
                85                  90                  95 tca cat gtt cct ccg acg ttc ggt gga ggc acc aaa ctg gaa atc aaa     336
Ser His Val Pro Pro Thr Phe Gly Gly Gly Thr Lys Leu Glu Ile Lys
            100                 105                 110 cgt                                                                  339
Arg

<210> SEQ ID NO 94
<211> LENGTH: 113
<212> TYPE: PRT
<213> ORGANISM: Artificial Sequence
<220> FEATURE:
<223> OTHER INFORMATION: light chain variable region of humanized EM164

-continued v1.1 antibody

<400> SEQUENCE: 94

Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 95
<211> LENGTH: 339
<212> TYPE: DNA
<213> ORGANISM: Artificial Sequence
<220> FEATURE:
<223> OTHER INFORMATION: light chain variable region of humanized EM164
      v1.2 antibody
<220> FEATURE:
<221> NAME/KEY: CDS
<222> LOCATION: (1)..(339)

<400> SEQUENCE: 95 gat gtt ttg atg acc caa act cca ctc tcc ctg cct gtc agt ctt gga    48
Asp Val Leu Met Thr Gln Thr Pro Leu Ser Leu Pro Val Ser Leu Gly
1               5                   10                  15 gat cca gcc tcc atc tct tgc aga tct agt cag agc ata gta cat agt    96
Asp Pro Ala Ser Ile Ser Cys Arg Ser Ser Gln Ser Ile Val His Ser
            20                  25                  30 aat gta aac acc tat tta gaa tgg tac ctg cag aaa cca ggc cag tct   144
Asn Val Asn Thr Tyr Leu Glu Trp Tyr Leu Gln Lys Pro Gly Gln Ser
        35                  40                  45 cca agg ctc ctg atc tac aaa gtt tcc aac cga ttt tct ggg gtc cca   192
Pro Arg Leu Leu Ile Tyr Lys Val Ser Asn Arg Phe Ser Gly Val Pro
    50                  55                  60 gac agg ttc agt ggc agt gga gca ggg aca gat ttc aca ctc agg atc   240
Asp Arg Phe Ser Gly Ser Gly Ala Gly Thr Asp Phe Thr Leu Arg Ile
65                  70                  75                  80 agc aga gtg gag gct gag gat ctg gga att tat tac tgc ttt caa ggt   288
Ser Arg Val Glu Ala Glu Asp Leu Gly Ile Tyr Tyr Cys Phe Gln Gly
                85                  90                  95 tca cat gtt cct ccg acg ttc ggt gga ggc acc aaa ctg gaa atc aaa   336
Ser His Val Pro Pro Thr Phe Gly Gly Gly Thr Lys Leu Glu Ile Lys
            100                 105                 110 cgt                                                                339
Arg

<210> SEQ ID NO 96
<211> LENGTH: 113
<212> TYPE: PRT
<213> ORGANISM: Artificial Sequence
<220> FEATURE:
<223> OTHER INFORMATION: light chain variable region of humanized EM164 v1.2 antibody

<400> SEQUENCE: 96

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 97
<211> LENGTH: 339
<212> TYPE: DNA
<213> ORGANISM: Artificial Sequence
<220> FEATURE:
<223> OTHER INFORMATION: light chain variable region of humanized EM164 v1.3 antibody
<220> FEATURE:
<221> NAME/KEY: CDS
<222> LOCATION: (1)..(339)

<400> SEQUENCE: 97

```
gat gtt gtg atg acc caa act cca ctc tcc ctg cct gtc agt ctt gga    48
Asp Val Val Met Thr Gln Thr Pro Leu Ser Leu Pro Val Ser Leu Gly
1               5                   10                  15 gat cca gcc tcc atc tct tgc aga tct agt cag agc ata gta cat agt    96
Asp Pro Ala Ser Ile Ser Cys Arg Ser Ser Gln Ser Ile Val His Ser
            20                  25                  30 aat gta aac acc tat tta gaa tgg tac ctg cag aaa cca ggc cag tct   144
Asn Val Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
50                  55                  60 gac agg ttc agt ggc agt gga gca ggg aca gat ttc aca ctc agg atc   240
Asp Arg Phe Ser Gly Ser Gly Ala Gly Thr Asp Phe Thr Leu Arg Ile
65                  70                  75                  80 agc aga gtg gag gct gag gat ctg gga att tat tac tgc ttt caa ggt   288
Ser Arg Val Glu Ala Glu Asp Leu Gly Ile Tyr Tyr Cys Phe Gln Gly
                85                  90                  95 tca cat gtt cct ccg acg ttc ggt gga ggc acc aaa ctg gaa atc aaa   336
Ser His Val Pro Pro Thr Phe Gly Gly Gly Thr Lys Leu Glu Ile Lys
            100                 105                 110 cgt                                                                339
Arg
```

<210> SEQ ID NO 98
<211> LENGTH: 113
<212> TYPE: PRT
<213> ORGANISM: Artificial Sequence
<220> FEATURE:
<223> OTHER INFORMATION: light chain variable region of humanized EM164

-continued

```
    v1.3 antibody

<400> SEQUENCE: 98

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
            85                  90                  95

Ser His Val Pro Pro Thr Phe Gly Gly Gly Thr Lys Leu Glu Ile Lys
            100                 105                 110

Arg
```